US012773453B2

(12) United States Patent
Whiting et al.

(10) Patent No.: US 12,773,453 B2
(45) Date of Patent: Oct. 27, 2026

(54) FLUORESCENT SYSTEMS FOR BIOLOGICAL IMAGING AND USES THEREOF

(71) Applicant: LIGHTOX LIMITED, Wynyard Billingham Durham (GB)

(72) Inventors: Andrew Whiting, Wynyard Billingham Durham (GB); Carrie Ambler, Wynyard Billingham Durham (GB); David Chisholm, Wynyard Billingham Durham (GB)

( * ) Notice: Subject to any disclaimer, the term of this patent is extended or adjusted under 35 U.S.C. 154(b) by 1273 days.

(21) Appl. No.: 17/597,607

(22) PCT Filed: Jul. 14, 2020

(86) PCT No.: PCT/GB2020/051694
§ 371 (c)(1),
(2) Date: Jan. 13, 2022

(87) PCT Pub. No.: WO2021/009506
PCT Pub. Date: Jan. 21, 2021

(65) Prior Publication Data
US 2022/0347299 A1 Nov. 3, 2022

(30) Foreign Application Priority Data
Jul. 17, 2019 (GB) ..................................... 1910239

(51) Int. Cl.

| | |
|---|---|
| ***A61K 47/64*** | (2017.01) |
| ***A61K 41/00*** | (2020.01) |
| ***A61K 47/54*** | (2017.01) |
| ***A61K 47/68*** | (2017.01) |
| ***C07C 229/44*** | (2006.01) |
| ***C07D 213/55*** | (2006.01) |
| ***C07D 233/96*** | (2006.01) |
| ***C07D 295/155*** | (2006.01) |
| ***C07D 295/185*** | (2006.01) |
| ***C07D 333/24*** | (2006.01) |
| ***C07D 417/06*** | (2006.01) |
| ***G01N 21/64*** | (2006.01) |
| ***G01N 21/65*** | (2006.01) |

(52) U.S. Cl.
CPC ........ *A61K 41/0057* (2013.01); *A61K 47/545* (2017.08); *A61K 47/64* (2017.08); *A61K 47/68* (2017.08); *C07C 229/44* (2013.01); *C07D 213/55* (2013.01); *C07D 233/96* (2013.01); *C07D 295/155* (2013.01); *C07D 295/185* (2013.01); *C07D 333/24* (2013.01); *C07D 417/06* (2013.01); *G01N 21/6428* (2013.01); *G01N 21/65* (2013.01)

(58) Field of Classification Search
CPC ........ A61K 41/00; A61K 47/68; A61K 47/64; C07D 295/155; C07D 295/185
See application file for complete search history.

(56) References Cited

U.S. PATENT DOCUMENTS

| | | | |
|---|---|---|---|
| 5,449,809 | A | 9/1995 | Wingert et al. |
| 2005/0064130 | A1 | 3/2005 | Nishikawa |

FOREIGN PATENT DOCUMENTS

| | | | | |
|---|---|---|---|---|
| CN | 106 588 789 A | | 4/2017 | |
| EP | 0 493 716 A1 | | 7/1992 | |
| JP | 2004123579 A | | 4/2004 | |
| JP | 2004250399 A | | 9/2004 | |
| JP | 2004317777 A | | 11/2004 | |
| WO | WO 2016055800 | * | 4/2016 | |
| WO | WO-2018029473 A1 | * | 2/2018 | ........... A61K 47/551 |

OTHER PUBLICATIONS

Fernandes, S. S., et al. (2017). Synthesis and characterization of push-pull bithiophene and thieno[3,2-b] thiophene derivatives bearing an ethyne linker as sensitizers for dye-sensitized solar cells. Organic Electronics, 49, 194-205. https://doi.org/10.1016/j.orgel.2017.06.048.
Yamaguchi, E., Shibahara, F, & Murai, T. (2011). 1-Alkynyl- and 1-alkenyl-3-arylimidazo[1,5-a]pyridines: synthesis, photophysical properties, and observation of a linear correlation between the fluorescent wavelength and Hammett substituent constants. The Journal of organic chemistry, 76 15, 6146-58.
ISR: European Patent Office; Jun. 11, 2020.
European Search Report; European Patent Office; Dec. 22, 2021.
Milan Klikar et al; "N, N' -Dibutylbarbituric Acid as an Acceptor Moiety in Push-Pull Chromophores", Jan. 1, 2013.
Herbert Meier et al; "Push-Pull Oligomers With 2, 2-Dicyanovinyl Groups as Electron Acceptors," Feb. 1, 2007.
Baleeva N S et al: "The Sonogashira Reaction as a New Method for the Modification of Borated Analogues of the Green Fluorescence Protein Chromophore", Sep. 21, 2017.
(Continued)

*Primary Examiner* — Michael G. Hartley
*Assistant Examiner* — Jagadishwar R Samala
(74) *Attorney, Agent, or Firm* — PatShegen IP; Moshe Pinchas

(57) ABSTRACT

The invention discloses a dye sensitizer molecule taking triazole as a core and a preparation method of the dye sensitizer molecule. According to the dye molecule, a triazole ring is introduced to the design of a molecular structure, and the electronic absorption and transmission capability among D-pi-A dye molecules are greatly improved by substituting donors with different carbon chain lengths and receptors with triple bonds at the periphery, so that a novel triazole dye with high efficiency is obtained. The preparation method of the compound comprises: click chemical reaction, detrimethylsilyl reaction, Sonogashira coupling reaction and the like; and the prepared dye molecule can be applied to a dye-sensitive solar cell and can show favorable photoelectric conversion property so as to have wide application prospects on the aspects of energy development and utilization. In addition, the material also has liquid crystal property under a certain condition so as to also have a huge potential on the aspect of application to photoelectric devices.

19 Claims, 42 Drawing Sheets

(56) References Cited

OTHER PUBLICATIONS

Fernandes Sara S M et al; Theoretical and Experimental Studies of Aryl-Bithiophene Based Push-Pull [PI]-Conjugated Heterocyclic Systems Bearing Cyanoacetic or Rhodanine-3-Acetic Acid Acceptors for SHG Nonlinear Optical Applications; Oct. 3, 2017.
Le Falher Laetita et al: "Chemoselective Access to [PI]-Conjugated Heterocycles By Stille and Sonogashira Reactions On 2- Substituted 4 H- Pyrido [E] [1,3] Oxazin-4-Ones"; Jan. 26, 2017.
Yin Haijing et al; "Two-Photon Fluorescent Probes for Biological Mg 2+ Detection Based on 7- Substituted Coumarin," May 1, 2015.
Reekie Tristan A. et al; Ester-Substituted Electron-Poor Alkenes for Cycloaddition-Retroelectrocyclization (CA-RE) and Related Reactions: Alkenes for Cycloaddition-Retroelectrocyclization Reactions, Oct. 19, 2015.
Sadownik Jan W et al: "Generating System-Level Responses From a Network of Simple Synthetic Replicators," Dec. 6, 2017.

* cited by examiner 1
2
3
4
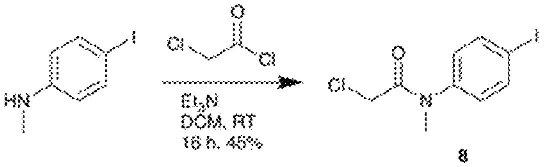
8
FIG. 1(iii)

8 9 10

10 11

1 16

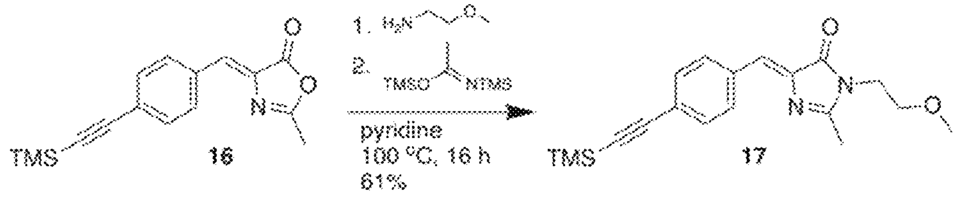
FIG. 1(vii)
FIG. 1(viii)

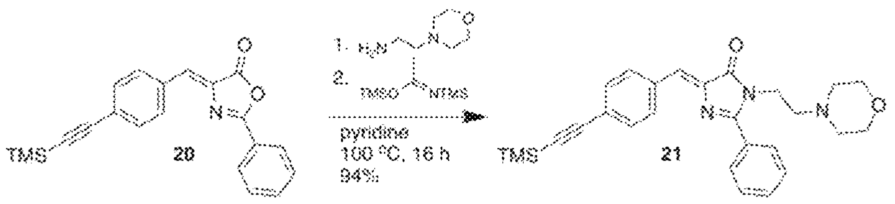
FIG. 1(x)
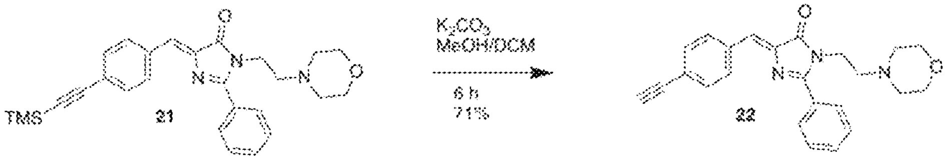
FIG. 1(xi)
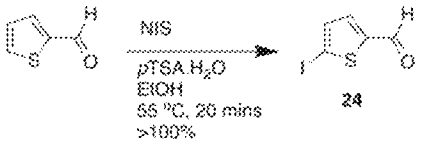
FIG. 1(xii)
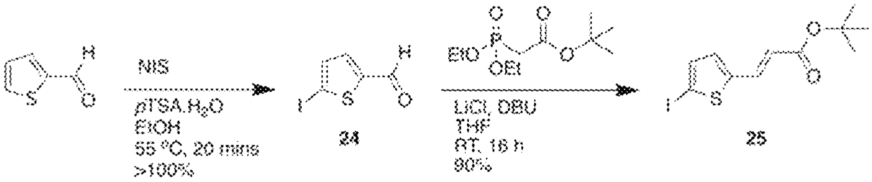
FIG. 1(xiii)

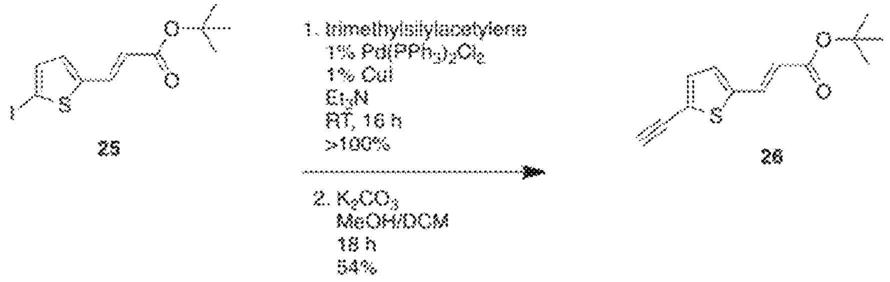
FIG. 1(xiv)
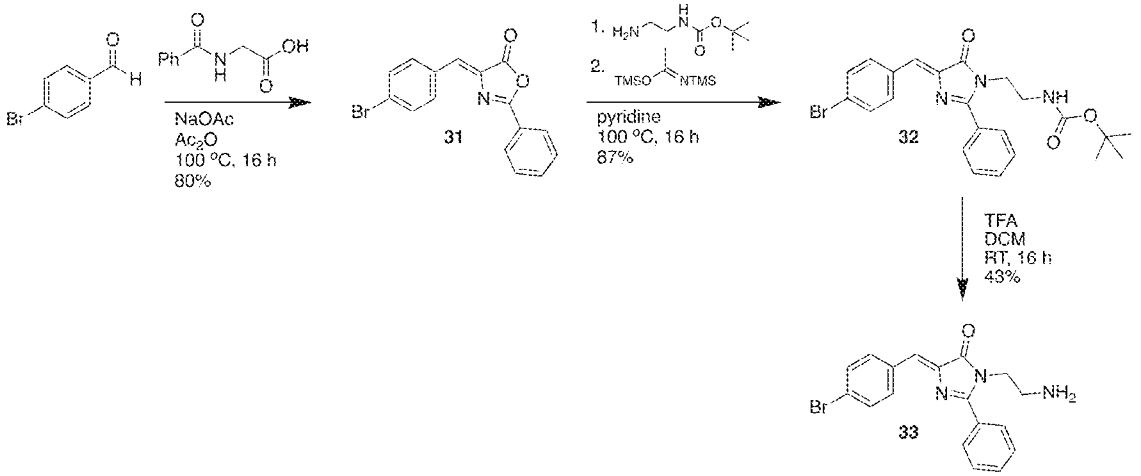
FIG. 1(xvi)

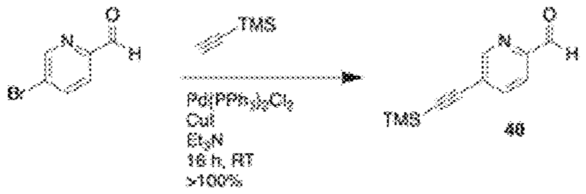
FIG. 1(xvii)
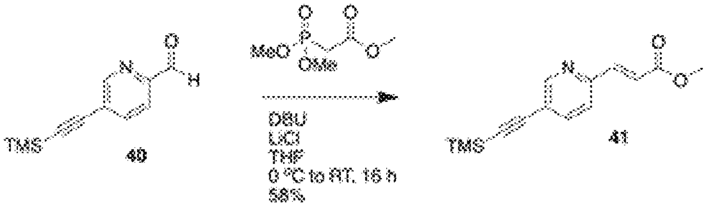
FIG. 1(xviii)
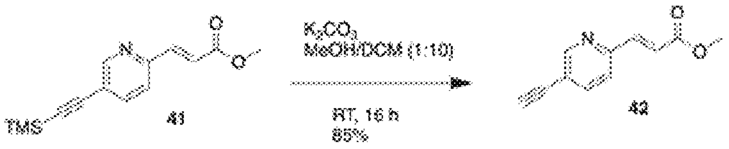
FIG. 1(xix)

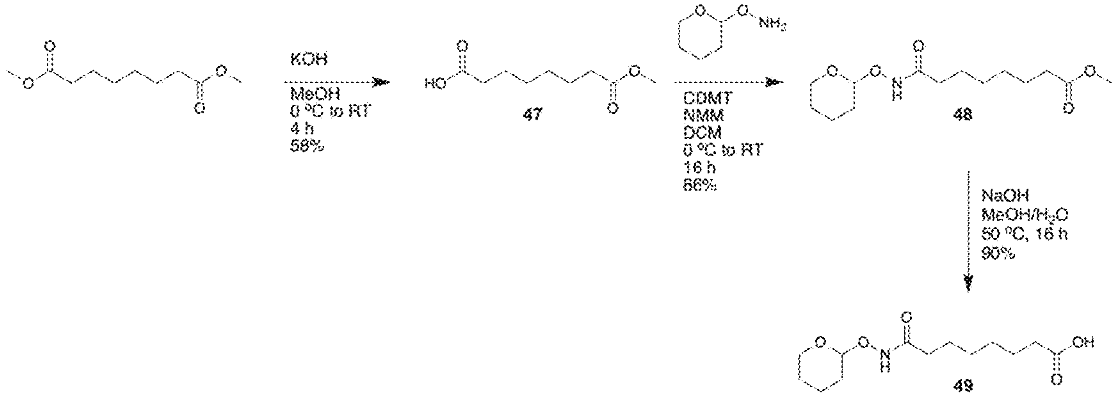
FIG. 1(xxi)
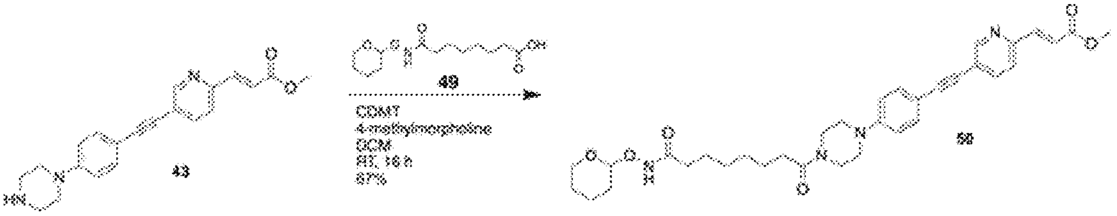
FIG. 1(xxii)
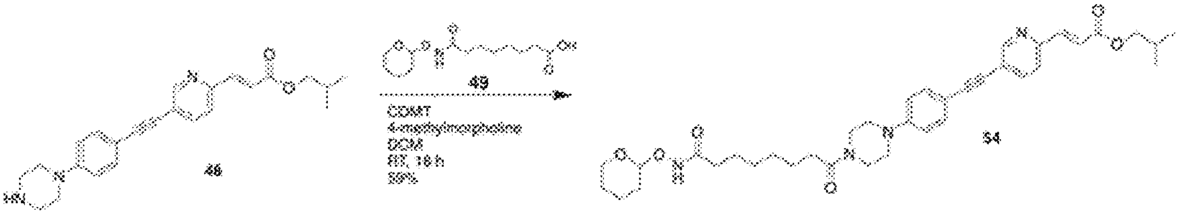
FIG. 1(xxiii)

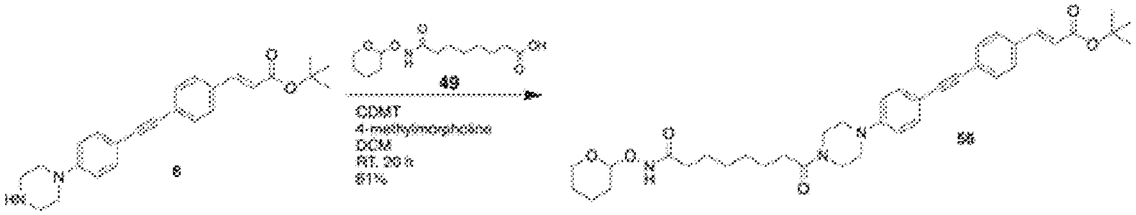
FIG. 1(xxiv)
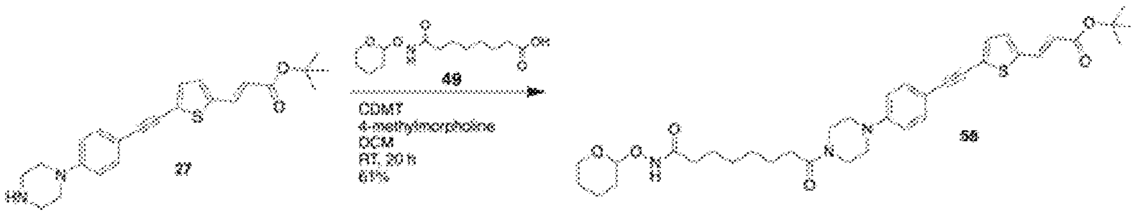
FIG. 1(xxv)
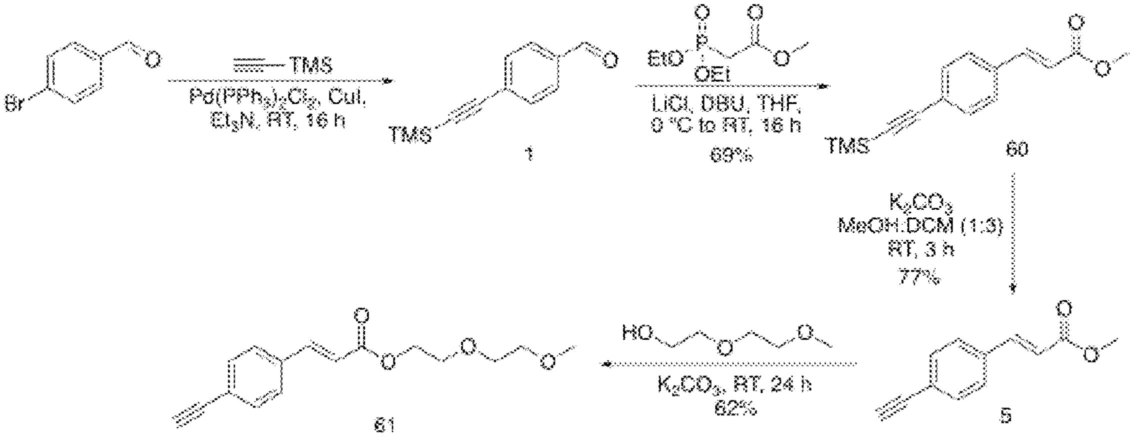
FIG. 1(xxvi)

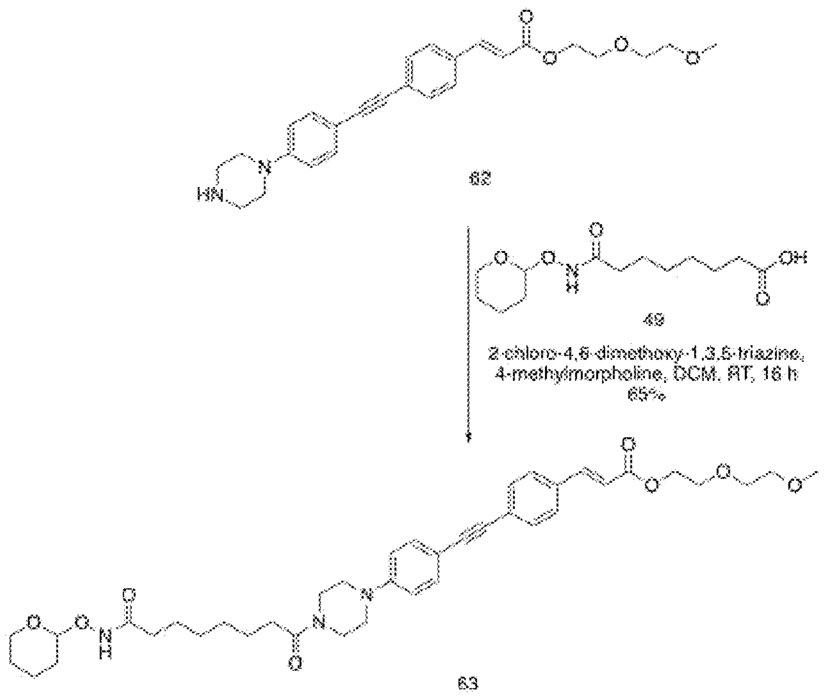
62
49
63
FIG. 1(xxvii)
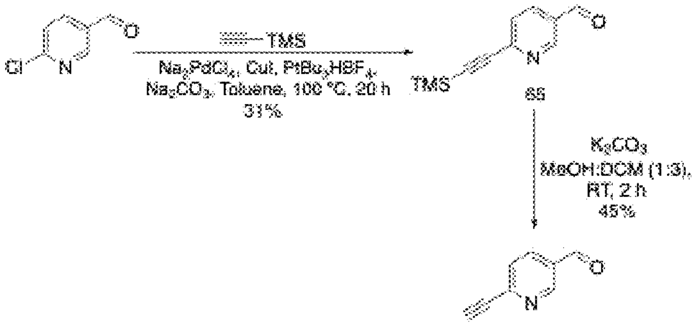
65
66
FIG. 1(xxviii)

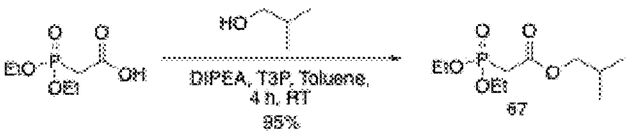
FIG. 1(xxix)
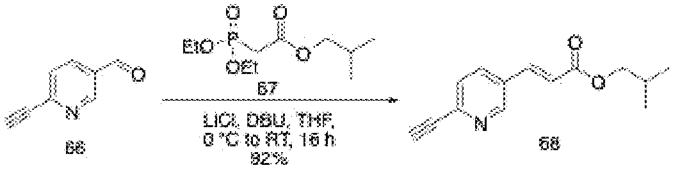
FIG. 1(xxx)
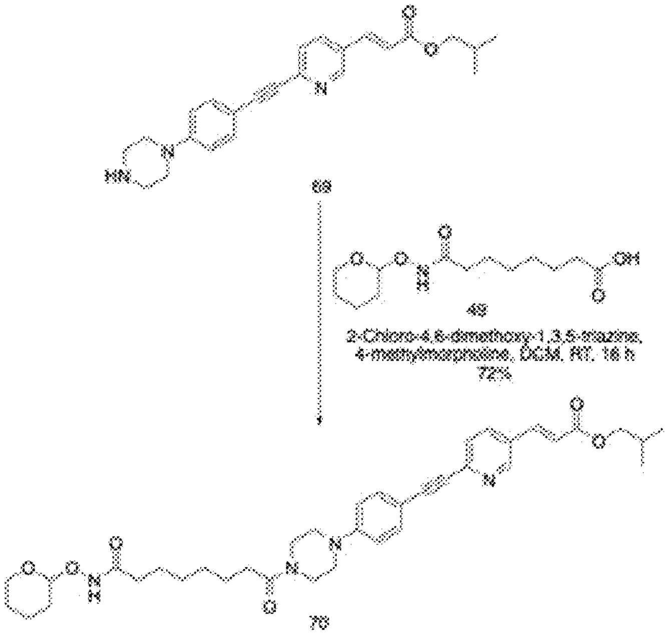
FIG. 1(xxxi)

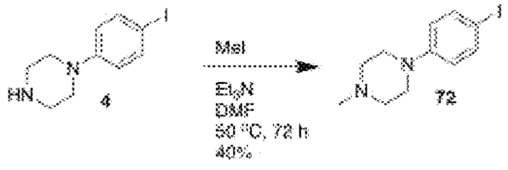
FIG. 1(xxxii)
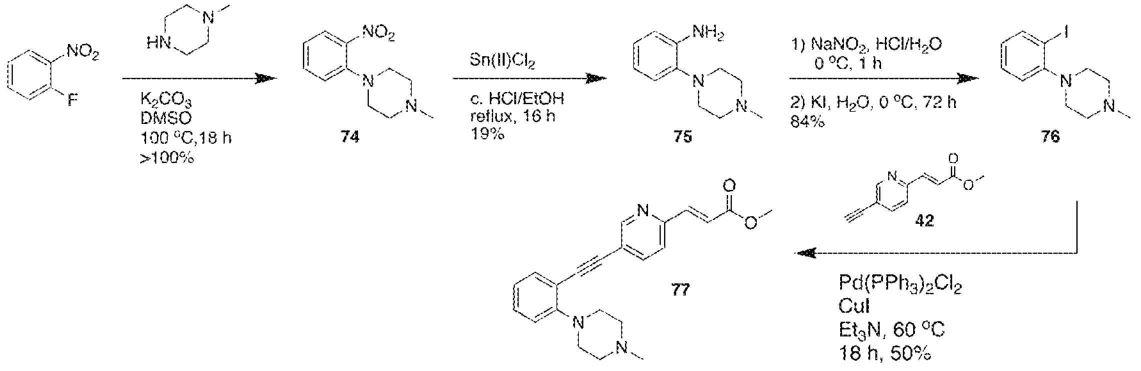
FIG. 1(xxxiii)
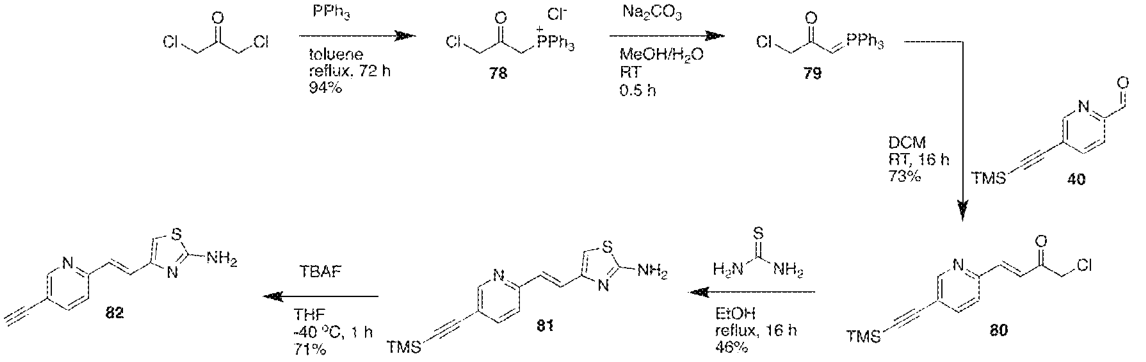
FIG. 1(xxxiv)

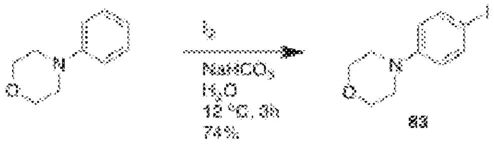
83
FIG. 1(xxxv)

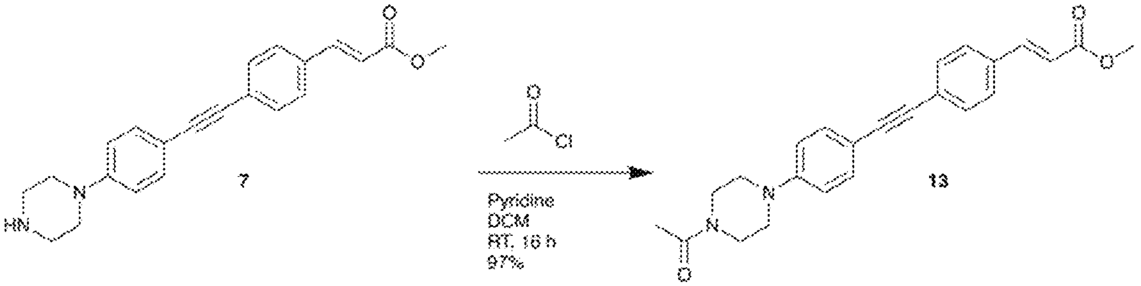
FIG. 2(iii)

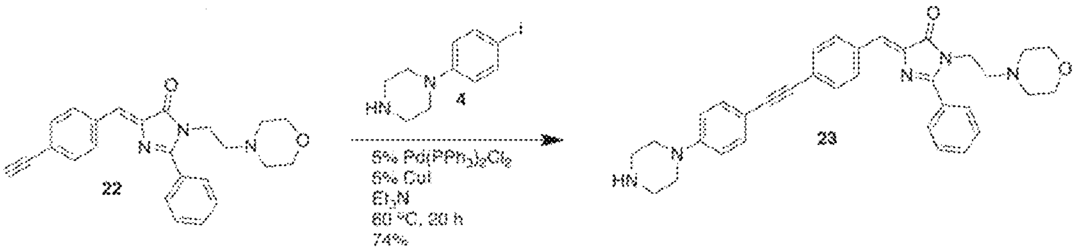
FIG. 2(vii)
FIG. 2(viii)

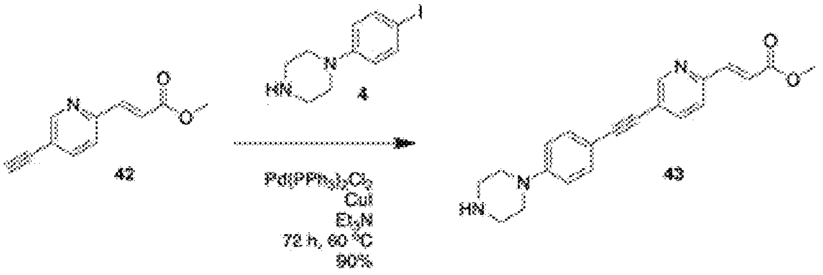
FIG. 2(xi)
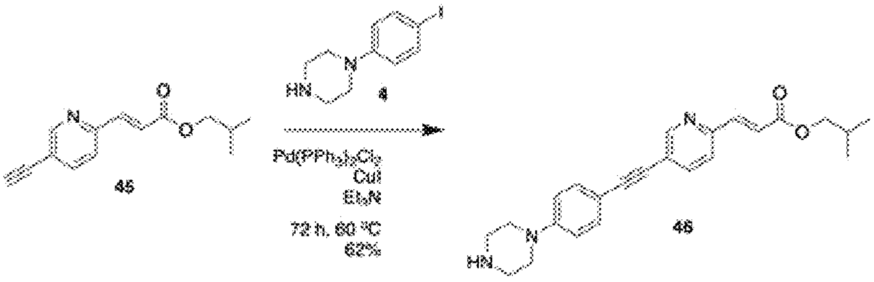
FIG. 2(xii)
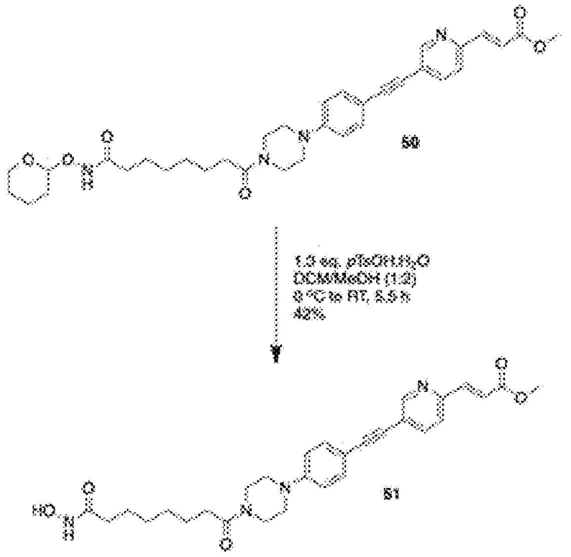
FIG. 2(xiii)

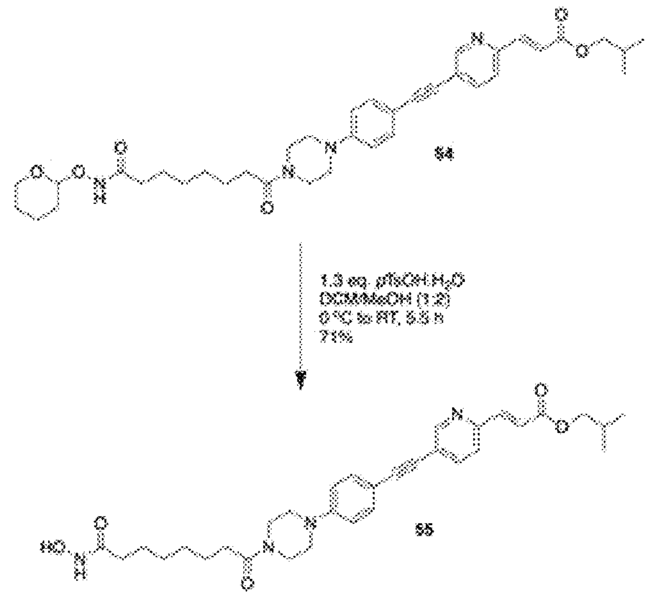
FIG. 2(xiv)

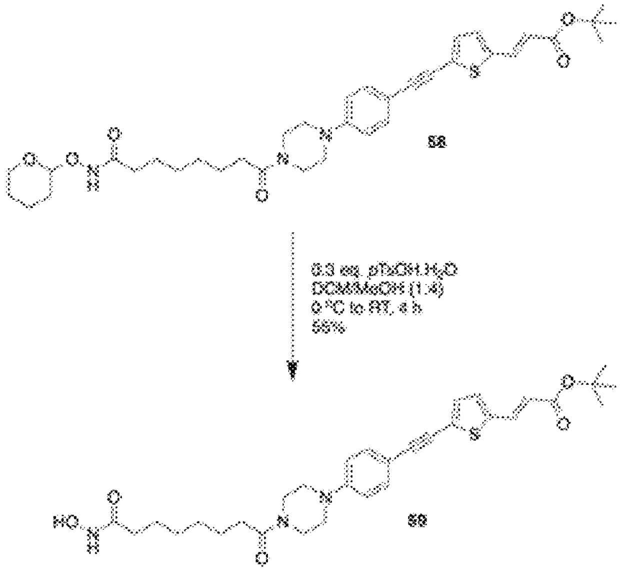
FIG. 2(xvi)
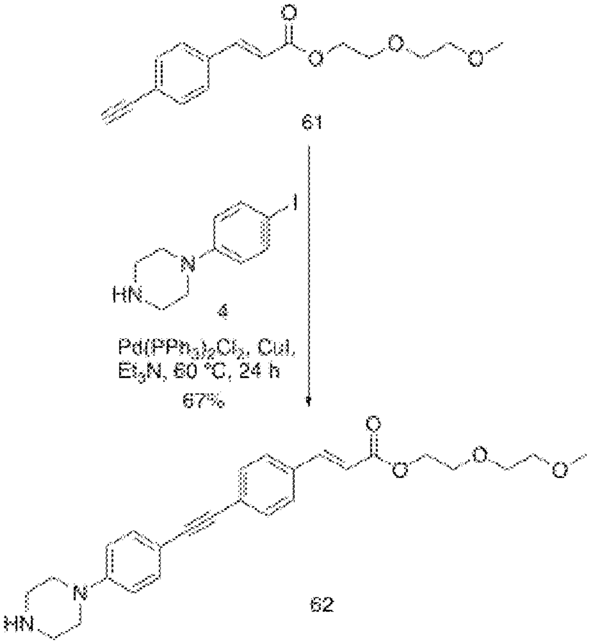
FIG. 2(xvii)

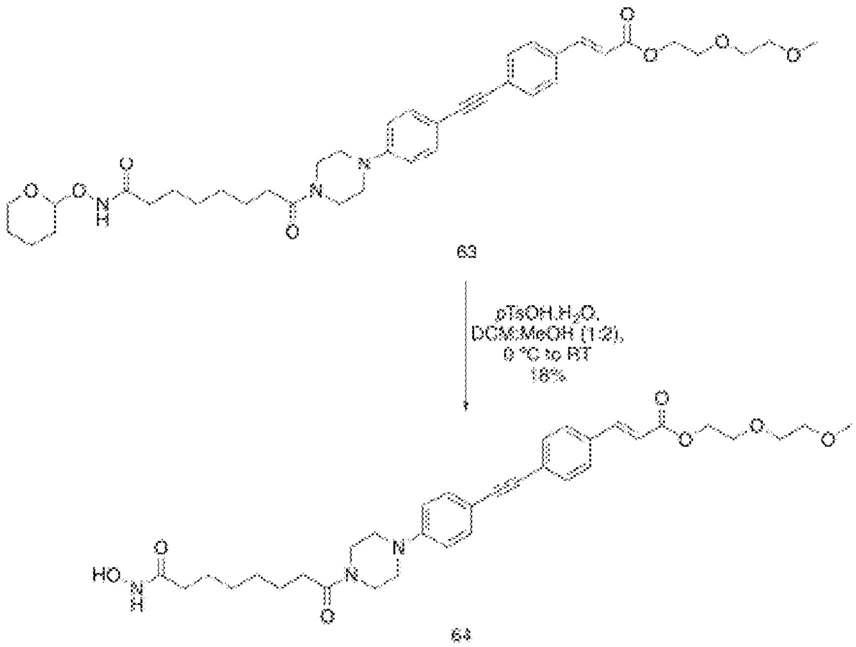
63
64
FIG. 2(xviii)
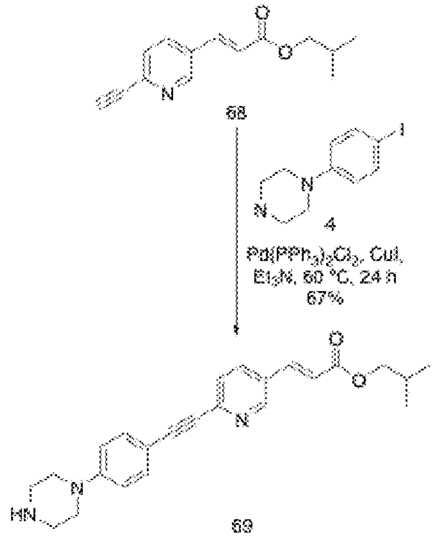
68
4
69
FIG. 2(xix)

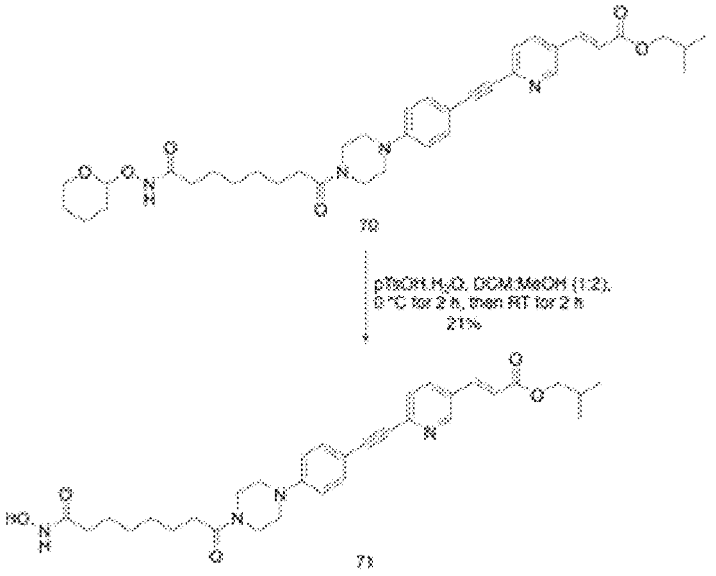
FIG. 2(xx)
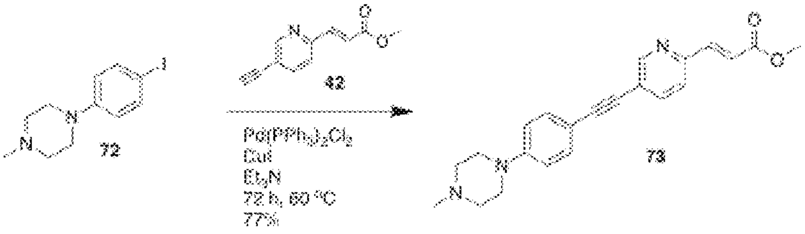
FIG. 2(xxi)
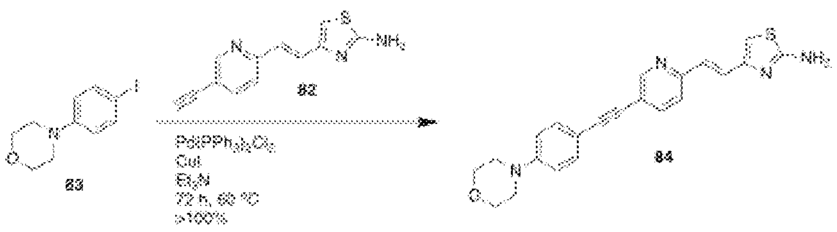
FIG. 2(xxii)

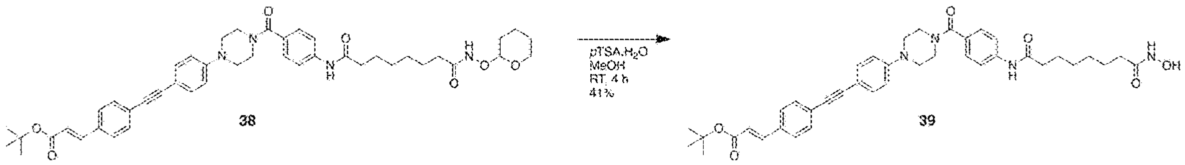
FIG. 4(iii)

FLUORESCENT SYSTEMS FOR BIOLOGICAL IMAGING AND USES THEREOF

The present invention relates to compounds of formula I:

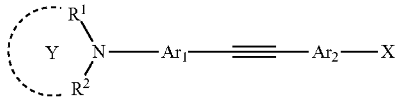

I in which Y, $Ar_1$, $Ar_2$, X, $R^1$ and $R^2$ are defined herein, and to their use in a variety of biological imaging techniques and therapeutic methods. The invention also relates to conjugates comprising the compounds of formula I and their associated uses and therapeutic uses.

Fluorescence imaging has rapidly become a powerful tool for investigating biological processes, particularly in living cells where cellular events may be observed in their physiological contexts. The development of single-molecule visualisation techniques has greatly enhanced the usefulness of fluorescence microscopy for such applications, enabling the tracking of proteins and small molecules in their endogenous environments. From probes that can detect particular molecules, to compounds that localise to specific organelles in the cell, the area of biological imaging has become a highly emergent field.

Fluorescent synthetic retinoids, such as those described in WO 2016/055800 A, have been used as research tools in the field of fluorescence imaging, providing valuable insights into retinoid activity and metabolism in the natural environment via tracking of cellular uptake and localisation. However, the expansive biology of retinoid signalling makes targeting using retinoids difficult, thereby limiting their broader use as fluorescent probes and as therapeutics.

The development of reliable markers for non-mammalian cell types is also challenging. For instance, although some commercially available fluorescent probes that target specific organelle in mammalian cells can be used in plants, signal quality and specificity are often poor, and labelling efficiency is impacted by the relatively high molecular weight of the fluorescent compounds. In addition, known fluorescent probes often have an excitation range similar to chlorophyll, leading to signal interference in plant cell imaging.

Consequently, it would be advantageous to provide a fluorescent compound which mitigates one or more of these disadvantages, and which can be used as a versatile fluorophore in a wide variety of imaging and bio-targeting techniques. A compound which has enhanced flexibility in terms of functionality, i.e. to facilitate the attachment of a range of targeting or reactive groups, or to manipulate and extend the chromophore, would be beneficial, as would good physical properties, such as good aqueous solubility. Good photoactive properties, such as the ability to act as photosensitizers when activated by an appropriate wavelength of light would also be advantageous, leading to utility in photodynamic therapy (PDT) and a variety of ROS-mediated applications across different cell types.

SUMMARY OF THE INVENTION

Accordingly, the present invention relates generally to fluorescent compounds and their use in a variety of biological imaging and targeting techniques.

In aspects the present invention relates to the novel compounds per se, and to their use as biological probes, and specifically fluorescent probes.

In aspects the present invention relates to the use of the compounds in Raman imaging and fluoRaman imaging techniques, and associated imaging methods.

In aspects, the invention relates to methods of deprotecting the compounds to form deprotected compounds for conjugation, as well as to the deprotected compounds formed by those methods.

In aspects, the invention relates to the modulation of the properties of the compounds of formula I to incorporate targeting functions for cell-localisation.

In aspects, the invention relates to conjugates comprising the compounds, and to the use of these conjugates in imaging, therapeutic and non-therapeutic applications. The conjugate may comprise, for instance; a compound of the invention conjugated directly to a targeting or active agent, or conjugated using a linker or spacer group.

In aspects, the invention relates to pharmaceutical compositions comprising such compounds and conjugates, and to the use of such compounds, conjugates and compositions in the treatment of a variety of conditions or diseases. In aspects, this includes the use of the compounds for controlled reactive oxygen species (ROS) generation applications for therapeutic use.

In aspects, the invention relates to formulations comprising such compounds and conjugates, and to the use of such compounds, conjugates and formulations in controlled ROS generation applications in plant, fungal and bacterial cells.

Further aspects and embodiments of the invention are as defined in the claims, and described in more detail below.

According to the present invention there is provided a compound of formula I:

I

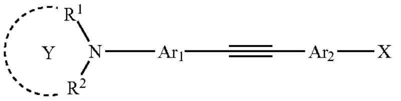

in which:

$R^1$ is H or an alkyl group comprising from 1 to 10 carbon atoms, optionally substituted with one or more N atoms, and $R^2$ is selected from an alkyl group comprising from 1 to 10 carbon atoms, optionally substituted with one or more N atoms, $—(CH_2)_nR^3$, $—(CH_2)_nNHR^3$, and $—(CH_2)_2(COCH_2)_nR^3$ in which n is an integer from 1 to 10 and $R^3$ is $—NH_2$, —OH, $—SO_2PhCH_3$, or —COOH, or $R^2$ is $—C(O)(CH_2)_nC(O)R^8$, $—C(O)(CH_2)_mO(CH_2)_mC(O)R^8$, $—C(O)(CH_2)_nCH(CH_3)C(O)R^8$, $—S(O)_2(CH_2)_nC({=}O)R^8$, $—S^+(O^-)(CH_2)_nC({=}O)R^8$ or $—(CH_2)_nPPh_3{}^+Br^-$ in which $R^8$ is —OH or —NHOH, n is an integer from 1 to 8, and m is an integer from 1 to 4; or $R^1$ and $R^2$ form part of a heterocyclic group Y having from 3 to 12 ring members, $Ar_1$ and $Ar_2$ are each, independently, an aromatic group; and X is selected from unsaturated esters, ketones, carboxylic acids, imidazolones, pyridines, oxazolones, oxazolidinones, barbituric acids and thiobarbituric acids; with the proviso that when $Ar_1$ is phenyl, and $R_1$ and $R_2$ form part of a heterocyclic group Y having from 3 to 12 ring members, the N of the heterocyclic group is in a para position relative to the acetylene group of the compound of formula I;

and diastereoisomers thereof, in free or salt form.

In general terms, the compound of formula I is based generally on a diarylacetylene, exemplified by a diphenylacetylene structure, with a para-amino (electron donating group) on one end, and a para-electron withdrawing group on the other end, creating a dipolar system through electronic conjugation.

The inventors have advantageously discovered that compounds of formula I have surprising utility in biological imaging techniques. For instance, the compounds have been demonstrated to penetrate into mammalian, bacterial, fungal and plant cells, making them broadly applicable to a host of imaging applications. The unique structure of the compounds provides flexibility in terms of functionality around the system, i.e. to allow the attachment of targeting or reactive groups, in particular via reaction with an amine group of the Y, $R^1$ or $R^2$ moieties but also at other positions, such as the X group. This can allow the incorporation of reactive functions such as photoaffinity labels to enable in situ reaction, the attachment of targeting functions, such as the incorporation of targeting motifs for subcellular localisation, and/or conjugation or attachment to other small molecule drugs and biomolecules such as peptides, antibodies and the like. The reduced molecular weight of the compounds relative to previously known fluorescent probes facilitates penetration into the cell, and allows moieties, such as cancer drugs for example, to exhibit unchanged targeting when conjugated to the compounds, as has been demonstrated with a model drug, vorinostat. The ability of the compounds to act as photosensitisers provides a variety of useful applications via the control of ROS, such as in photodynamic therapy (PDT), optionally in combination with a conjugated drug molecule, and in plant, fungal and bacterial cells, for instance in the preparation of targeted herbicides or in seed enhancement applications. The flexibility of the molecular structure in terms of its modular nature also presents the possibility of incorporating a second fluorophore capable of excitation at a different wavelength, and leading to a host of additional potential applications. The structure of the compounds also allows them to be used in Raman imaging and fluoRaman imaging techniques. The inventors have shown that, surprisingly, in those embodiments of the invention in which $Ar_1$ is phenyl and $R^1$ and $R^2$ form part of a heterocyclic group Y, the para-positioning of the nitrogen of the heterocyclic group with respect to the central acetylene group of the compound shows significantly more efficiency in terms of photophysical properties when compared with the ortho-positioned equivalents. This has significant advantages in terms of their use in imaging techniques.

The compounds of the invention have the general structure shown in Formula I above.

The term "diastereoisomers" as used herein refers to isomers that possess identical constitution, but which differ in the arrangement of their atoms in space. In particular, the term "diastereoisomers" is intended to cover alkene diastereoisomers.

The term "heterocyclic group" as used herein means a monocyclic or bicyclic ring group containing from 3 to 12 ring members and optionally containing 1 to 3 heteroatoms or functional groups selected from the group consisting of N, S, SO, $SO_2$, $O_2$, and O, in addition to the formula I Nitrogen atom. As used herein, the term "heterocyclic group" includes aromatic, partially unsaturated and saturated ring systems. Examples of non-aromatic groups include piperidinyl, piperazinyl, morpholinyl, thiomorpholinyl, dioxidothiomorpholinyl, pyrrolidin-1-yl, pyrrolidin-3-yl, azetidine-1-yl, azetidine-3-yl, aziridine-1-yl, azepan-1-yl, azepan-3-yl, azepan-4-yl, but are not limited thereto. Examples of aromatic (heteroaryl) groups include pyrrolyl, imidazolyl, pyrazolyl, pyridinyl, pyrimidinyl, indolyl and benzothiadiazolyl groups, but are not limited thereto. In an embodiment, the heterocyclic group is a saturated ring system. The heterocyclic group may be optionally substituted. In an embodiment, the heterocyclic group may be substituted with an alkyl group, $—COCH_3$, $—C(O)(CH_2)_nC(O)R^8$, $—C(O)(CH_2)_mO(CH_2)_mC(O)R^8$, $—C(O)(CH_2)_nCH(CH_3)C(O)R^8$, $—S(O)_2(CH_2)_nC({=}O)R^8$, $—S^+(O^-)(CH_2)_nC({=}O)R^8$ or $—(CH_2)_nPPh_3{}^+Br^-$, in which $R^8$ is —OH or —NHOH, n is an integer from 1 to 8, and m is an integer from 1 to 4.

By "the N of the heterocyclic group is in a para position with respect to the acetylene group" it is meant that the N which forms part of heterocyclic group Y is a para-substituted donor group in the compound, and is in a para position with respect to the central acetylene moiety of the compound of formula I for those embodiments in which $Ar_1$ is phenyl. For the avoidance of doubt, when the heterocyclic group contains more than one nitrogen atom, one of the N atoms is in such a para position.

The term "aromatic group" as used herein includes both carbocyclic and heterocyclic, unsaturated ring groups comprising from 5 to 19 ring atoms and preferably from 5 to 13 ring atoms. The aromatic group may be monocyclic or polycyclic, and is preferably mono-, bi- or tri-cyclic, and more preferably mono or bicyclic. In heterocyclic aromatic groups, the ring group may comprise one or more N, O or S atoms. Examples of suitable aromatic groups include pyrrole, furan, benzofuran, thiophene, phenyl, imidazole, pyrazole, oxazole, thiazole, oxathiazole, pyridine, pyrimidine, pyrazine, pyridazine and triazine. The aromatic group may optionally be substituted, for instance with groups such as fluorides, chlorides, bromides and iodides, alkyl groups, alkenyl groups, amine groups ($—CH_2—(CH_2)_n—NH_2$), hydroxyl groups ($—CH_2—(CH_2)_n—OH$) and carboxyl groups ($—CH_2—(CH_2)_n—COOH$), where n may equal 0 to 10, or an aromatic or PEG-derived group.

In an embodiment, $Ar_2$ is selected from:

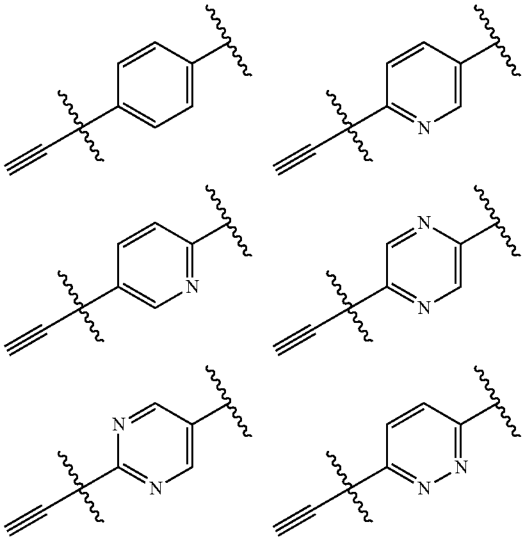

-continued

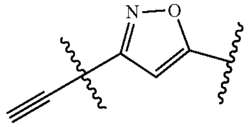
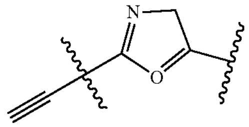
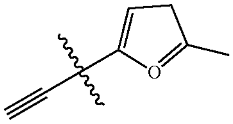
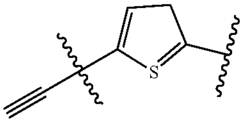
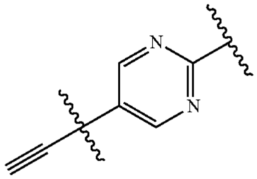
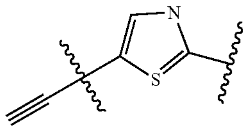
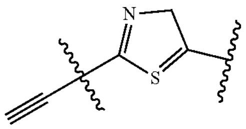
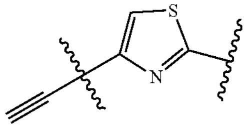
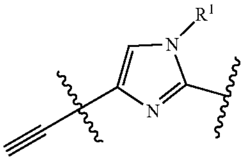
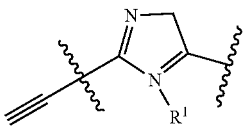
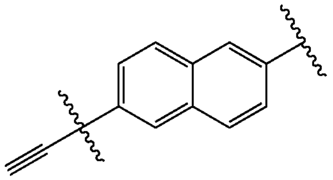
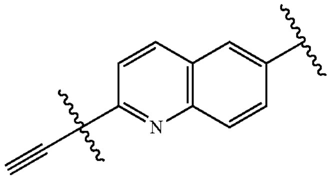
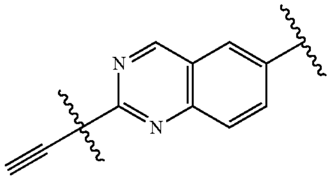
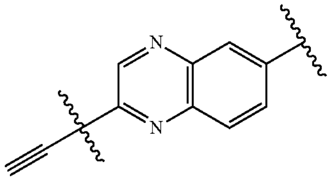
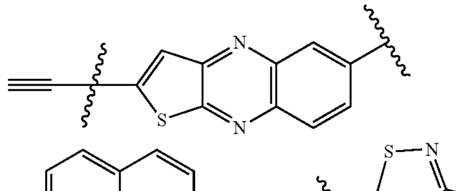
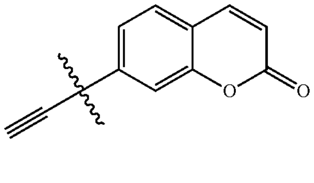
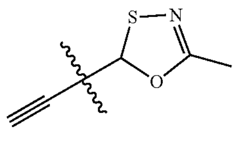

-continued

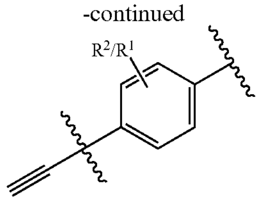

In an embodiment, $Ar_1$ is selected from a phenyl, pyridine, pyrimidine, thiophene, furan, benzofuran, thiazole and oxathiazole group.

In an embodiment, $Ar_1$ and $Ar_2$ may each be independently selected from a phenyl, pyridine, pyrimidine, thiophene, furan, benzofuran, thiazole and oxathiazole group.

In an embodiment, $Ar_1$ and $Ar_2$ may each be independently selected from a phenyl, thiophene, furan, benzofuran, thiazole and oxathiazole group.

In an embodiment, $Ar_1$ is a phenyl group.

In an embodiment, $Ar_1$ is a phenyl group and $Ar_2$ is selected from a phenyl, thiophene, furan, thiazole and oxathiazole group.

X is an electron deficient group. The term "electron deficient group" as used herein means a functional group that exhibits reduced electron density in comparison to the rest of the chemical structure of the molecule of formula I. As would be apparent to one skilled in the art, as well as exhibiting reduced electron density in comparison to the rest of the chemical structure of the molecule of formula I, the electron deficient group should not be toxic. This means that nitro and nitrile groups, for instance, would generally not be suitable.

According to the invention, X is selected from unsaturated esters, ketones, carboxylic acids, imidazolones, pyridines, oxazolones, oxazolidinones, barbituric acids, thiobarbituric acid, $—CH{=}CH—C({=}O)R^4$ in which $R^4$ is a $C_2$-$C_{10}$ alkyl, or an alkenyl, aryl or glycol group; $—CH{=}CH—C({=}O)R^5$, in which $R^5$ is a $C_2$-$C_{10}$ alkyl, or an alkenyl or aryl group, $—CF_3$, or $—NH_2$; $—(OCH_2CH_2OH)_n$ where n=1 to 6, or a nitrogen-containing heterocycle, optionally wherein the N-containing heterocycle comprises 5 or 6 ring-members.

As used herein, the term "alkyl" refers to a fully saturated, branched, unbranched or cyclic hydrocarbon moiety, i.e. primary, secondary, or tertiary, alkyl or, where appropriate, cycloalkyl or alkyl substituted by cycloalkyl. Where not otherwise indicated, an alkyl group comprises 1 to 10 carbon atoms, preferably 1 to 6 carbon atoms, or more preferably 1 to 4 carbon atoms. Representative examples of alkyl groups include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkenyl" refers to an unsaturated alkyl group having at least one double bond.

The term "halogen" or "halo" as used herein, means fluoro, chloro, bromo, or iodo.

The term "aryl" refers to an aromatic monocyclic or polycyclic hydrocarbon ring system consisting only of hydrogen and carbon and containing from 6 to 19 carbon atoms, preferably from 6 to 10 carbon atoms, wherein the ring system may be partially saturated. Aryl groups include, but are not limited to, groups such as fluorophenyl, phenyl, indenyl and naphthyl.

The term "aryl" includes aryl radicals optionally substituted by one or more substituents selected from the group consisting of alkyl, alkenyl, alkynyl, halo, haloalkyl, cyano, nitro, amino, amidine, aryl, aralkyl, cycloalkyl, heterocyclyl, heteroaryl or heteroarylalkyl. Preferred alkyl groups are optionally substituted phenyl or naphthyl groups.

In an embodiment of the invention, $R^1$ and $R^2$ form part of heterocyclic group Y. In this embodiment, heterocyclic group Y may be, for example, selected from:

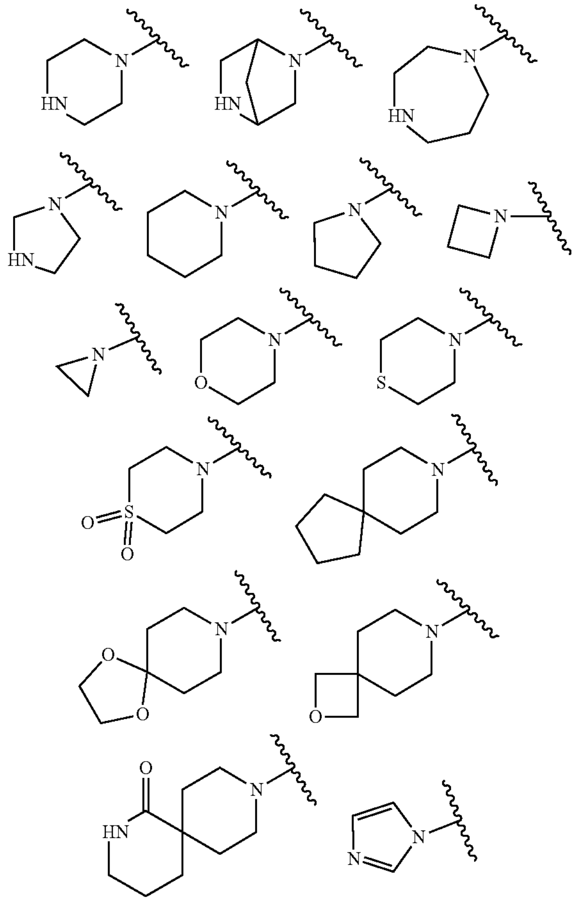

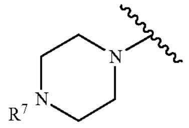

or

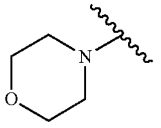

$R^7$ may be a $C_1$-$C_{10}$ alkyl group, $-COCH_3$, $-C(O)(CH_2)_nC(O)R^8$, $-C(O)(CH_2)_mO(CH_2)_mC(O)R^8$, $-C(O)$(CH2)nCH(CH3)C(O)$R^8$, $=S(O)_2(CH_2)_nC(=O)R^8$, $-S^+(O^-)(CH_2)_nC(=O)R^8$ or $-(CH_2)_nPPh_3{}^+Br^-$, in which $R^8$ is $-OH$ or $-NHOH$, n is an integer from 1 to 8, and m is an integer from 1 to 4.

Alternatively, $R^1$ may be H or an alkyl group comprising from 1 to 10 carbon atoms, optionally substituted with one or more N atoms, and $R^2$ may be selected from an alkyl group comprising from 1 to 10 carbon atoms, optionally substituted with one or more N atoms, $-(CH_2)_nR^3$, $-(CH_2)_nNHR^3$ and $(CH_2)_2(COCH_2)_nR^3$ in which n is an integer from 1 to 10 and $R^3$ is $-NH_2$, $-OH$, $-SO_2PhCH_3$, or $-COOH$, or $R^2$ may be $-COCH_3$, $-C(O)(CH_2)_nC(O)R^8$, $-C(O)(CH_2)_mO(CH_2)_mC(O)R^8$, $-C(O)(CH_2)_nCH(CH_3)C(O)R^8$, $-S(O)_2(CH_2)_nC(=O)R^8$, $-S^+(O^-)(CH_2)_nC(=O)R^8$ or $-(CH_2)_nPPh_3{}^+Br^-$, in which $R^8$ is $-OH$ or $-NHOH$, n is an integer from 1 to 8, and m is an integer from 1 to 4. In this embodiment, preferably $R^1$ is H or an alkyl group comprising from 1 to 10 carbon atoms, and $R^2$ is $(CH_2)_nR^3$, $-(CH_2)_nNHR^3$ or $(CH_2)_2(COCH_2)_nR^3$ in which n is an integer from 1 to 10 and $R^3$ is $-NH_2$, $-OH$, $-SO_2PhCH_3$ or $-COOH$.

In an embodiment, X is selected from: $-CH=CH-C(=O)R^4$ in which $R^4$ is a $C_2$-$C_{10}$alkyl, alkenyl, aryl or glycol group; $-CH=CH-C(=O)R^5$, in which $R^5$ is a $C_2$-$C_{10}$ alkyl, alkenyl or aryl group, $-CF_3$, or $NH_2$; $-(OCH_2CH_2OH)_n$ where n=1 to 6, or a nitrogen-containing heterocycle, optionally wherein the N-containing heterocycle comprises 5 or 6 ring-members.

When X is a N-containing heterocycle, it may be selected from:

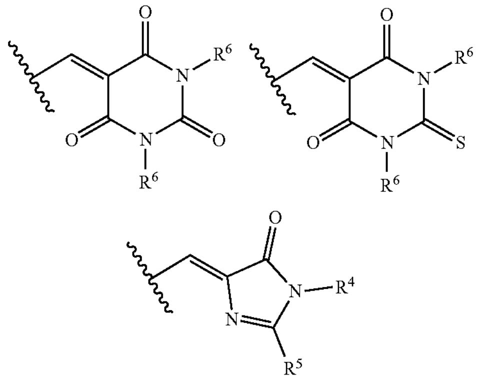

In which $R^4$ and $R^5$ are as defined above, and $R^6$ is H or alkyl.

In an embodiment, X is selected from:

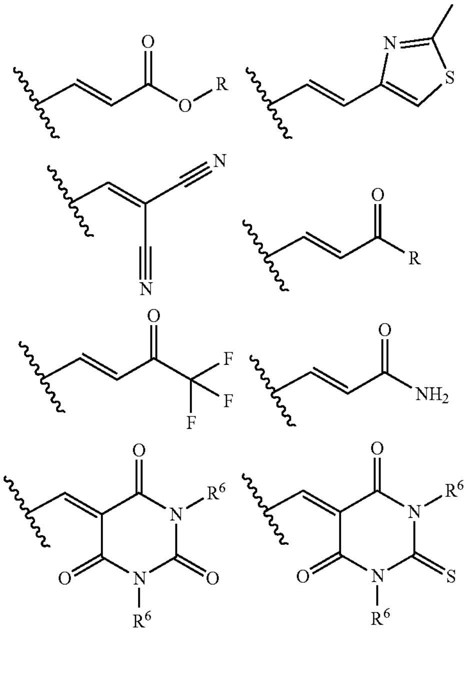

-continued

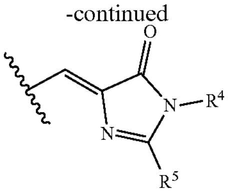

In the compound of formula I, for those embodiments in which $Ar_1$ is phenyl, and $R^1$ and $R^2$ form part of a heterocyclic group Y, the N of the heterocyclic group is in a para position with respect to the acetylene group of the compound of formula I. In an embodiment in which $Ar_1$ is phenyl, and $R^1$ and $R^2$ form part of a heterocyclic group Y, the N of the heterocyclic group attached to $Ar_1$ is not in an ortho position with respect to the acetylene group of the compound of formula I. This means that the compound of formula I is not, for instance:

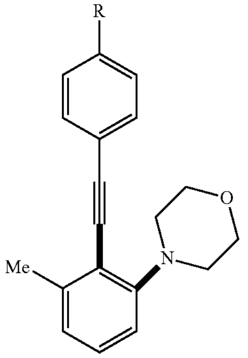

In an embodiment, the compound of formula I is selected from:

6

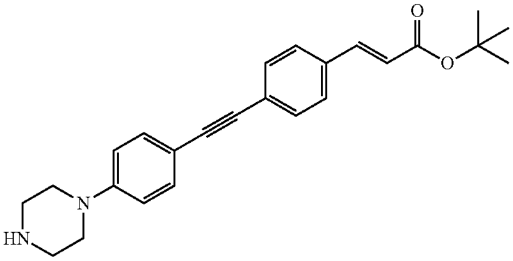

7

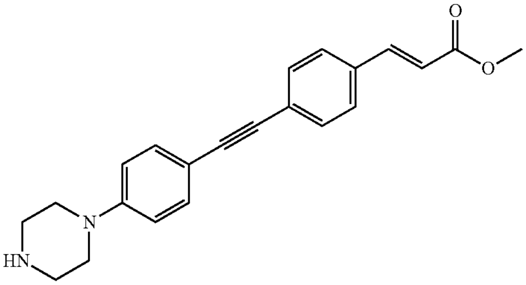

12

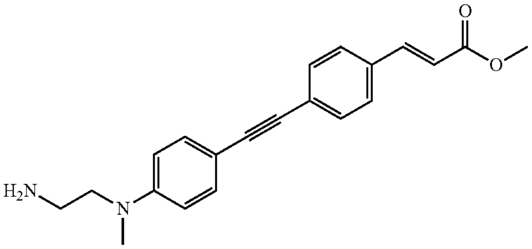

13

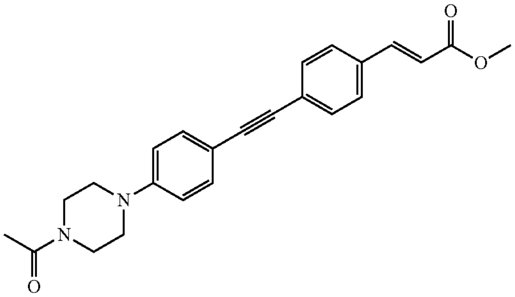

14

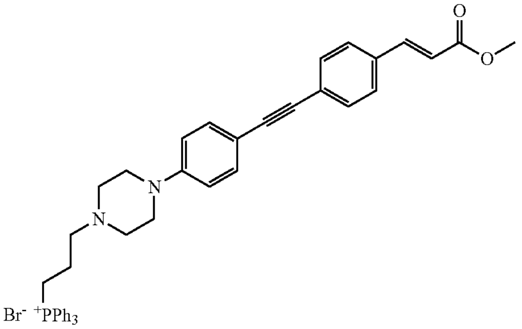

-continued
15
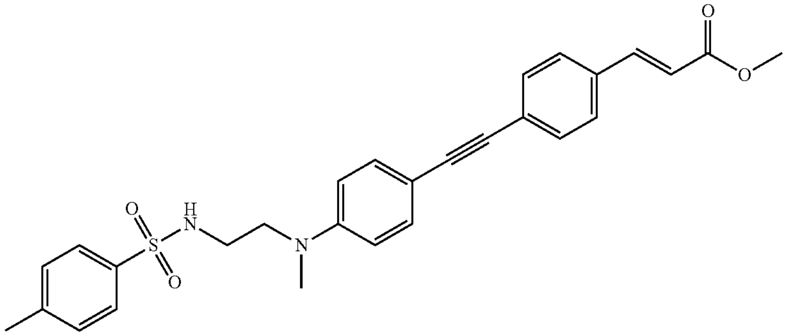
19
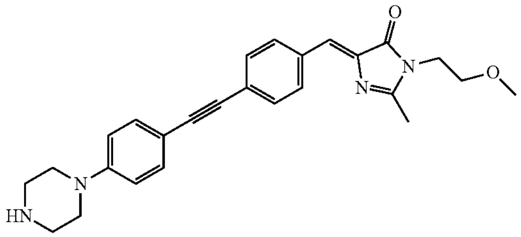
23
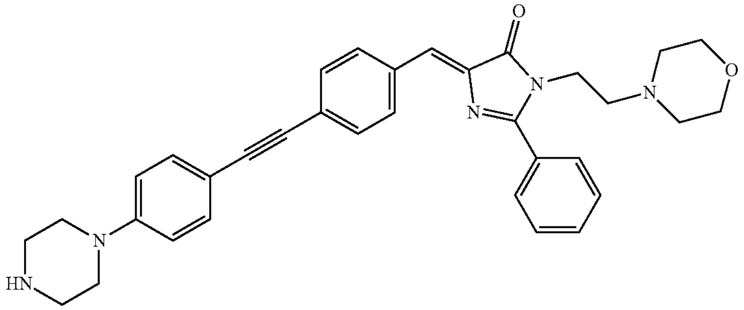
27
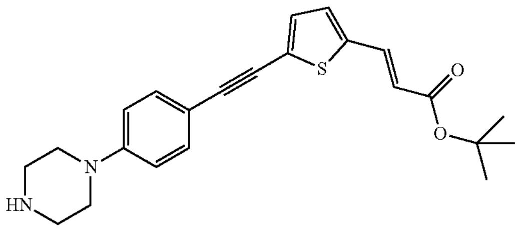
30
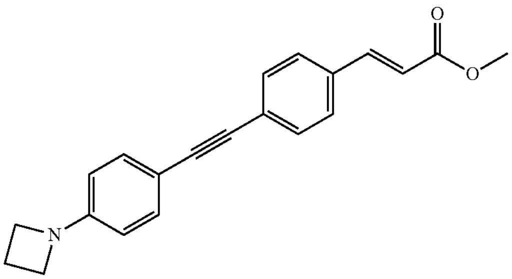
34
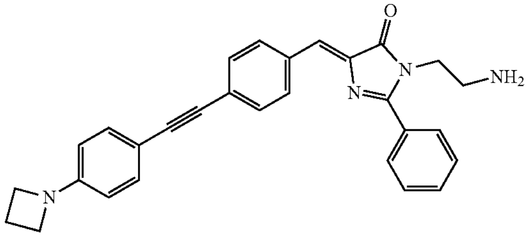
43
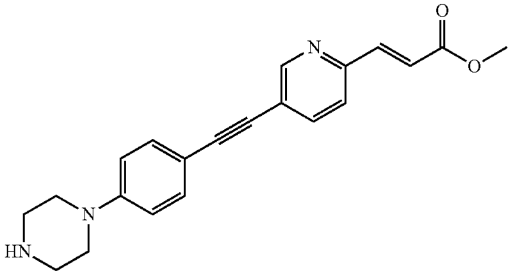

-continued
46
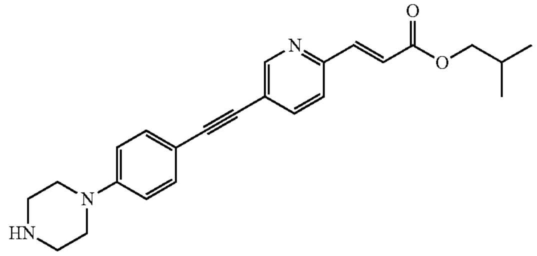
51
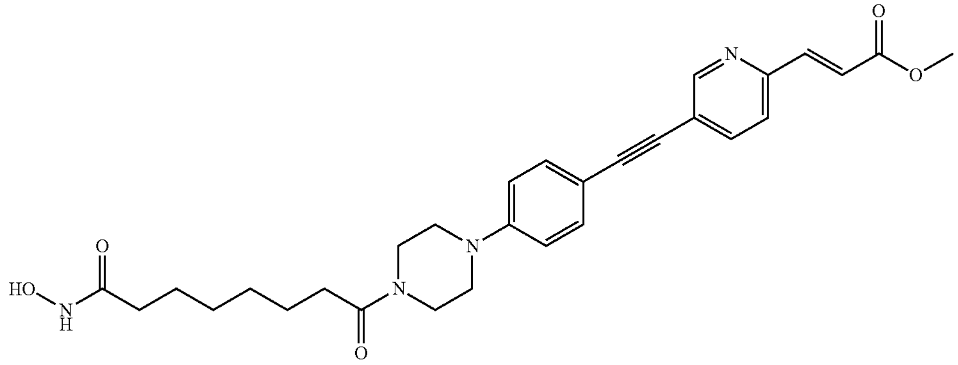
55
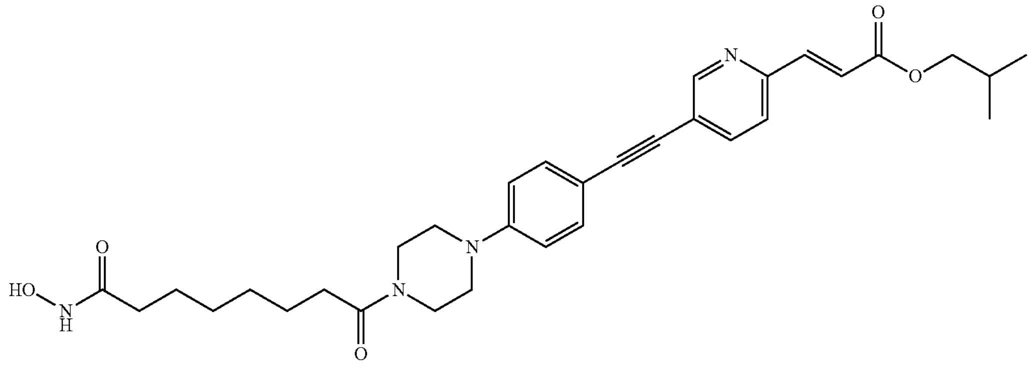
57
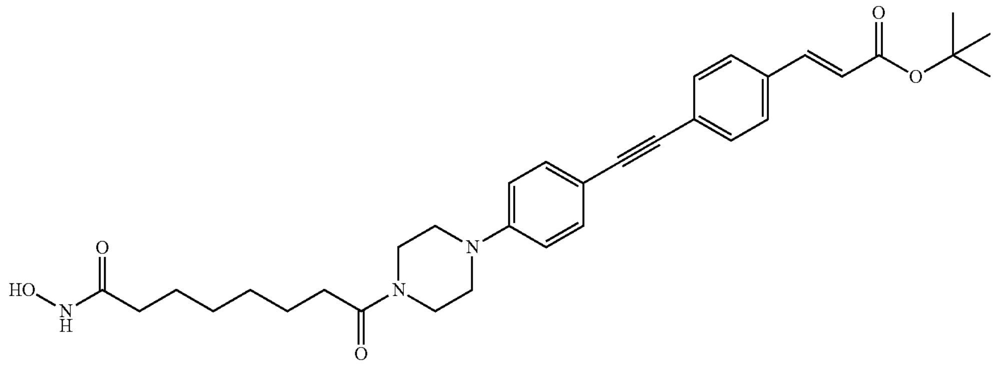

-continued
59
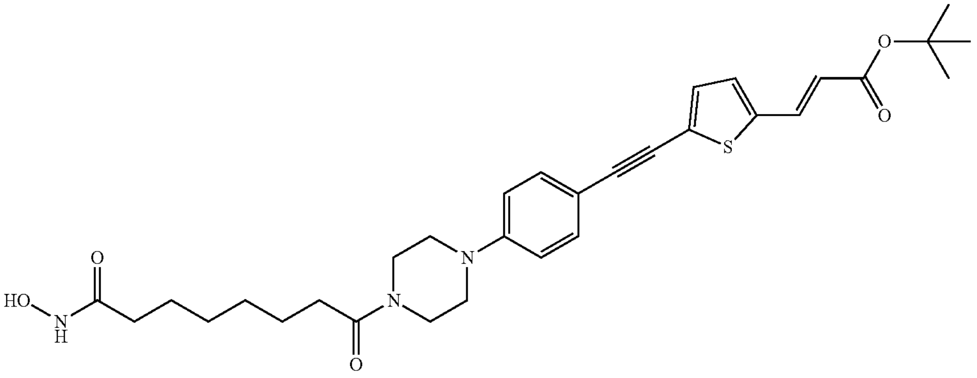
62
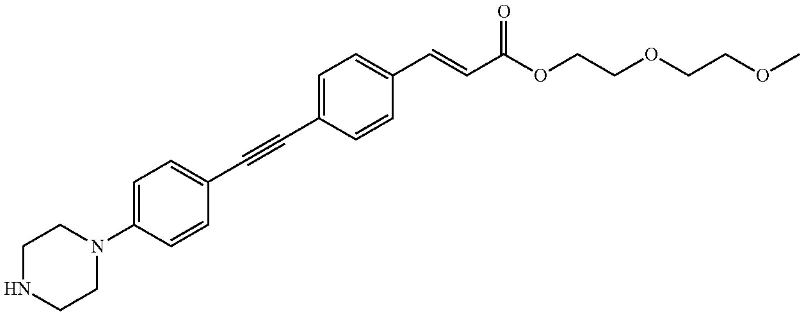
64
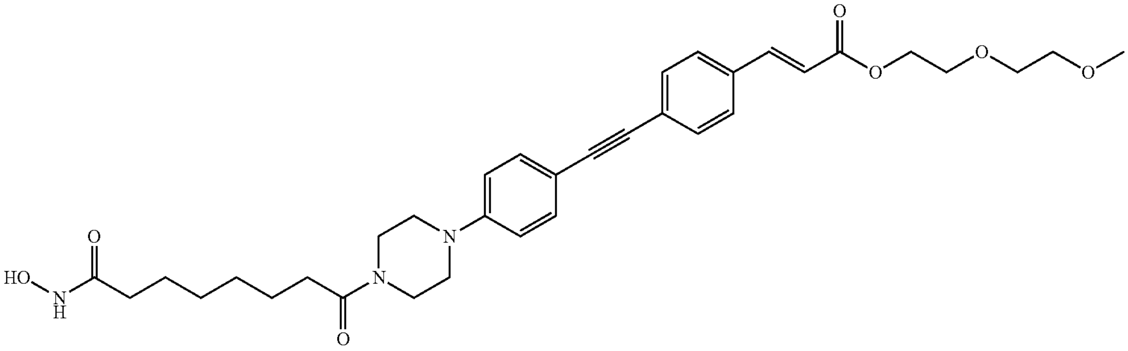
69
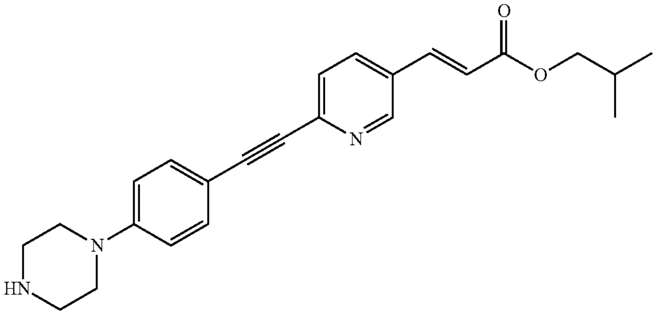

-continued

71

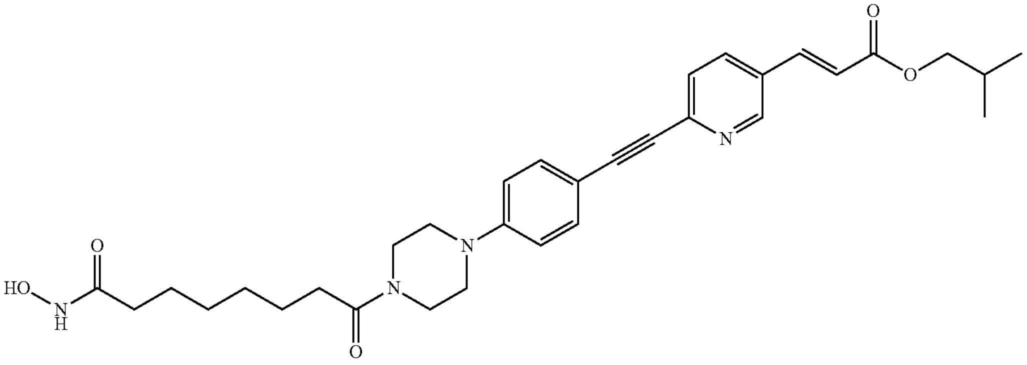

73

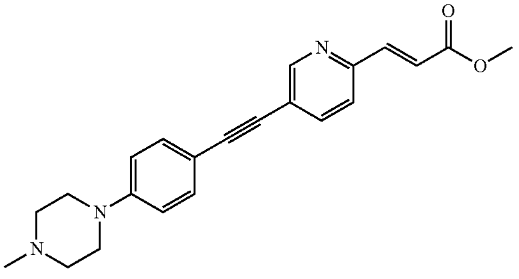

84

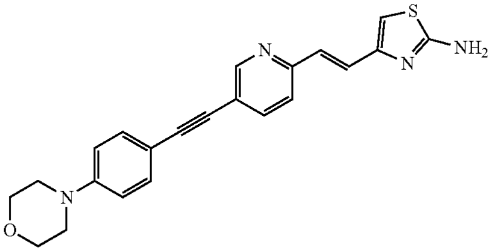

In an embodiment, the compound of formula I is compound 6, compound 7, compound 43, compound 51, compound 55, compound 57, compound 59, compound 64, compound 69, or compound 71

In an embodiment, the compound of formula I is compound 6, compound 7, compound 43, or compound 69.

The compounds according to the present invention are inherently fluorescent. According to an aspect of the present invention, there is provided a compound of formula I for use in fluorescent imaging.

The flexible chemistry of the compounds of formula I advantageously allows for selective targeting of cell types and/or cell localisation, making the compounds of formula I powerful tools in biological imaging. For instance, the compounds of the invention can be readily conjugated to a range of targeting biomolecules, to provide invaluable information concerning cellular uptake and localisation via fluorescence imaging techniques.

Due to the modular nature of the compound structures, compound construction of formula I is feasible through modification by different functional groups enabling chromophoric extension in order to approach, or reach, the near-infrared region (NIR). Fluorescence in the near-infrared region (1,000-1,700 nm) is particularly useful in biological and biomedical imaging due to deep penetration, high spatial resolution and low biofluorescence (Stolik et al. J. Photochem. Photobiol. B. 57 (20000), 90-93).

According to an aspect of the present invention, there is provided a compound of formula I for use in Raman imaging.

Aspects of the present invention relate to the use of a compound of formula I in Raman imaging.

In particular, the internal acetylene function of the compounds of formula I gives rise to unique vibrational frequencies in the 'cell-silent' Raman window (1800-2600 $cm^{-1}$), i.e. the region in which no endogenous molecules vibrate, allowing the compounds to be used for imaging specific molecules of interest in biological environments using Raman-based techniques.

In aspects, the compounds are dual-mode imaging agents.

Aspects of the present invention relate to use of the compounds in combined fluorescence and Raman imaging techniques, for instanced by superimposing fluorescence, to provide environmental information, and Raman, to provide quantitative mapping, to generate a powerful tool for imaging complex biological systems.

The invention also relates to methods of monitoring cellular development, such as cell differentiation or apoptosis. In embodiments, such a method can comprise administering an effective amount of the compound of formula I and detecting the fluorescence emitted. Alternatively, methods of monitoring cellular development, such as cell differentiation or apoptosis, can comprise imaging the distribution of a compound of formula I by detecting the Raman scattering signal stimulated by techniques that include, but are not limited to, coherent anti-Stokes Raman scattering (CARS) and stimulated Raman scattering (SRS).

Accordingly, in an aspect of the present invention there is provided a probe comprising a compound of formula I.

The flexible chemistry of the compounds of formula I advantageously allows for selective targeting of cell types and/or cell localisation, making the compounds of formula I powerful tools in biological imaging.

In aspects, the invention relates to the modulation of the properties of the compounds of formula I to incorporate targeting functions for cell-localisation. For instance, reactive amine groups of the compounds can undergo one step acylation, alkylation or sulfonylation reactions to introduce targeting motifs for subcellular localisation, such as triphenylphosphonium cations (localisation to the mitochondrial matrix), and tosyl sulphonamide groups (localisation to the endoplasmic reticulum (ER)).

The method also relates to deactivated derivatives of the compound.

As would be understood by a person skilled in the art, compounds that incorporate a reactive functional group, such as an amine; hydroxyl or carboxylic acid group, for example, will often be protected as a deactivated derivative, i.e. an amide, ether or ester, for storage. Activation of these compounds for further reaction or conjugation involves removal of the protecting group for instance by treatment with strongly acidic solutions (amide to amine), strong Lewis acids (ether to hydroxyl) and treatment with strong basic aqueous solutions (ester to carboxylic acid). Alternatively, reactive amine groups, for example, can be further derivatised to access functional groups that activates them to provide orthogonal reactivity for conjugation reactions not accessible by the parent compound e.g. amine conversion to acrylamide for reaction with thiols, amine reaction with cyclic anhydride to give carboxylic acid for reaction with other amines or hydroxyls, amine conversion to azidoacetamide for azide/alkyne cycloaddition reactions.

In aspects, the invention relates to both the protected and deprotected compounds of formula I.

According to an aspect of the invention there is provided a conjugate comprising a compound of formula I and a targeting or active agent. The targeting or active agent can be, for instance, a reactive group, such as a photoaffinity label, a small molecule drug such as anti-cancer agents including vorinostat, methotrexate and fulvestrant, a biomolecule such as a protein or peptide including those containing cell adhesion sequences such as RGD (tripeptide Arg-Gly-Asp), a carbohydrate such as glucose or polysaccharide sucrose, or a biologic such as an aptamer, affimer or antibody.

For example, the targeting or active agent could include a photo-reactive function which works at a different wavelength to the fluorophoric compound of formula I, to enable release of the compound via photoreactive linker, or to activate a photoaffinity label to tag a target protein/receptor or enzyme. Suitable photoaffinity labels include diaziridine (diazirine) which can be readily attached to an amine group of the compound of formula I.

The targeting or active agent may be coupled to the compounds of formula I covalently, for example by amide or ester or ether linkages. The technique of 'click-chemistry', i.e. joining substrates to biomolecules may be also used to prepare the conjugates of the invention. The targeting or active agent may be attached to the compound of formula I using a linker, such as unsymmetric (bifunctional) PEG or other spacer groups. Suitable functional group chemistries which can be employed include carboxylic acid for amide formation, alcohol and carboxylic acid forester formation, alkyl electrophile and alcohol for ether formation and alkylazide and acetylene for Click-reaction.

In an embodiment, the conjugate comprises a compound of formula:

6

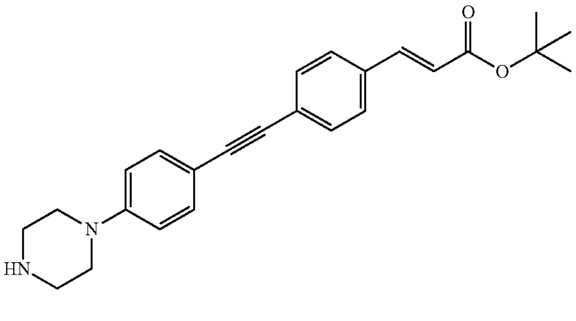

7

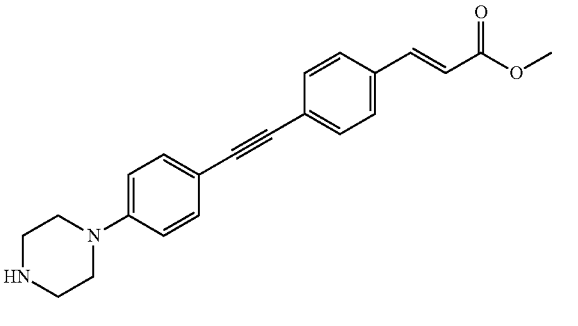

12

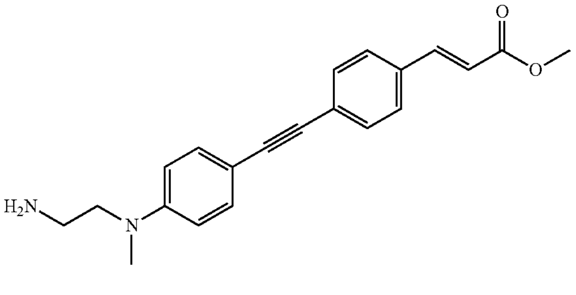

13

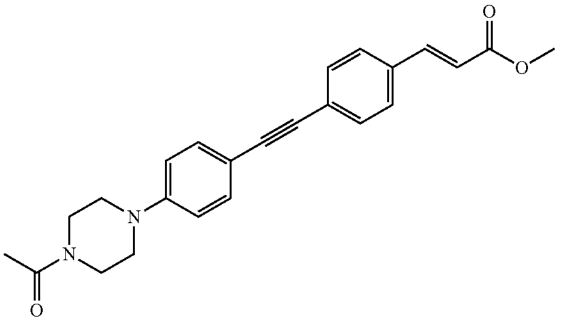

-continued
14
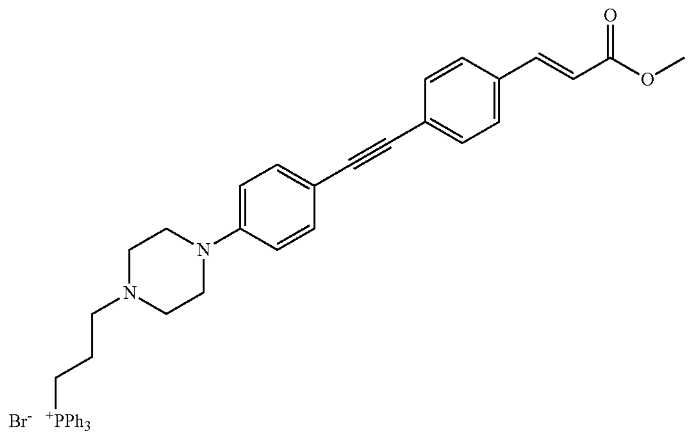
15
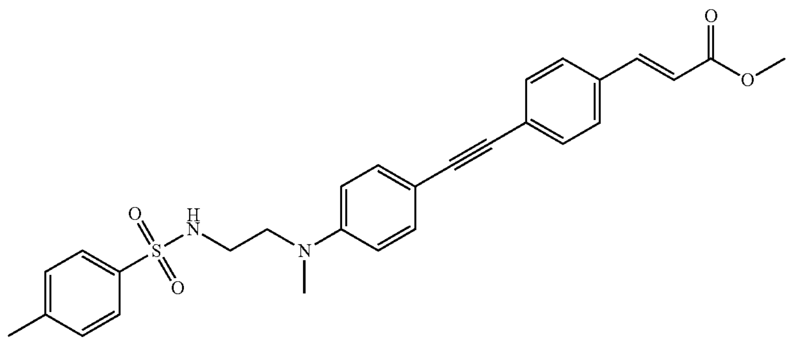
19
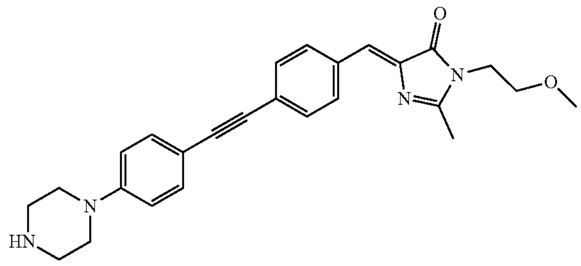
23
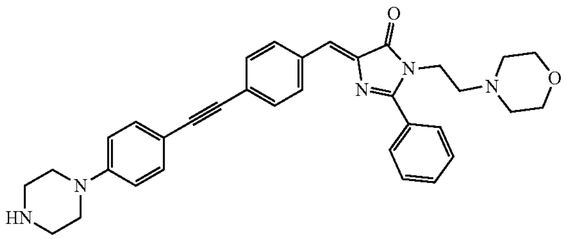
27
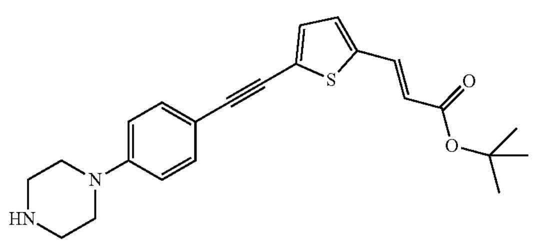
30
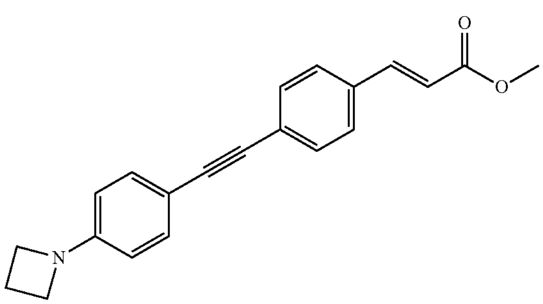

-continued
34
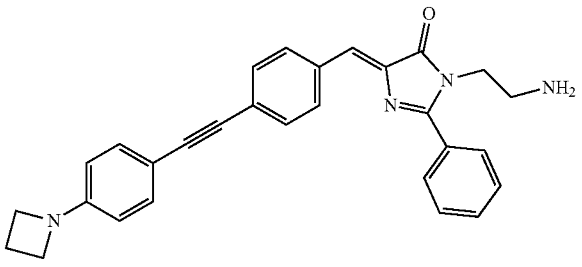
43
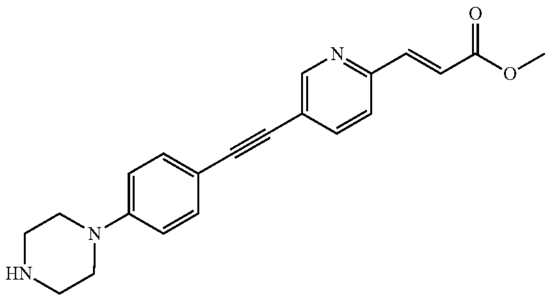
46
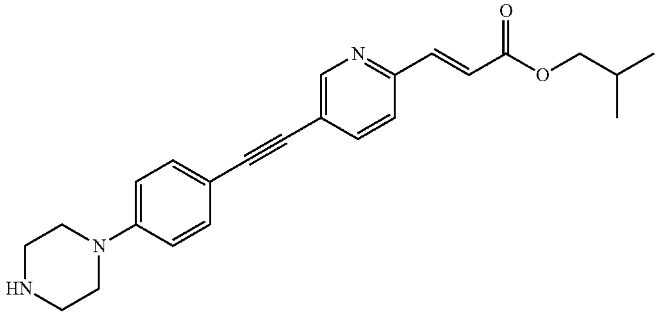
51
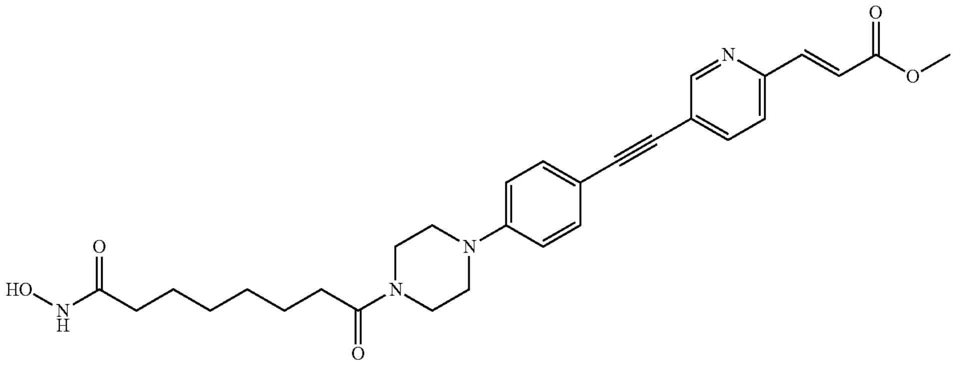
55
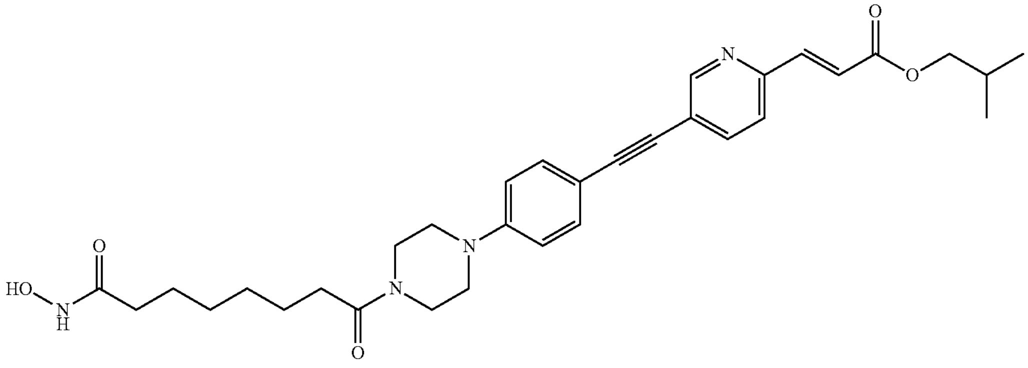

-continued
57
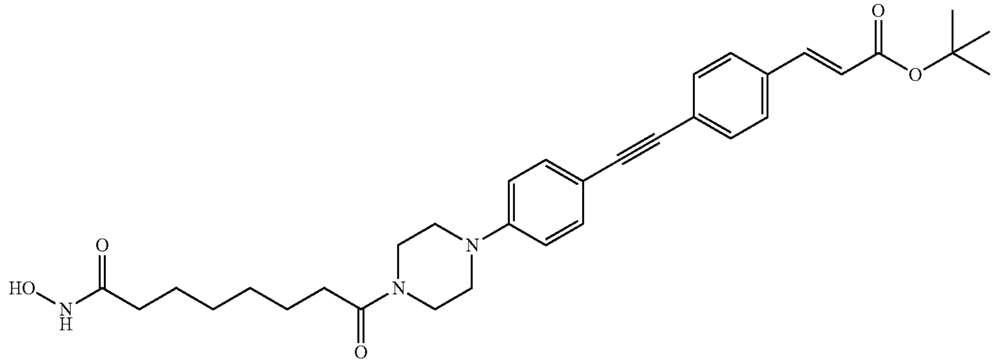
59
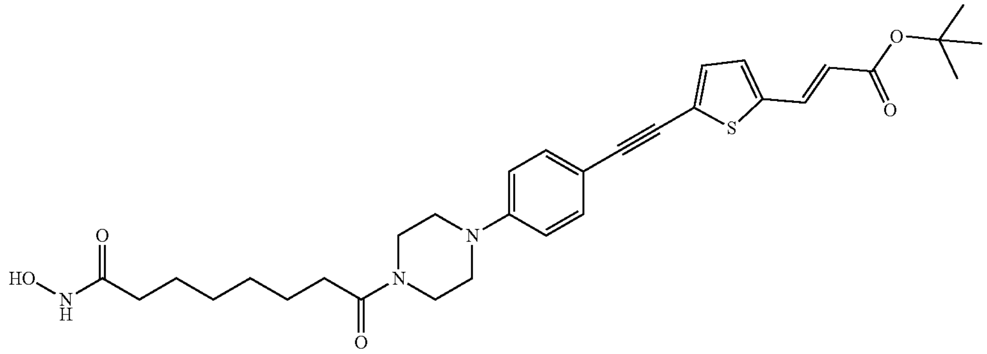
62
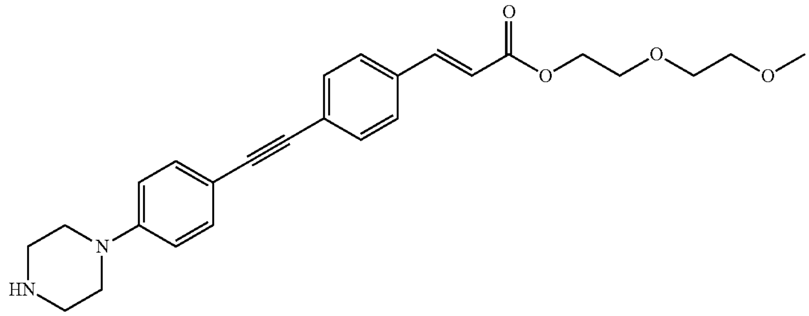
64
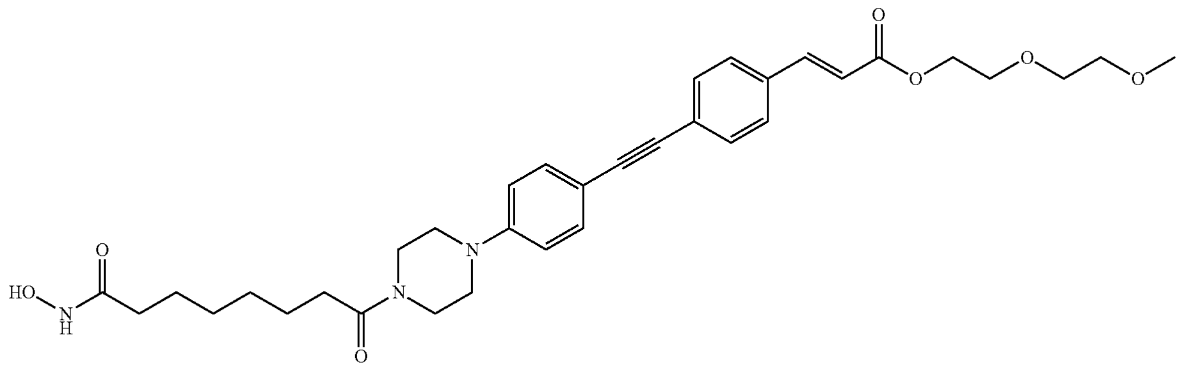

-continued

69

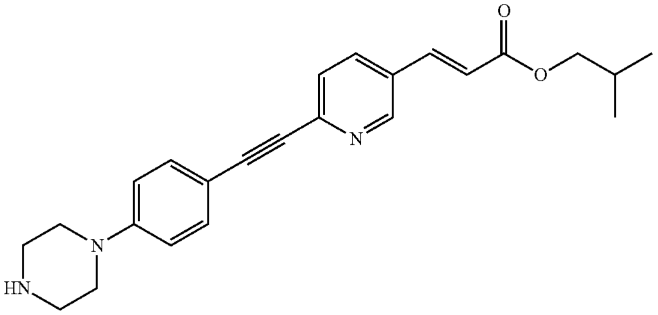

71

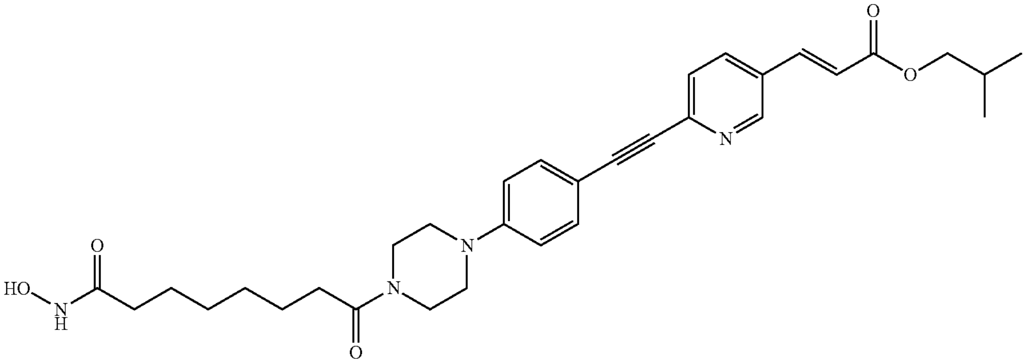

73

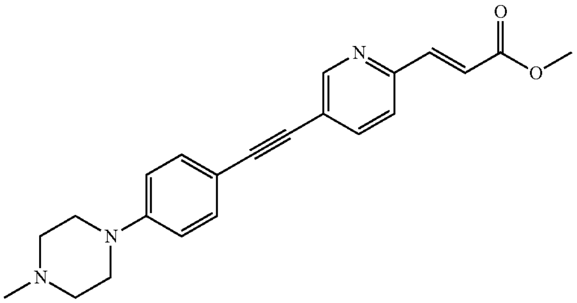

84

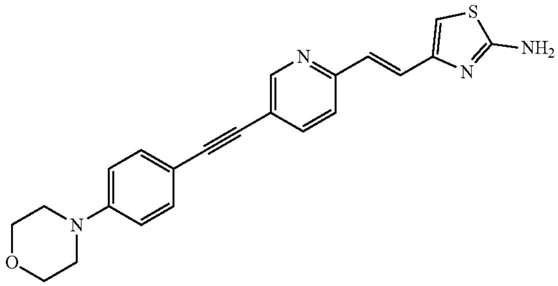

The targeting or active agent may be a small molecule drug, such as an anti-cancer drug.

In an embodiment, the conjugate comprises a compound of formula 6, of formula 7, of formula 43, of formula 51, of formula 55, of formula 57, of formula 59, of formula 64, of formula 69, or of formula 71.

In an embodiment, the conjugate comprises a compound of formula 6, formula 7, formula 43 or formula 69:

Compound 6

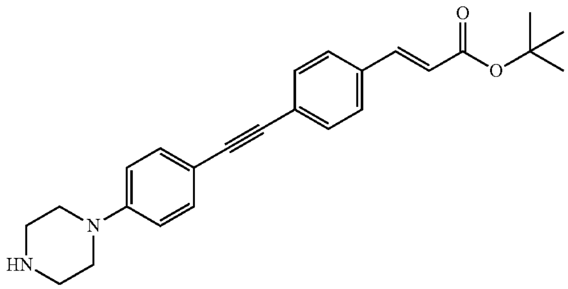

-continued

Compound 7

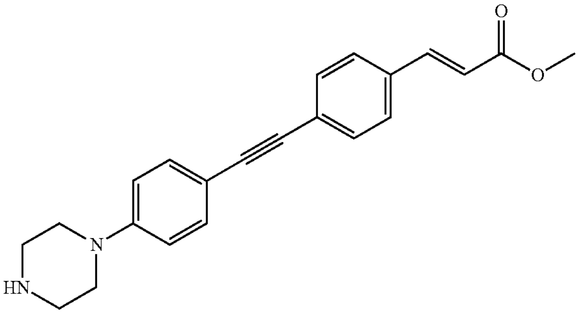

-continued

Compound 43

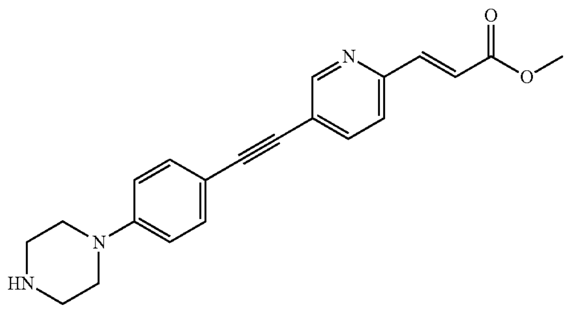

Compound 69

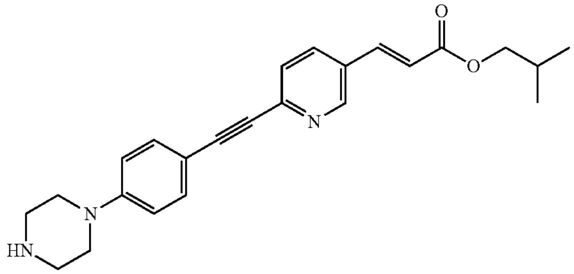

In an embodiment, the conjugate comprises a compound of formula 6 and a small molecule drug. In an embodiment, the conjugate comprises a compound of formula 6 and an anti-cancer drug. In an embodiment, the conjugate comprises a compound of formula 6 and vorinostat or an analogue thereof.

In an embodiment, the conjugate comprises a compound of formula 7 and a small molecule drug. In an embodiment, the conjugate comprises a compound of formula 7 and an anti-cancer drug. In an embodiment, the conjugate comprises a compound of formula 7 and vorinostat or an analogue thereof.

The invention also relates to the use of these conjugates in imaging, therapeutic and non-therapeutic applications.

In aspects, the invention relates to the use of the compounds of formula I in the generation of reactive oxygen species (ROS) when said compound is activated by light.

Triplet state photosensitizers (PS) typically comprise a light-harvesting region, which is responsible for the dual-functionality of light-harvesting and intersystem crossing, where electrons in the single state non-radiatively pass to the triplet state. Quenching of the triplet-excited state can result in the formation of reactive oxygen species (ROS), radicals from ground state molecular oxygen, or direct chemical reactions with surrounding molecules.

Localised ROS production is an immune defence strategy employed in both animal and plant systems in response to pathogen attack. Within animal, plant, fungal and bacterial cells, the ROS elicit a variety of modulatory effects depending on the rate and extent of their production; at high concentrations apoptosis is observed, while at low concentrations a stimulatory response is often observed (Guo et al. Stem Cells Dev. 2010, 19, 1321-1331).

Photodynamic therapy (PDT) exploits the ability of photosensitizers to generate ROS, typically to destroy cancer cells, pathogenic microbes and/or unwanted tissue by apoptosis. Typically, the photosensitizing compound is excited near/inside a particular target tissue or condition (e.g. microbial infections, neoplasias, tumours etc) causing the generation of large quantities of ROS and subsequent destruction of that tissue. At low levels of ROS, cell proliferation can be triggered, leading to applications in wound healing or more general tissue regeneration therapies.

Thus, PDT relies on the targeting of the photosensitive compound to accumulate in the desired location, such as the cells of the diseased tissue, and localised light delivery to activate ROS generation. While compounds for use in PDT are known, they often suffer from a variety of disadvantages, including small absorbance peaks, causing difficulties in light activation, particularly for bulky tumours where light penetration can be difficult to achieve; long biological half-lives, leading to skin photosensitivity for extended periods post-treatment; poor pharmacological properties such as poor aqueous solubility; and poor targeting ability (i.e. poor ability to target and accumulate in specific tissues or cells, leading to significant off-target damage).

Advantageously, the compounds of the present invention are biologically inert in the unactivated state, but generate ROS when irradiated with low to medium energy short-wavelength visible light.

The compounds of formula I can therefore be used to generate reactive oxygen species (ROS) and thereby control cellular development, i.e. to control proliferation, differentiation and apoptosis of cells, leading to a variety of therapeutic and non-therapeutic uses. The compounds of formula I are particularly advantageous for use in applications mediated by the control of ROS, as they demonstrate efficient targeting, which can lead to fewer off-target effects. They can also be tuned to different cell types, allowing selective targeting effects to be achieved.

In aspects, therefore, the invention relates to the use of the compounds or conjugates of the invention in photodynamic therapy (PDT).

The generation of ROS can be controlled based on the therapeutic need, for instance, to induce apoptosis for the ablation of cells, to cause proliferation in wound healing, or by a combination of these. In an exemplary embodiment, for instance in wound care, high levels of ROS could initially be triggered, leading to apoptosis of bacterial and/or fungal cells, followed by low levels of ROS to aid in skin regeneration.

In an aspect of the invention there is provided a method of treating a patient with photodynamic therapy (PDT), the method comprising the administration of a compound of formula I or conjugate thereof, and activating the compound of formula I to generate ROS.

In another aspect of the present invention there is provided the use of a compound of formula I, or a conjugate thereof, in the manufacture of a medicament for use in the treatment of a disease or condition that benefits from the control of cell proliferation, differentiation or apoptosis.

In another aspect of the present invention there is provided a method of treatment of a patient with a disease or condition that benefits from the control of cell proliferation, differentiation or apoptosis, the method comprising administering to a patient a therapeutically effective amount of a compound of formula I or a conjugate thereof.

Diseases or conditions that benefit from the control of cell proliferation, differentiation or apoptosis include, for example, cancers, e.g. neural neoplasm, skin disorders such as acne, and skin wounds such as burns, diabetic foot ulcers, UV damage and aging skin.

The compounds of formula I may act as chemotherapeutic or chemopreventative agents due to their ability control cellular development, i.e. to control proliferation, differentiation and apoptosis in normal and tumour cells. In particular, the compounds of formula I may modulate the growth, differentiation, and apoptosis of normal, premalignant and malignant cells in vitro and in vivo.

In embodiments of the invention, the compound may act as a chemotherapeutic or chemopreventative agent in the treatment or prevention of precancerous or cancerous conditions including those of the skin, oral cavity, larynx, lung, bladder, vulva, breast, kidney, liver, prostate, eye or digestive tract etc.

The compound may act as a chemotherapeutic or chemopreventative agent in the treatment or prevention of basal cell carcinomas, squamous cell carcinomas, including those of the head and neck, and bladder tumours.

The compound may act as a chemotherapeutic or chemopreventative agent in the treatment or prevention of leukaemia, such as myelogenous leukaemia, in particular acute promyelocyte leukaemia.

The compounds of formula I may act to promote cell proliferation, for example skin or neural cell proliferation, and to assist in wound healing. The compounds of formula I may be used in promoting tissue health and development, in particular in promoting the health and development of the skin, bone, nerves, teeth, hair and/or mucous membranes of the human or animal body. The compounds of the invention may be used in the prevention or treatment of the signs of ageing (in particular wrinkles and age spots), skin conditions such as acne (especially severe and/or recalcitrant acne), psoriasis, stretch marks, keratosis pilaris, emphysema and baldness.

In embodiments of the invention, the conjugates of formula I can be used in PDT. For instance, embodiments of the invention relate to a conjugate of formula I with a small molecule therapeutic, such as an anti-cancer drug. Due to the relatively small nature of the compounds of formula I compared with previous fluorophores, the anti-cancer drug can exhibit unchanged targeting, i.e. as demonstrated in vorinostat, the bioconjugate behaves as though the compound of formula I was not attached, allowing it to retain its cytotoxic effects. Therefore, the conjugate can be delivered to the site of interest, where the drug can perform its usual function, before irradiating the conjugate with UV light, leading to the controlled generation of ROS. In the context of an anti-cancer drug, for instance, the cell-killing effect of the drug could be supplemented by ROS-mediated apoptosis, i.e. the anti-cancer drug could cause initial death of cancer cells, with apoptosis then being triggered to kill remaining cells.

In another aspect there is provided a pharmaceutical composition comprising a compound of formula I, or a conjugate thereof, as defined herein, optionally in conjunction with one or more pharmaceutically acceptable excipients, diluents or carriers, for use in the treatment or alleviation of a disease or condition benefits from the control of cell differentiation or apoptosis. The composition may optionally comprise one or more additional therapeutic agents.

In embodiments, the pharmaceutical composition may comprise a compound of formula I conjugated to a therapeutic agent, such as a small molecule drug like an anti-cancer drug.

In embodiments, the pharmaceutical composition may comprise a compound of formula I conjugated to vorinostat, or an analogue thereof.

The conjugate comprising a compound of formula 6 and vorinostat or an analogue thereof exhibits an inherent cytotoxic activity from the hydroxamic acid of the vorinostat that can be supplemented and augmented by application of UV, 405 nm or two-photon 800 nm light to induce an additional photoactivated cell-killing effect.

The term "therapeutically effective" amount or "effective amount" refers to the quantity of the compound or composition of the present invention which is effective in producing the desired therapeutic, ameliorative, inhibitory or preventative effect.

The dosage of the compound or conjugate to be administered to the human or animal body will be dependent on factors such as the intended use, and the mode of administration, as would be recognised by a person skilled in the art.

The term "pharmaceutical composition" refers to a composition suitable for administration to a patient. Thus, the term "pharmaceutical composition" refers to compositions which comprise the compound of the invention, or conjugates or mixtures thereof, or salts, solvates, prodrugs, isomers or tautomers thereof, optionally in conjunction with one or more pharmaceutically acceptable excipients, carriers or diluents. The term "pharmaceutical composition" is also intended to encompass both the bulk composition (i.e. in a form that has not yet been formed into individual dosage units) and individual dosage units. Such individual dosage units include tablets, pills, caplets, ampoules and the like.

Those skilled in the art will recognise those instances in which the compounds of the invention may be converted into prodrugs and/or solvates. The term "prodrug" refers to a compound (e.g. a drug precursor) that is transformed in vivo to yield a compound of the invention or a pharmaceutically acceptable salt, hydrate or solvate of the compound. The transformation may occur by various mechanisms (e.g. by metabolic or chemical processes) such as, for example, through hydrolysis in blood.

The compounds of the invention may be unsolvated or may be solvated with pharmaceutically acceptable solvents such as water, ethanol, and the like. For instance, it will be understood that a solvate may be capable of isolation, for example when one or more solvent molecules are incorporated in the crystal lattice of the crystalline solid. "Solvate" encompasses both solution-phase and isolatable solvates. Suitable solvates include, but are not limited to, ethanolates, methanolates, hydrates, and the like.

Compounds for use in the invention include salts thereof, and reference to a compound of the invention is intended to include reference to salts thereof, unless otherwise stated. Suitable salts include for instance, acidic salts formed with inorganic and/or organic acids, basic salts formed with inorganic and/or organic bases, as well as zwitterions ("inner salts") which may be formed and are included within the term "salt(s)" as used herein. Pharmaceutically acceptable (i.e., non-toxic, physiologically acceptable) salts are preferred, although other salts may be useful in certain circumstances. Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates,) and the like. Exemplary basic salts which may be useful include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g.

methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), arylalkyl halides (e.g. benzyl and phenethyl bromides), and others.

Compounds for use in the invention include pharmaceutically acceptable esters thereof, and may include carboxylic acid esters, obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$ alkyl, or $C_{1-4}$ alkoxy or amino); (2) sulfonate esters, such as alkyl- or aralkylsulfonyl (for example, methanesulfonyl); (3) amino acid esters (for example, L-valyl or L-isoleucyl); (4)phosphonate esters; and (5) mono-, di- or triphosphate esters.

Polymorphic forms of the compounds of the invention, and of the salts, solvates, esters and prodrugs of the compounds of the invention, are intended to be included in the present invention.

Suitable dosages for administering compounds of the invention to patients may be determined by those skilled in the art, e.g. by an attending physician, pharmacist, or other skilled worker and may vary according to factors such as patient weight, health, age, frequency of administration, mode of administration, the presence of any other active ingredients, and the condition for which the compounds are being administered.

Examples of excipients, diluents and carriers include buffers, as well as fillers and extenders such as starch, cellulose, sugars, mannitol and silicic derivatives. Binding agents may also be included. Adjuvants may also be included.

Optionally the compound of formula I may be administered in combination with one or more additional therapeutic agents. When used in combination with one or more additional therapeutic agents, the compounds of the invention may be administered together or sequentially.

The compositions may be administered by a variety of routes including oral, parenteral (including subcutaneous, intravenous, intramuscular and intraperitoneal), rectal, dermal, transdermal, intrathoracic, intrapulmonary, mucosal, intraocular and intranasal routes.

Suitable dosage forms will be recognised by one skilled in the art and include, among others, tablets, capsules, solutions, suspensions, powders, aerosols, ampules, pre-filled syringes, small volume infusion containers or multi-dose containers, creams, milks, gels, dispersions, microemulsions, lotions, impregnated pads, ointments, eye drops, nose drops, lozenges etc.

The compounds of formula I and conjugates thereof can be used to control the generation of ROS in non-therapeutic applications. Advantageously, the compounds of formula I have been shown to penetrate into other cell types, such as plant cells, leading to a variety of other uses, such as in targeted herbicides, seed enhancement and growth enhancement applications.

Accordingly, aspects of the present invention relate to formulations comprising the compounds of formula I or conjugates thereof, optionally in conjunction with one or more formulation ingredients. Such formulation ingredients include, but are not limited to, preservatives, thickening agents, antifoaming agents etc. Such formulation ingredients may optionally include additional active ingredients, such as herbicides etc.

In aspects, the invention relates to formulations comprising such compounds and conjugates, and to the use of such compounds, conjugates and formulations in controlled ROS generation applications in plant, fungi and bacteria.

In aspects, the invention relates to compounds of formula I:

I

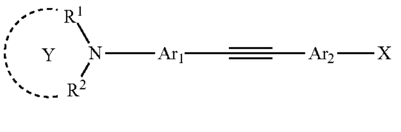

in which:

$R^1$ is H or an alkyl group comprising from 1 to 10 carbon atoms, optionally substituted with one or more N atoms, and $R^2$ is selected from an alkyl group comprising from 1 to 10 carbon atoms, optionally substituted with one or more N atoms, $—(CH_2)_nR^3$, $—(CH_2)_nNHR^3$, and $—(CH_2)_2(COCH_2)_nR^3$ in which n is an integer from 1 to 10 and $R^3$ is $—NH_2$, —OH, $—SO_2PhCH_3$, or —COOH; or $R^1$ and $R^2$ form part of a heterocyclic group Y having from 3 to 12 ring members with the proviso that when $R^1$ and $R^2$ form part of a heterocyclic group Y having from 3 to 12 ring members, the N of the heterocyclic group is in a para position with respect to the acetylene group of the compound of formula I;

$Ar_1$ and $Ar_2$ are each, independently, an aromatic group; and

X is an electron deficient group;

and stereoisomers thereof, in free or salt form.

In aspects, the invention relates to compounds of formula I:

I

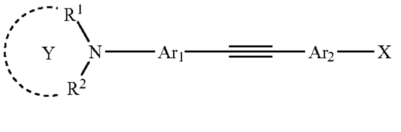

in which:

$R^1$ is H or an alkyl group comprising from 1 to 10 carbon atoms, optionally substituted with one or more N atoms, and $R^2$ is selected from an alkyl group comprising from 1 to 10 carbon atoms, optionally substituted with one or more N atoms, $—(CH_2)_nR^3$, and $—(CH_2)_2(COCH_2)_nR^3$ in which n is an integer from 1 to 10 and $R^3$ is $—NH_2$, —OH, or —COOH; or $R^1$ and $R^2$ form part of a heterocyclic group Y having from 3 to 12 ring members; $Ar_1$ and $Ar_2$ are each, independently, an aromatic group; and X is an electron deficient group;

and stereoisomers thereof, in free or salt form.

EXAMPLES

The invention will now be described by way of example only with reference to the accompanying figures, in which:

FIGS. 1(*i*)-(*xxxv*) illustrate the synthesis of coupling partners and reference compound 77;

FIGS. 2(*i*)-(*xxii*) illustrates the synthesis of exemplary compounds of formula I;

FIG. 3(*a*)-(*c*) illustrates absorption and emission spectra of compounds of the invention and of reference compounds;

FIG. 4 illustrates the synthesis of (a) a THP-protected analogue of vorinostat, compound 37; (b) a THP-protected analogue of vorinostat conjugated to compound 6, compound 38; and (c) an unprotected vorinostat analogue conjugated to compound 6, compound 39;

Figure 15A:
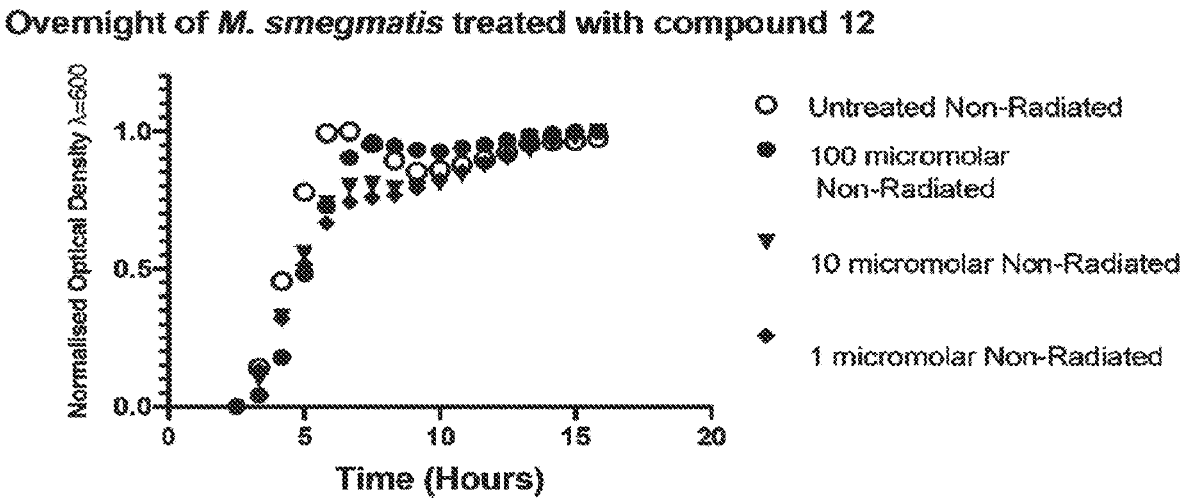
Figure 15B:
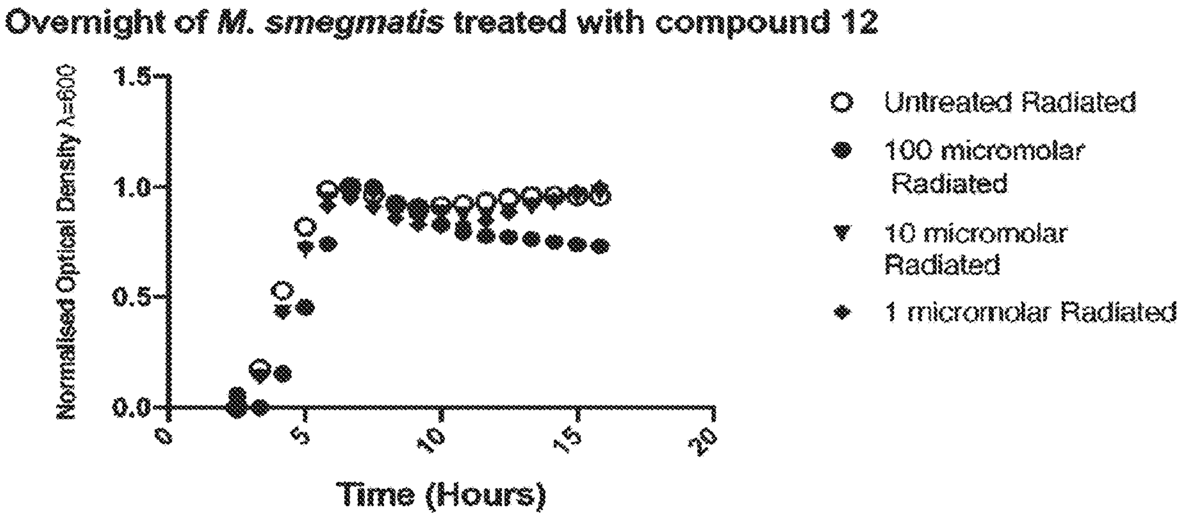
Figure 16A:
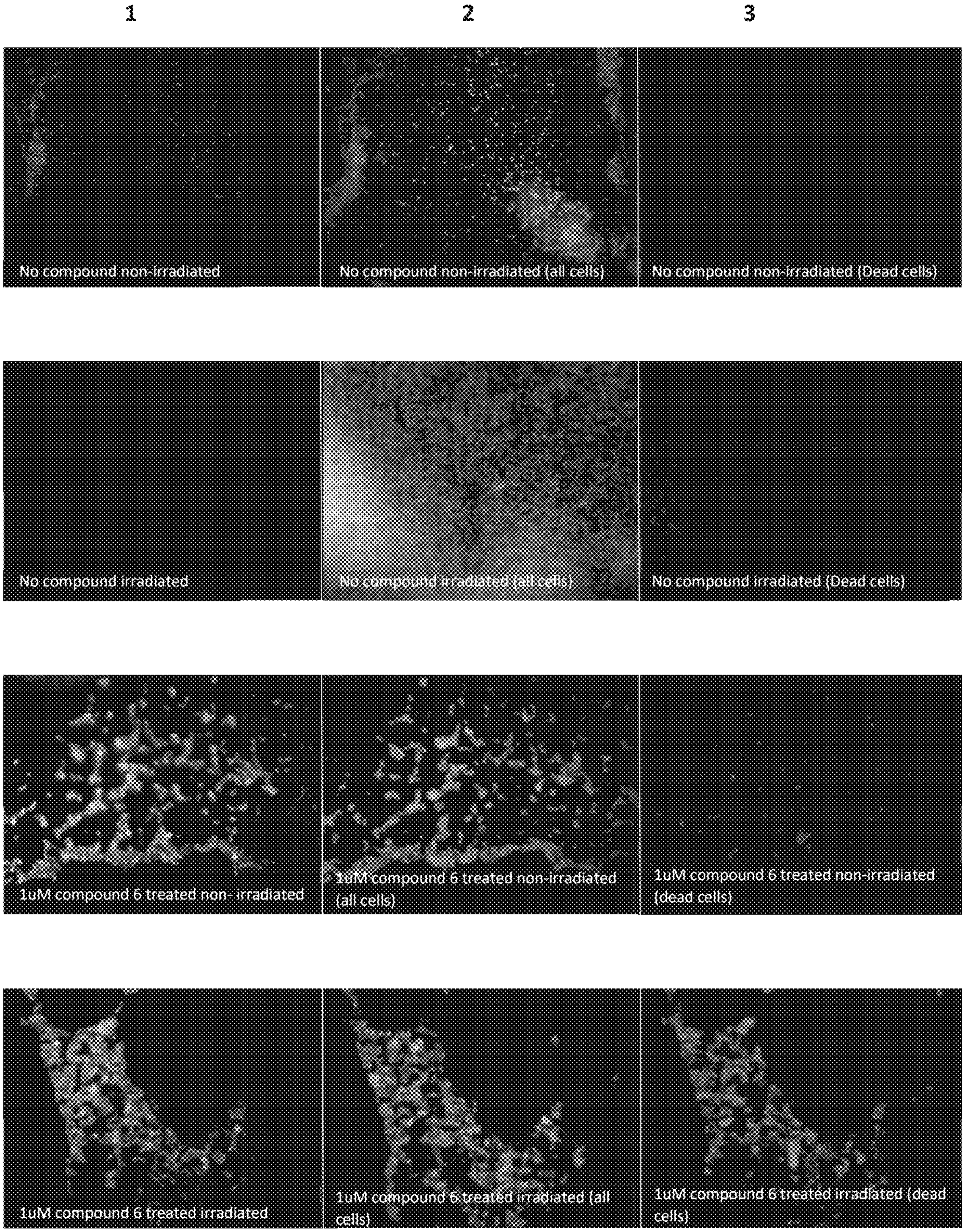
Figure 16B:
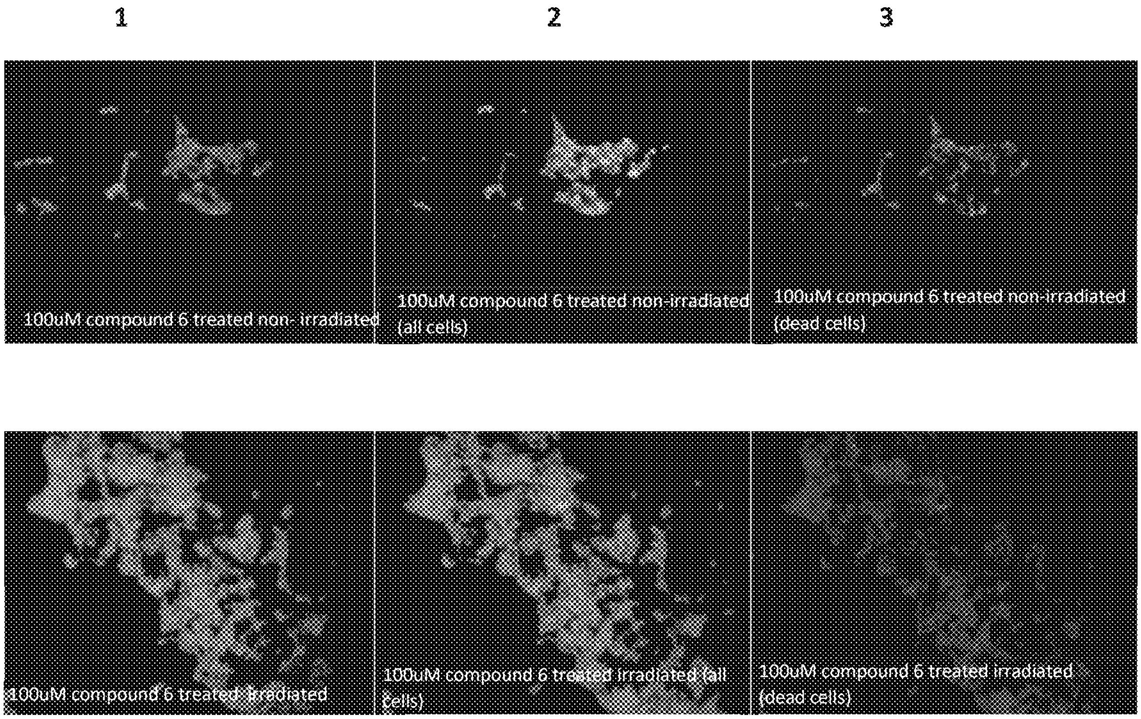
Figure 17:
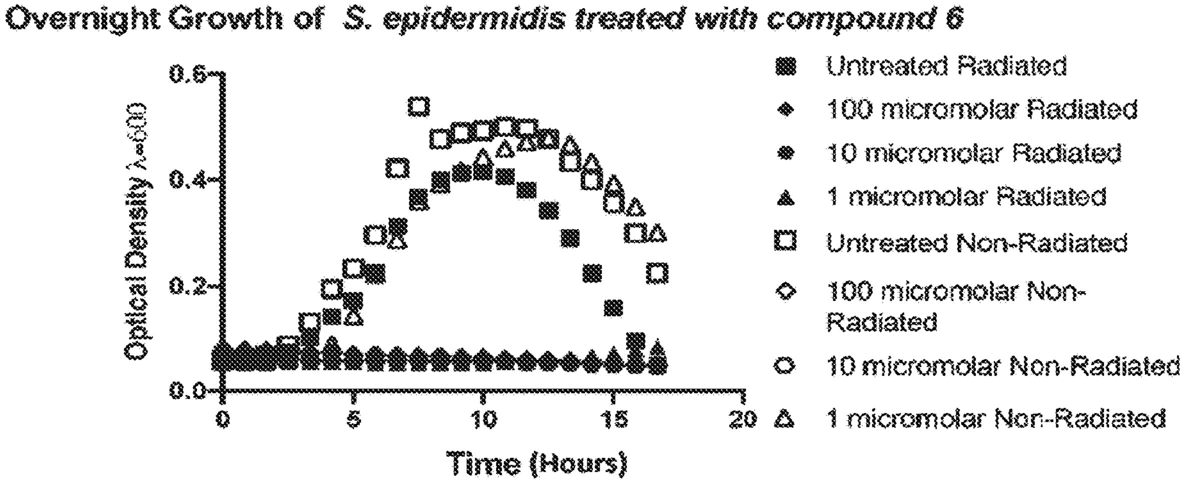
Figure 18:
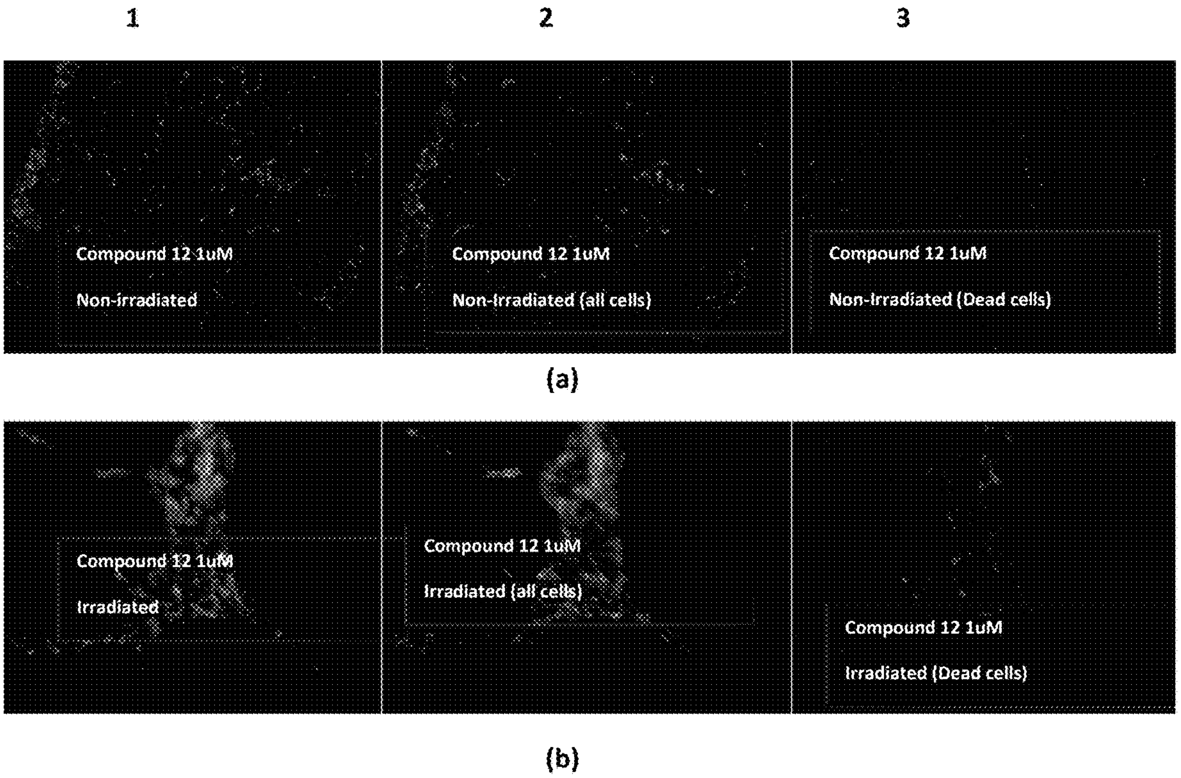
Figure 19:
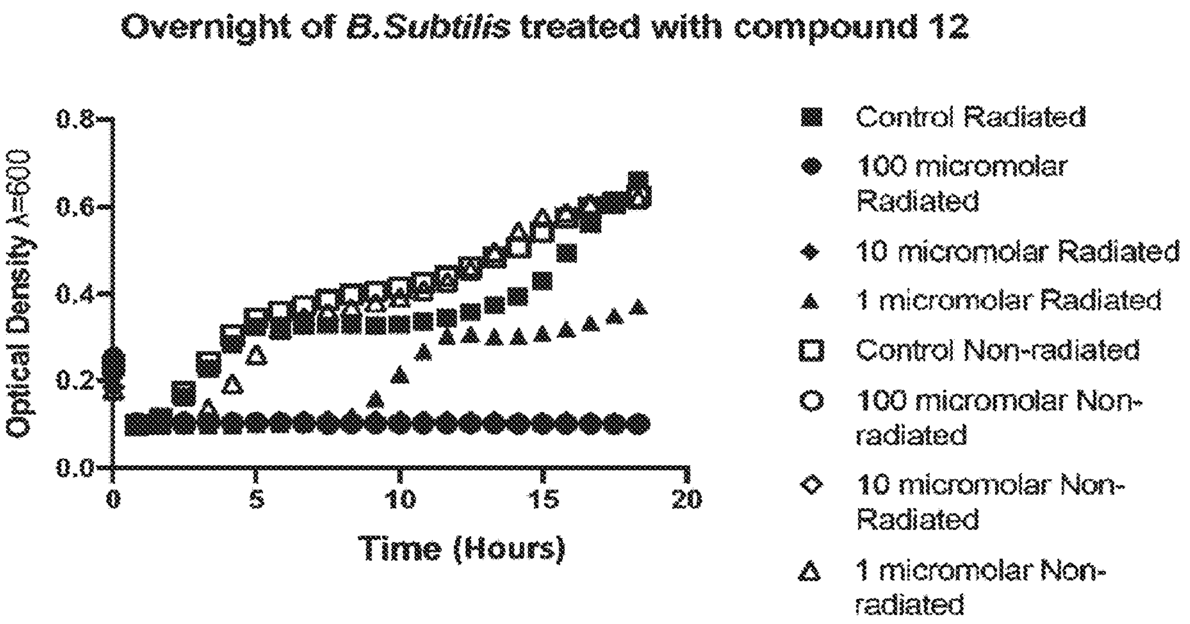
Figure 20:
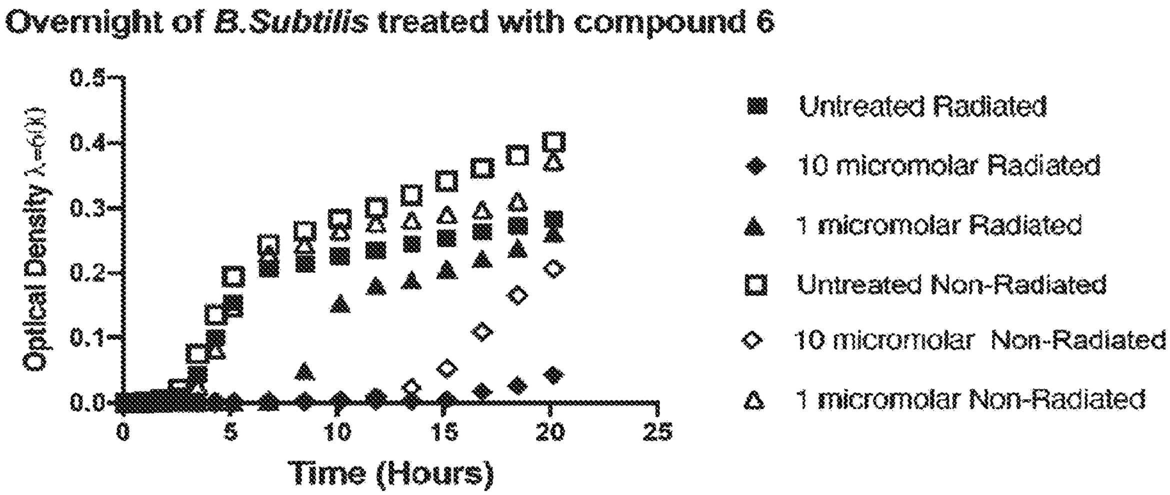
Figure 21:
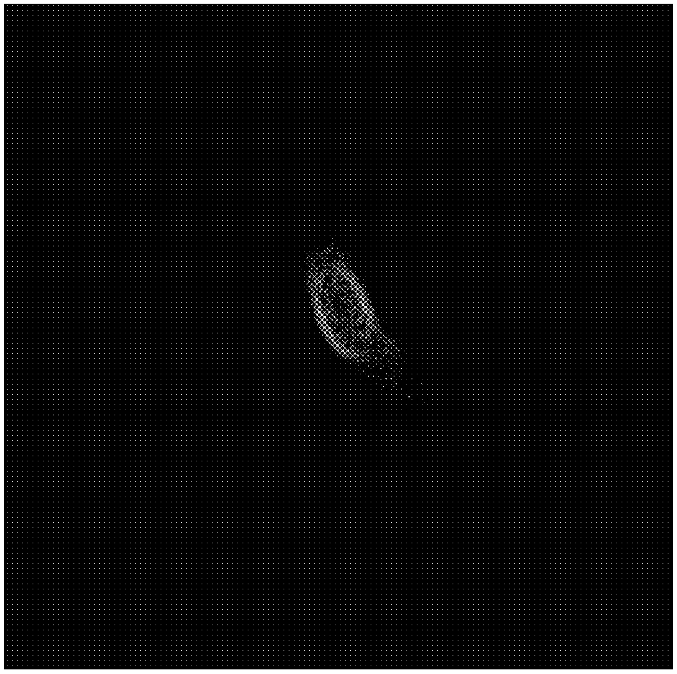

FIGS. 14(*a*)-(*d*) illustrates cell viability of black-grass cells after treatment with compounds 7, 15, 12 and 14 after UV treatment;

FIG. 15(*a*) shows the overnight growth curve of *M. smegmatis* treated with compound 12 (1-100 μM) showing optical density of cell suspension vs. time. Half of the sample was irradiated with 405 nm radiation for 5 min at approximately 15 $mW/cm^2$ as shown in 15(b);

FIG. 16(A)-(B) shows *S. epidermidis* cells treated with compound 6 (1 μM) without irradiation and with irradiation, co-stained with propidium iodide (showing non-viable cells) and Syto 9 (showing all viable and non-viable cells). Images are taken using a widefield microscope in the Blue (to image compound 6), green (to image Syto 9) and red (to image propidium iodide) channels shown in columns 1 to 3, respectively;

FIG. 17 shows the overnight growth curve of *S. epidermidis* treated with compound 6 (1-100 μM) showing optical density of cell suspension vs. time. Half of sample was irradiated (R) with 405 nm radiation for 5 min at approximately 15 $mW/cm^2$;

FIG. 18 shows *B. subtilis* cells treated with compound 12 (1 μM) without irradiation (FIG. 18(*a*)) and irradiated (FIG. 18(*b*)) with 405 nm radiation for 5 min at approximately 15 $mW/cm^2$, co-stained with propidium iodide (showing non-viable cells) and Syto 9 (showing all viable and non-viable cells). Images are taken using a widefield microscope in the Blue (to image compound 6), green (to image Syto 9) and red (to image propidium iodide) channels (columns 1 to 3, respectively);

FIG. 19 shows the overnight growth curve of *B. subtilis* treated with compound 12 (1-100 μM) with irradiation (R) and without irradiation (NR). Samples were irradiated (R) with 405 nm radiation for 5 min at approximately 15 $mW/cm^2$;

FIG. 20 shows the overnight growth curve of *B. subtilis* treated with compound 6 (10, 5, 1 μM) with irradiation and without irradiation, showing optical density of cell suspension vs. time. Half of the sample was irradiated (R) with 405 nm radiation for 5 min at approximately 15 $mW/cm^2$;

FIG. 21 shows *B subtilis* cells treated with compound 12 (10 μM) imaged using a confocal microscope and a laser excitation of 405 nm. An emission spectrum of 500/50 nm was used for image capture. Post processing was performed in ImageJ, making use of the 'Find edges' function to exemplify localisation of compound within the cell.

Example 1: Synthesis of Exemplary Compounds of Formula I

1.1 Synthesis of Coupling Partners

1.1.1. Synthesis of tert-butyl (2E)-3-(4-ethynylphenyl)prop-2-enoate, 3

Figure 1I:
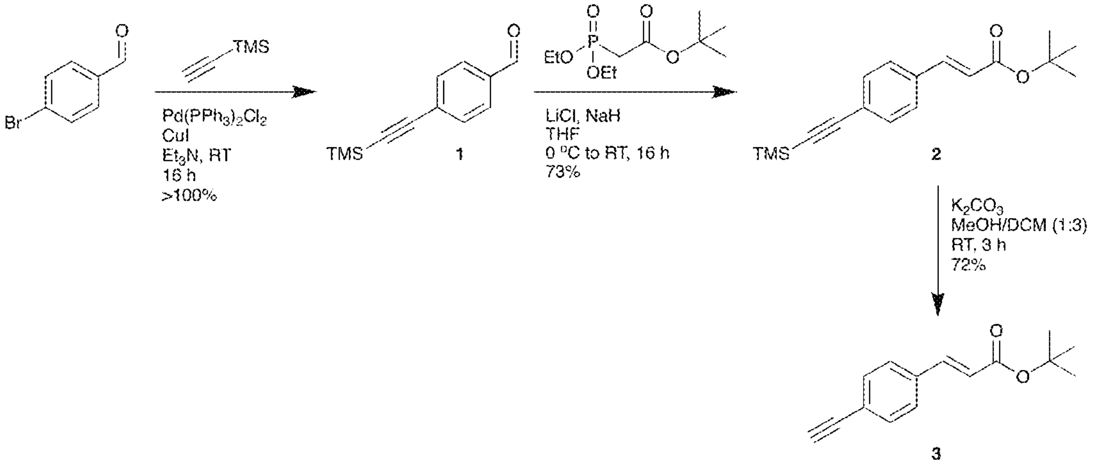
Figure 1:
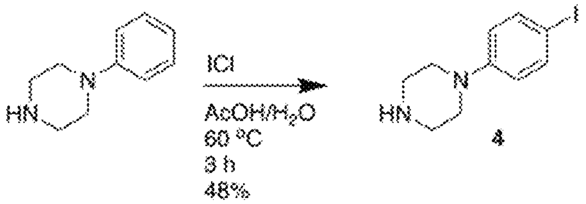
Figure 1:
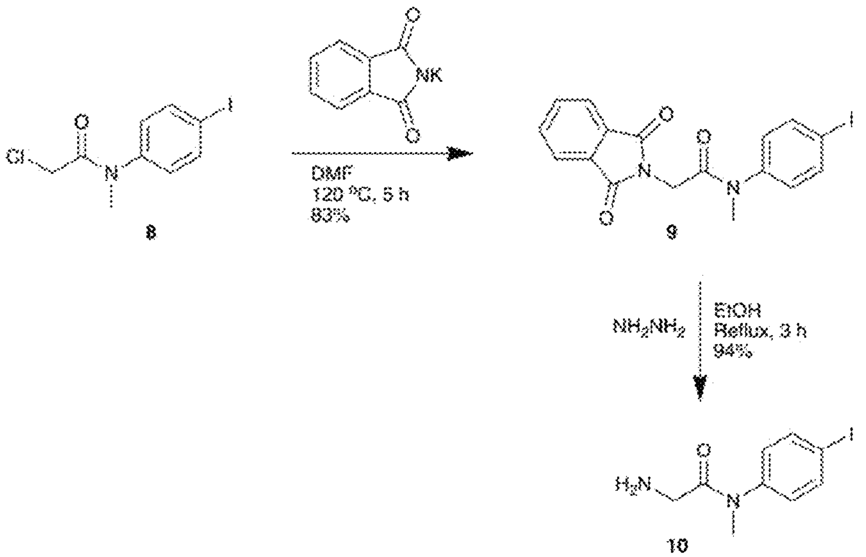
Figure 1V:
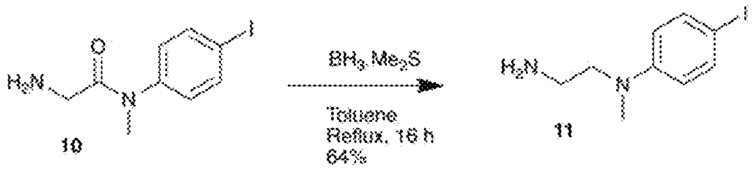
Figure 1:
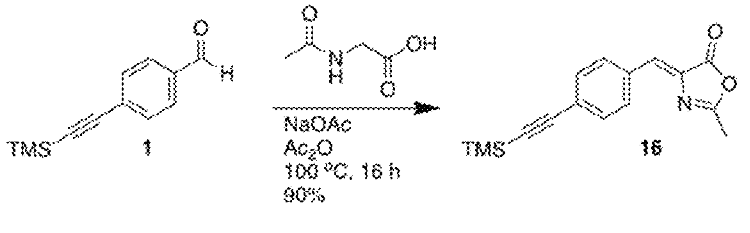
Figure 1:
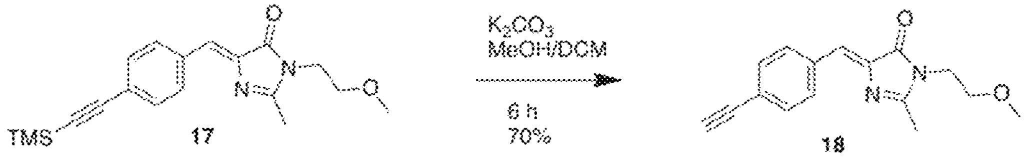
Figure 1:
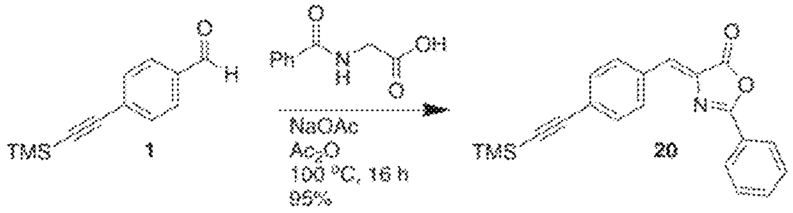
Figure 1:
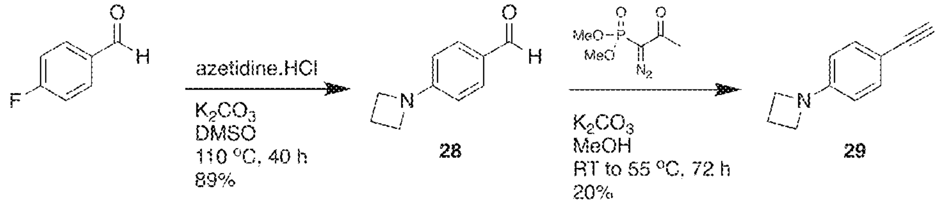
Figure 1:
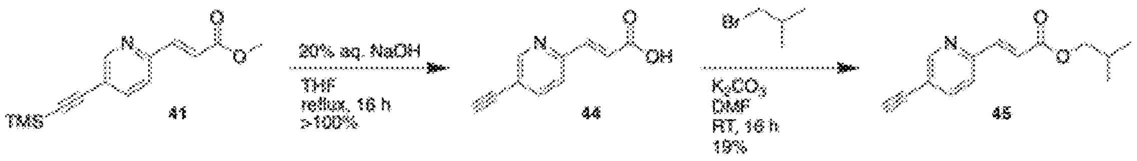

The synthesis of tert-butyl (2E)-3-(4-ethynylphenyl)prop-2-enoate (3) is illustrated in FIG. 1(*i*). Triethylamine ($Et_3N$) (250 mL) was degassed by sparging with Ar for 1 hour. 4-Bromobenzaldehyde (18.5 g, 100.0 mmol), $Pd(PPh_3)_2Cl_2$ (1.4 g, 2.00 mmol), CuI (0.38 g, 2.00 mmol) and trimethylsilylacetylene (15.2 mL, 110.0 mmol) were then added under Ar and the resultant suspension was stirred at room temperature (RT) for 16 hours (h). The suspension was diluted with heptane, passed through a short Celite/$SiO_2$ plug and the extracts were evaporated to give a crude dark solid (24 g). This was purified by Kugelrohr distillation (130-150° C., 9.0 Torr) to give compound 1 as an off-white solid (21.5 g, >100%), which was carried to the next step without further purification. Tert-butyl diethylphosphonoacetate (14.4 mL, 61.5 mmol) and LiCl (2.54 g, 60.0 mmol) were added to anhydrous tetrahydrofuran (THF) (100 mL) and the resultant solution was stirred for 15 min, whereupon compound 1 (10.1 g, 50.0 mmol) was added. To this solution was slowly added 1,8-diazabicyclo[5.4.0]undec-7-ene (DBU) (8.2 mL, 55.0 mmol), and the resultant slurry was stirred at RT for 16 h. This was poured into crushed ice, and extracted with ethyl acetate (EtOAc). The organics were washed with $H_2O$ and brine, dried ($MgSO_4$) and evaporated to give a crude white solid (18 g). This was purified by recrystallisation from heptane to give compound 2 as a colourless crystalline solid (10.99 g, 73%): $^1H$ NMR (400 MHz, $CDCl_3$) δ 0.25 (s, 9H), 1.53 (s, 9H), 6.36 (d, J=16.0 Hz, 1H), 7.40-7.49 (m, 4H), 7.54 (d, J=16.0 Hz, 1H). Compound 2 (10.95 g, 36.4 mmol) and $K_2CO_3$ (7.55 g, 54.6 mmol) were added to methanol (MeOH)/dichloromethane (DCM) (200 mL, 1:3) and the resultant solution was stirred at RT for 3 h. The solution was diluted with DCM, and the organics washed with sat. $NH_4Cl$ and $H_2O$, dried ($MgSO_4$) and evaporated to give a crude solid (8 g). This was purified by recrystallization from heptane to give compound 3 as a colourless crystalline solid (5.96 g, 72%): $^1H$ NMR (600 MHz, $CDCl_3$) δ 1.53 (s, 9H), 3.17 (s, 1H), 6.36 (d, J=16.0 Hz, 1H), 7.43-7.49 (m, 4H), 7.54 (d, J=16.0 Hz, 1H); $^{13}C$ NMR (151 MHz, $cdcl_3$) δ 28.1, 79.0, 80.6, 83.2, 121.2, 123.5, 127.7, 132.5, 135.0, 142.4, 166.0; IR (ATR) $v_{max}/cm^{-1}$ 3281 m, 3064 w, 3000 w, 2980 w, 2936 w, 1691 s, 1641 m, 1370 m, 1296 s, 1153 s, 1002 m, 980 m, 832 s;

MS(ASAP): m/z=228.1 $[M+H]^+$; HRMS (ASAP) calcd. for $C_{15}H_{16}O_2$ $[M+H]^+$: 228.1150, found 228.1161.

1.1.2 Synthesis of 1-(4-Iodophenyl)piperazine, 4

The synthesis of 1-(4-Iodophenyl)piperazine (4) is illustrated in FIG. 1(*ii*). To a mechanically stirred solution of 1-phenylpiperazine (20.5 mL, 134.0 mmol) in acetic acid (AcOH)/$H_2O$ (3:1, 84 mL) at 55° C. was added dropwise a solution of ICI (24.0 g, 148.0 mmol) in AcOH/$H_2O$ (3:1, 84 mL). The resultant slurry was further stirred for 1 h and then cooled to RT and stirred for a further 1 h. The slurry was poured into crushed ice, and 20% aq. NaOH added until pH 13. The solution was then extracted with DCM, washed with $H_2O$, dried ($MgSO_4$) and evaporated to give a crude dark solid. This was purified by $SiO_2$ chromatography (9:1, DCM/MeOH, 1% $Et_3N$) to give a pale yellow solid which was further recrystallised from MeOH/$H_2O$ (1:1) to give compound 4 as a beige solid (18.5 g, 48%): $^1H$ NMR (600 MHz, $CDCl_3$) δ 2.97-3.03 (m, 4H), 3.07-3.14 (m, 4H), 6.65-6.69 (m, 2H), 7.48-7.52 (m, 2H); $^{13}C$ NMR (151 MHz, $CDCl_3$) δ 45.9, 49.9, 81.4, 118.0, 137.7, 151.3; IR (ATR) $v_{max}/cm^{-1}$ 3032 w, 2955 w, 2829 m, 1582 m, 1489 m, 1243 s, 914 m, 803 s; MS(ASAP): m/z=289.0 $[M+H]^+$; HRMS (ASAP) calcd. for $C_{10}H_{13}N_2I$ $[M]^+$: 288.0124, found 288.0114.

1.1.3 Synthesis of 2-chloro-N-(4-iodophenyl)-N-methylacetamide, 8

The synthesis of 2-chloro-N-(4-iodophenyl)-N-methylacetamide (8) is illustrated in FIG. 1(*iii*). 4-Iodo-N-methylaniline (13.9 g, 59.7 mmol) was dissolved in DCM (100 mL), whereupon chloroacetyl chloride (5.2 mL, 65.7 mmol) and $Et_3N$ (9.2 mL, 65.7 mmol) were added and the resultant mixture was stirred for 16 h at room temperature (RT). The solution was then diluted with DCM, washed with sat. $NH_4Cl$ and $H_2O$, dried ($MgSO_4$) and evaporated to give a crude solid. This was purified by $SiO_2$ chromatography (8:2, heptane/EtOAc) to give compound 8 as an off-white solid (8.26 g, 45%): $^1H$ NMR (600 MHz, $CDCl_3$) δ 3.28 (s, 3H), 3.83 (s, 2H), 6.95-7.06 (m, 2H), 7.78 (d, J=8.1 Hz, 2H); $^{13}C$ NMR (151 MHz, $CDCl_3$) δ 37.9, 41.2, 93.9, 129.0, 139.3, 142.4, 166.1; IR (ATR) $v_{max}/cm^{-1}$ 2996 w, 2947 w, 1664 s, 1480 m, 1371 m, 1260 m, 1009 m, 824 m, 552 s; MS (ASAP) m/z=310.0 $[M+H]^+$; HRMS (ASAP) calcd. for $C_9H_{10}ONICl$ $[M+H]^+$: 309.9496, found 309.9494.

1.1.4 Synthesis of 2-amino-N-(4-iodophenyl)-N-methylacetamide, 10

The synthesis of 2-amino-N-(4-iodophenyl)-N-methylacetamide (10) is illustrated in FIG. 1(*iv*). Compound 8 (8.23 g, 26.6 mmol) and potassium phthalimide (7.39 g, 39.9 mmol) were dissolved in dimethylformamide (DMF) (40 mL) and the resultant mixture was heated to 120° C. and stirred for 5 h. The solution was cooled, and diluted with $H_2O$. The resultant precipitate was isolated by filtration, washed with $H_2O$ and then recrystallised from ethanol (EtOH) to give compound 9 as a white solid (9.26 g, 83%). Compound 9 (9.2 g, 11.51 mmol) was dissolved in EtOH (50 mL) and the resultant mixture was heated to reflux, whereupon hydrazine hydrate (64%, 1.22 mL, 24.09 mmol) was added and the mixture was stirred at reflux for 3 h. The suspension was then cooled, and the resultant precipitate was filtered. The filtrate was evaporated to give a crude oily solid (7 g), which was purified by $SiO_2$ chromatography (9:1, DCM/MeOH with 1% $Et_3N$) to give compound 10 as a crystalline white solid (5.97 g, 94%): $^1H$ NMR (600 MHz, $CDCl_3$) δ 3.13 (s, 2H), 3.25 (s, 3H), 6.92 (d, J=8.0 Hz, 2H), 7.74 (d, J=8.0 Hz, 2H); $^{13}C$ NMR (151 MHz, $CDCl_3$) δ 37.3, 44.1, 93.3, 129.1, 139.1, 142.4, 172.6; IR (ATR) $v_{max}/cm^{-1}$ 3365 m, 3301 w, 3055 w, 2947 w, 2885 w, 1649 s, 1570 m, 1486 m, 1423 m, 1345 m, 1109 m, 1013 m, 892 s; MS(ES): m/z=291.1 $[M+H]^+$; HRMS (ES) calcd. for $C_9H_{12}N_2OI$ $[M+H]^+$: 290.9994, found 291.0012.

1.1.5 Synthesis of N-(2-aminoethyl)-4-iodo-N-methylaniline, 11

The synthesis of N-(2-aminoethyl)-4-iodo-N-methylaniline, (11) is illustrated in FIG. 1(*v*).

Compound 10 (5.72 g, 19.72 mmol) was dissolved in anhydrous toluene (50 mL) under $N_2$, whereupon $BH_3 \cdot Me_2S$ (2.0 μM, 10.35 mL, 20.70 mmol) was added and the resultant solution was stirred at reflux for 16 h. The solution was cooled, and 10% $Na_2CO_3$ was added, whereupon the solution was stirred vigorously for 10 mins. The solution was then diluted with EtOAc, washed with $H_2O$ and brine, dried ($MgSO_4$) and evaporated to give a crude yellow oil (4.4 g). This was purified by $SiO_2$ chromatography (9:1, DCM:MeOH, 0.5% $Et_3N$) to give compound 11 as a yellow oil (3.46 g, 64%), which was carried immediately to the next step: $^1H$ NMR (400 MHz, $CDCl_3$) δ 2.90 (t, J=6.6 Hz, 2H), 2.93 (s, 3H), 3.36 (t, J=665 Hz, 2H), 6.47-6.57 (m, 2H), 7.41-7.49 (m, 2H).

1.1.6 Synthesis of (4Z)-2-methyl-4-({4-[2-(trimethylsilyl)ethynyl]phenyl}methylidene)-4,5-dihydro-1,3-oxazol-5-one, 16

The synthesis of (4Z)-2-methyl-4-({4-[2-(trimethylsilyl)ethynyl]phenyl}methylidene)-4,5-dihydro-1,3-oxazol-5-one (16) is illustrated in FIG. 1(*vi*). Compound 1 (5.0 g, 24.7 mmol), N-acetyl glycine (3.46 g, 29.6 mmol) and sodium acetate (NaOAc) (2.43 g, 29.6 mmol) were dissolved in acetic anhydride (25 mL) and the resultant solution was stirred at 80° C. for 16 h. The solution was cooled, and ice water added to give an orange precipitate. This was filtered, washed with $H_2O$ and dried to give compound 16 as an orange/brown solid (6.92 g, 91%), which was carried directly to the next step without further purification: $^1H$ NMR (400 MHz, $CDCl_3$) δ 0.27 (s, 9H), 2.42 (s, 3H), 7.09 (s, 1H), 7.47-7.53 (m, 2H), 7.98-8.04 (m, 2H).

1.1.7 Synthesis of 4Z)-1-(2-methoxyethyl)-2-methyl-4-({4-[2-(trimethylsilyl)ethynyl]phenyl}methylidene)-4,5-dihydro-1H-imidazol-5-one, 17

The synthesis of (4Z)-1-(2-methoxyethyl)-2-methyl-4-({4-[2-(trimethylsilyl)ethynyl]phenyl}methylidene)-4,5-dihydro-1H-imidazol-5-one (17) is illustrated in FIG. 1(*vii*). Compound 16 (5.50 g, 19.4 mmol) and 2-methoxyethylamine (1.68 mL, 19.4 mmol) were dissolved in pyridine (40 mL) and the resultant solution was stirred at RT for 0.5 h. N,O-bistrimethylsilylacetamide (9.49 mL, 38.8 mmol) was added and the solution was stirred at 110° C. for 16 h. The solution was then cooled, diluted with EtOAc and the organics were washed with sat. $NH_4Cl$, $H_2O$ and brine, dried ($MgSO_4$) and evaporated to give a crude dark oil (7.7 g). This was purified by $SiO_2$ chromatography ($Et_2O$) to give compound 17 as a light brown solid (4.03 g, 61%): $^1H$ NMR (400 MHz, $CDCl_3$) δ 0.26 (s, 9H), 2.42 (s, 3H), 3.30 (s, 3H), 3.53 (t, J=5.1 Hz, 2H), 3.77 (t, J=5.1 Hz, 2H), 7.02 (s, 1H), 7.43-7.51 (m, 2H), 8.02-8.11 (m, 2H); $^{13}$C NMR (101 MHz, $CDCl_3$) δ −0.1, 16.0, 41.0, 59.0, 70.5, 96.8, 105.0, 124.5, 125.8, 131.8, 132.1, 134.3, 139.0, 163.9, 170.6; IR (ATR) $v_{max}$/cm$^{-1}$ 2957 w, 2896 w, 2833 w, 2154 m, 1710 s, 1645 s, 1599 m, 1562 s, 1405 s, 1357 s, 1249 s, 1126 m, 862 s, 841 s; MS(ES): m/z=341.2 [M+H]$^+$; HRMS (ES) calcd. for $C_{19}H_{24}N_2O_2Si$ [M+H]$^+$: 341.1685, found 341.1681.

1.1.8 Synthesis of (4Z)-4-[(4-ethynylphenyl)methylidene]-1-(2-methoxyethyl)-2-methyl-4,5-dihydro-1H-imidazol-5-one, 18

The synthesis of (4Z)-4-[(4-ethynylphenyl)methylidene]-1-(2-methoxyethyl)-2-methyl-4,5-dihydro-1H-imidazol-5-one (18) is illustrated in FIG. 1(*viii*). Compound 17 (3.6 g, 10.57 mmol) and $K_2CO_3$ (2.92 g, 21.14 mmol) were added to DCM/MeOH (9:1, 50 mL) and the resultant suspension was stirred rapidly for 20 hours. This suspension was diluted with DCM and $H_2O$ and the organics were washed with sat. $NH_4Cl$ and $H_2O$, dried ($MgSO_4$) and evaporated to give a crude brown oil (3.2 g). This was purified by $SiO_2$ chromatography (1:1, PE/EtOAc) to give compound 18 as a yellow solid (1.99 g, 70%): $^1$H NMR (400 MHz, $CDCl_3$) δ 2.43 (s, 3H), 3.20 (s, 1H), 3.31 (s, 3H), 3.53 (t, J=5.1 Hz, 2H), 3.78 (t, J=5.1 Hz, 2H), 7.03 (s, 1H), 7.49-7.54 (m, 2H), 8.07-8.12 (m, 2H); $^{13}$C NMR (101 MHz, $CDCl_3$) δ 16.0, 41.0, 59.0, 70.5, 79.2, 83.6, 123.4, 125.6, 131.8, 132.3, 134.7, 139.2, 164.1, 170.6; IR (ATR) $v_{max}$/cm$^{-1}$ 3285 m, 3241 m, 2986 w, 2933 w, 2891 w, 2831 w, 2104 w, 1704 s, 1643 s, 1600 m, 1592 s, 1404 s, 1356 s, 1125 s, 838 m; MS(ES): m/z=269.1 [M+H]$^+$; HRMS (ES) calcd. for $C_{16}H_{17}N_2O_2$ [M+H]$^+$: 269.1290, found 269.1290.

1.1.9. Synthesis of (4Z)-2-phenyl-4-({4-[2-(trimethylsilyl)ethynyl]phenyl}methylidene)-4,5-dihydro-1,3-oxazol-5-one, 20

The synthesis of (4Z)-2-phenyl-4-({4-[2-(trimethylsilyl)ethynyl]phenyl}methylidene)-4,5-dihydro-1,3-oxazol-5-one (20) is illustrated in FIG. 1(*ix*). Compound 1 (12.5 g, 61.7 mmol), benzoylaminoethanoic acid (hippuric acid) (13.3 g, 74.0 mmol) and NaOAc (6.07 g, 74.0 mmol) were dissolved in acetic anhydride (80 mL) and the resultant solution was heated at 100° C. for 18 h. The solution was cooled and diluted with water, whereupon a yellow precipitate was formed. This was filtered and dried to give a crude yellow solid which was purified by $SiO_2$ chromatography (95:5, PE/EtOAc) to give compound 20 as a bright yellow solid (23.25 g, >100%): $^1$H NMR (400 MHz, $CDCl_3$) δ 0.28 (s, 9H), 7.20 (s, 1H), 7.50-7.58 (m, 4H), 7.63 (ddt, J=8.4, 6.7, 1.4 Hz, 1H), 8.11-8.17 (m, 2H), 8.16-8.21 (m, 2H); $^{13}$C NMR (101 MHz, $CDCl_3$) δ −0.1, 97.9, 104.7, 125.5, 125.8, 128.4, 129.0, 130.5, 132.1, 132.3, 133.4, 133.5, 133.7, 163.8, 167.4; IR (ATR) $v_{max}$/cm$^{-1}$ 3063 w, 2959 w, 2898 w, 2155 m, 1768 s, 1654 s, 1598 m, 859 s; MS(ES): m/z=346.1 [M+H]$^+$; HRMS (ES) calcd. for $C_{21}H_{20}NO_2Si$ [M+H]$^+$: 346.1263, found 346.1266.

1.1.10 Synthesis of (4Z)-1-[2-(morpholin-4-yl)ethyl]-2-phenyl-4-({4-[2-(trimethylsilyl)ethynyl]phenyl}methylidene)-4,5-dihydro-1H-imidazol-5-one, 21

The synthesis of (4Z)-1-[2-(morpholin-4-yl)ethyl]-2-phenyl-4-({4-[2-(trimethylsilyl)ethynyl]phenyl}methylidene)-4,5-dihydro-1H-imidazol-5-one, (21) is illustrated in FIG. 1(*x*). Compound 20 (10.36 g, 30.0 mmol) and 4-(2-aminoethyl)morpholine (3.93 mL, 30.0 mmol) were dissolved in pyridine (65 mL) and the resultant solution was stirred at RT for 0.5 h. N,O-Bistrimethylsilylacetamide (14.67 mL, 60.0 mmol) was added and the solution was stirred at 110° C. for 18 h. The solution was then cooled, diluted with DCM and the organics were washed with sat. $NH_4Cl$, $H_2O$ and brine, dried ($MgSO_4$) and evaporated to give a crude dark solid. This was purified by $SiO_2$ chromatography (1:9, PE/EtOAc) to give compound 21 as a thick red oil that slowly crystallised (12.91 g, 94%) which was carried directly to the next step without further purification: $^1$H NMR (400 MHz, $CDCl_3$) δ 0.26 (s, 9H), 2.24-2.31 (m, 4H), 2.45 (t, J=6.3 Hz, 2H), 3.47-3.56 (m, 4H), 3.91 (t, J=6.3 Hz, 2H), 7.18 (s, 1H), 7.46-7.51 (m, 2H), 7.51-7.58 (m, 3H), 7.79-7.87 (m, 2H), 8.13-8.19 (m, 2H).

1.1.11 Synthesis of (4Z)-4-[(4-ethynylphenyl)methylidene]-1-[2-(morpholin-4-yl)ethyl]-2-phenyl-4,5-dihydro-1H-imidazol-5-one, 22

The synthesis of (4Z)-4-[(4-ethynylphenyl)methylidene]-1-[2-(morpholin-4-yl)ethyl]-2-phenyl-4,5-dihydro-1H-imidazol-5-one, 22 is illustrated in FIG. 1(*xi*). Compound 21 (12.91 g, 28.2 mmol) and $K_2CO_3$ (7.8 g, 56.42 mmol) were added to DCM/MeOH (4:1, 100 mL) and the resultant suspension was stirred rapidly for 20 h. This suspension was diluted with DCM and $H_2O$ and the organics were washed with sat. $NH_4Cl$ and $H_2O$, dried ($MgSO_4$) and evaporated to give a crude solid. This was purified by $SiO_2$ chromatography (100% EtOAc) to give compound 22 as a yellow solid (7.69 g, 71%): $^1$H NMR (400 MHz, $CDCl_3$) δ 2.24-2.30 (m, 4H), 2.44 (t, J=6.3 Hz, 2H), 3.21 (s, 1H), 3.43-3.57 (m, 4H), 3.91 (t, J=6.3 Hz, 2H), 7.18 (s, 1H), 7.49-7.59 (m, 5H), 7.78-7.85 (m, 2H), 8.14-8.21 (m, 2H); $^{13}$C NMR (101 MHz, $CDCl_3$) δ 39.0, 53.6, 56.6, 66.7, 79.5, 83.6, 123.6, 127.2, 128.4, 128.8, 129.9, 131.3, 132.2, 132.3, 134.7, 139.5, 163.4, 171.6; IR (ATR) $v_{max}$/cm$^{-1}$ 3290 w, 3238 w, 2956 w, 2854 w, 2811 w, 1705 s, 1640 s, 1597 m, 1491 s, 1446 m, 1391 s, 1351 s, 1314 m, 1115 s, 868 m; MS(ES): m/z=386.2 [M+H]$^+$; HRMS (ES) calcd. for $C_{24}H_{24}N_3O_2$ [M+H]$^+$: 386.1869, found 386.1858.

1.1.12 Synthesis of 5-iodothiophene-2-carbaldehyde, 24

The synthesis of 5-iodothiophene-2-carbaldehyde, 24 is illustrated in FIG. 1(*xii*). To a solution of 2-thiophenecarboxaldehyde (9.34 mL, 100.0 mmol) in EtOH (50 mL) at 50° C. was added N-iodosuccinimide (24.75 g, 110.0 mmol) and p-toluenesulfonic acid monohydrate (1.90 g, 10.0 mmol), whereupon the resultant solution was stirred at 50° C. for 20 min. 1M HCl (80 mL) was added, and the mixture was extracted with EtOAc, washed with sat. $Na_2S_2O_3$, $H_2O$ and brine, dried ($MgSO_4$) and evaporated to give compound 24 as a yellow oil that slowly crystallised (25.34 g, >100%): $^1$H NMR (300 MHz, $CDCl_3$) δ 7.39 (s, 2H), 9.77 (s, 1H).

1.1.13 Synthesis of tert-butyl (2E)-3-(5-iodothiophen-2-yl)prop-2-enoate, 25

The synthesis of tert-butyl (2E)-3-(5-iodothiophen-2-yl)prop-2-enoate, 25 is illustrated in FIG. 1(*xiii*). Tert-butyl diethylphosphonoacetate (8.5 mL, 36.0 mmol) and LiCl (1.49 g, 35.2 mmol) were added to anhydrous THF (100 mL) and the resultant solution was stirred for 15 min, whereupon compound 24 (6.97 g, 29.3 mmol) was added. To this solution was slowly added DBU (4.82 mL, 32.2 mmol), and the resultant slurry was stirred at RT for 16 h. This was poured into crushed ice, and extracted with EtOAc. The organics were washed with $H_2O$ and brine, dried ($MgSO_4$) and evaporated to give a crude brown oil (12 g). This was purified by $SiO_2$ chromatography (9:1, heptane/EtOAc) to give compound 25 as an orange oil (10.99 g, 73%): $^1$H NMR (700 MHz, $CDCl_3$) δ 1.51 (s, 9H), 6.07 (d, J=15.7 Hz, 1H), 6.85 (d, J=3.8 Hz, 1H), 7.18 (d, J=3.8 Hz, 1H), 7.58 (dd, J=15.7, 0.6 Hz, 1H); $^{13}$C NMR (176 MHz, $CDCl_3$) δ 28.2, 80.7, 119.8, 131.6, 134.7, 137.9, 145.7, 165.8; IR (ATR) $v_{max}$/cm$^{-1}$ 2976 w, 2931 w, 1698 s, 1622 s, 1417 m, 1367 m, 1256 m, 1140 s, 964 m, 793 m; MS(ES): m/z=359.2 $[M+H]^+$.

1.1.14 Synthesis of tert-butyl (2E)-3-(5-ethynylthiophen-2-yl)prop-2-enoate, 26

The synthesis of tert-butyl (2E)-3-(5-ethynylthiophen-2-yl)prop-2-enoate, 26 is illustrated in FIG. 1(*xiv*). $Et_3N$ (150 mL) was degassed by sparging with Ar for 1 h. Compound 25 (8.4 g, 24.98 mmol), $Pd(PPh_3)_2Cl_2$ (0.175 g, 0.25 mmol), CuI (48 mg, 0.25 mmol) and trimethylsilylacetylene (4.15 mL, 30.0 mmol) were then added under Ar and the resultant suspension was stirred at RT for 16 h. The suspension was diluted with methyl tert-butyl ether (MTBE), passed through a short Celite/$SiO_2$ plug and the extracts were evaporated to give a crude brown oil (8.8 g). This was purified by $SiO_2$ chromatography (95:5, heptane/EtOAc) to give tert-butyl (2E)-3-{5-[2-(trimethylsilyl)ethynyl]thiophen-2-yl}prop-2-enoate as an orange oil (8.51 g, >100%), which was carried to the next step without further purification: $^1$H NMR (400 MHz, $CDCl_3$) δ 0.25 (s, 9H), 1.51 (s, 9H), 6.12 (d, J=15.7 Hz, 1H), 7.05 (d, J=3.8 Hz, 1H), 7.12 (d, J=3.8 Hz, 1H), 7.57 (dd, J=15.7, 0.6 Hz, 1H). To a MeOH/DCM solution (1:10, 110 mL) was added tert-butyl (2E)-3-{5-[2-(trimethylsilyl)ethynyl]thiophen-2-yl}prop-2-enoate (8.51 g, 27.76 mmol) and $K_2CO_3$ (7.67 g, 55.55 mmol), and the resultant mixture was stirred under $N_2$for 16 h at RT. The solution was then diluted with DCM, washed with sat. $NH_4Cl$, $H_2O$ and brine, dried ($MgSO_4$) and evaporated to give a crude solid (3.6 g). This was purified by $SiO_2$ chromatography (97:3, heptane/EtOAc) to give compound 26 as a light yellow oil (3.50 g, 54%), which was immediately carried to the next step: $^1$H NMR (400 MHz, $CDCl_3$) δ 1.53 (s, 9H), 3.45 (s, 1H), 6.16 (d, J=15.7 Hz, 1H), 7.08 (d, J=3.8 Hz, 1H), 7.18 (d, J=3.8 Hz, 1H), 7.59 (dd, J=15.8, 0.6 Hz, 1H).

1.1.15 Synthesis of 4-(azetidin-1-yl)benzaldehyde, 28

The synthesis of 4-(azetidin-1-yl)benzaldehyde (28) is illustrated in FIG. 1(*xv*). To a solution of 4-fluorobenzaldehyde (1.52 mL, 14.2 mmol) in dimethyl sulfoxide (DMSO) (50 mL) was added azetidine·HCl (1.81 g, 19.4 mmol) and $K_2CO_3$ (5.89 g, 42.6 mmol) and the resultant solution was stirred at 110° C. for 40 h. The solution was cooled, diluted with $H_2O$ and extracted with EtOAc (×3). The organics were washed with $H_2O$ and brine, dried ($MgSO_4$) and evaporated to give a crude yellow solid. This was purified by $SiO_2$ chromatography (7:3, PE/EtOAc) to give compound 28 as a yellow crystalline solid (2.04 g, 89%): $^1$H NMR (400 MHz, $CDCl_3$) δ 2.44 (pent, J=7.4 Hz, 2H), 3.98-4.06 (t, J=7.4 Hz, 4H), 6.32-6.43 (m, 2H), 7.65-7.75 (m, 2H), 9.71 (s, 1H); $^{13}$C NMR (101 MHz, $CDCl_3$) δ 16.4, 51.4, 109.7, 125.7, 131.9, 155.0, 190.3; IR (ATR) $v_{max}$/cm$^{-1}$ 3040 w, 3002 w, 2921 m, 2856 m, 2730 w, 1672 s, 1586 s, 1551 s, 1523 s, 1476 m, 1435 m, 1382 s, 1301 s, 1221 s, 1154 s, 818 s, 683 s; MS(ES): m/z=162.1 $[M+H]^+$; HRMS (ES) calcd. for $C_{10}H_{12}NO$ $[M+H]^+$: 162.0919, found 162.0922.

1.1.16 Synthesis of 1-(4-ethynylphenyl)azetidine, 29

The synthesis of 1-(4-Ethynylphenyl)azetidine (29) is shown in FIG. 1(*xv*). To a solution of compound 28 (1.0 g, 6.2 mmol) in anhydrous MeOH (30 mL) under Ar was added $K_2CO_3$ (1.71 g, 12.4 mmol) and dimethyl-1-diazo-2-oxopropylphosphonate (1.12 mL, 7.44 mmol), and the resultant suspension was stirred at RT for 72 h. The solution was diluted with EtOAc, washed with 5% $NaHCO_3$, $H_2O$ and brine, dried ($MgSO_4$) and evaporated to give a crude brown oil (1.16 g). This was purified by $SiO_2$ chromatography (9:1, PE:EtOAc) to give compound 29 as a white solid (0.199 g, 20%): $^1$H NMR (300 MHz, $CDCl_3$) δ 2.37 (pent, J=7.4 Hz, 2H), 2.97 (s, 1H), 3.90 (t, J=7.4 Hz, 4H), 6.31-6.36 (m, 2H), 7.31-7.37 (m, 2H); $^{13}$C NMR (75 MHz, $CDCl_3$) δ 16.7, 52.0, 74.7, 84.8, 109.6, 110.6, 133.0, 151.8; IR (ATR) $v_{max}$/cm$^{-1}$ 3287 w, 2963 w, 2918 w, 2855 w, 2099 w, 1609 s, 1514 s, 1355 m, 1171 m, 1123 m, 824 m; MS(ES): m/z=158.1 $[M+H]^+$; HRMS (ES) calcd. for $Cn_{11}H_{12}N$ $[M+H]^+$: 158.0970, found 158.0971.

1.1.17 Synthesis of (4Z)-4-[(4-bromophenyl)methylidene]-2-phenyl-4,5-dihydro-1,3-oxazol-5-one, 31

The synthesis of (4Z)-4-[(4-bromophenyl)methylidene]-2-phenyl-4,5-dihydro-1,3-oxazol-5-one (31) is shown in FIG. 1(*xvi*). 4-Bromobenzaldehyde (28.46 g, 153.8 mmol), hippuric acid (35.83 g, 200.0 mmol) and NaOAc (16.4 g, 200.0 mmol) were dissolved in acetic anhydride (150 mL) and the resultant solution was heated at 100° C. for 18 h. The solution was cooled and diluted with water, whereupon a yellow precipitate was formed. This was dissolved in DCM and the organics were washed with water, dried ($MgSO_4$) and evaporated to give a crude yellow solid. This was suspended in DCM/EtOAc (1:1) and the resultant suspension was stirred for 0.5 h. The precipitate was collected by filtration, washed with cold EtOAc and dried to give compound 31 as a bright yellow solid (40.5 g, 80%): $^1$H NMR (400 MHz, $CDCl_3$) δ 7.17 (s, 1H), 7.51-7.58 (m, 2H), 7.59-7.67 (m, 3H), 8.05-8.11 (m, 2H), 8.15-8.22 (m, 2H); $^{13}$C NMR (101 MHz, $CDCl_3$) δ 167.3, 163.9, 133.8, 133.6, 133.6, 132.4, 132.2, 130.1, 129.0, 128.5, 125.9, 125.4; IR (ATR) $v_{max}$/cm$^{-1}$ 3088 w, 3061 w, 3044 w, 1651 s, 1580 s, 1553 m, 1483 m, 1323 s, 1298 s, 1159 m, 980 m, 820 s; MS(ES): m/z=328.0, 330.0 $[M+H]^+$; HRMS (ES) calcd. for $C_{16}H_{11}NO_2Br$ $[M+H]^+$: 327.9973, found 327.9974.

1.1.18 Synthesis of tert-butyl N-{2-[(4Z)-4-[(4-bromophenyl)methylidene]-5-oxo-2-phenyl-4,5-dihydro-1H-imidazol-1-yl]ethyl}carbamate, 32

The synthesis of tert-butyl N-{2-[(4Z)-4-[(4-bromophenyl)methylidene]-5-oxo-2-phenyl-4,5-dihydro-1H-imidazol-1-yl]ethyl}carbamate (32) is shown in FIG. 1(*xvi*). Compound 31 (15.0 g, 45.7 mmol) and tert-butyl N-(2-aminoethyl)carbamate(7.24 mL, 45.7 mmol) were dissolved in pyridine (80 mL) and the resultant solution was stirred at RT for 0.5 h. N,O-bistrimethylsilylacetamide (22.35 mL, 91.4 mmol) was added and the solution was stirred at 110° C. for 18 h. The solution was then cooled, diluted with EtOAc and the organics were washed with 5% HCl, $H_2O$ and brine, dried ($MgSO_4$) and evaporated to give a crude red oil. This was purified by $SiO_2$chromatography (7:3, PE/EtOAc) to give compound 32 as an orange/red solid (18.69 g, 87%) which was carried directly to the next step without further purification: $^1H$ NMR (400 MHz, $CDCl_3$) δ 1.37 (s, 9H), 3.40 (q, J=6.0 Hz, 2H), 3.90 (t, J=6.0 Hz, 2H), 4.81-4.88 (m, 1H), 7.16 (s, 1H), 7.50-7.62 (m, 5H), 7.76-7.88 (m, 2H), 8.01-8.14 (m, 2H).

1.1.19 Synthesis of (4Z)-1-(2-aminoethyl)-4-[(4-bromophenyl)methylidene]-2-phenyl-4,5-dihydro-1H-imidazol-5-one. 33

The synthesis of (4Z)-1-(2-aminoethyl)-4-[(4-bromophenyl)methylidene]-2-phenyl-4,5-dihydro-1H-imidazol-5-one (33) is shown in FIG. 1(*xvi*). Compound 32 (7.0 g, 14.88 mmol) was dissolved in trifluoroacetic acid (TFA)/DCM (1:3, 80 mL) and the resultant solution was stirred at RT for 16 h. The solution was evaporated to give a crude oil (16 g). This was purified by $SiO_2$chromatography (95:5, DCM/MeOH, 1% $Et_3N$) to give compound 33 as an impure red solid (8.89 g, >100%). This was suspended in EtOAc, stirred for 0.5 h, and the resultant precipitate filtered and washed with cold EtOAc to give compound 33 as a bright yellow solid (2.39 g, 43%): $^1H$ NMR (300 MHz, DMSO-$d_6$) δ 2.98 (t, J=6.7 Hz, 2H), 3.95 (t, J=6.7 Hz, 2H), 7.20 (s, 1H), 7.58-7.71 (m, 5H), 7.60-7.80 (br, 2H), 7.83-7.88 (m, 2H), 8.20-8.29 (m, 2H).

1.1.20 Synthesis of 5-[2-(trimethylsilyl)ethynyl]pyridine-2-carbaldehyde, 40

The synthesis of 5-[2-(trimethylsilyl)ethynyl]pyridine-2-carbaldehyde (40) is shown in FIG. 1(*xvii*). $Et_3N$ (400 mL) was degassed by sparging with Ar for 1 h. 5-Bromopyridine-2-carboxaldehyde (20.0 g, 108 mmol), trimethylsilylacetylene (16.5 mL, 119 mmol), $Pd(PPh_3)_2Cl_2$ (700 mg, 1.00 mmol) and CuI (190 mg, 1.00 mmol) were then added under Ar and the resultant suspension was stirred at RT for 18 h. The mixture was diluted with $Et_2O$ and passed through Celite/$SiO_2$ to give compound 40 as an orange solid (23.0 g, >100%): $^1H$ NMR (400 MHz, $CDCl_3$) δ 0.28 (s, 9H), 7.90 (d, J=1.2 Hz, 2H), 8.81 (t, J=1.2 Hz, 1H), 10.06 (s, 1H); $^{13}C$ NMR (176 MHz, $CDCl_3$) δ −0.3, 100.6, 102.7, 120.8, 124.6, 139.8, 151.0, 152.8, 192.5; IR (ATR) $v_{max}/cm^{-1}$ 3039 w, 2961 w, 2835 w, 2158 w, 1710 s, 1575 m, 1468 w, 1425 w, 1233 s, 1217 s, 839 s; MS (ES) m/z=204.0 $[M+H]^+$; HRMS (ES) calcd. for $C_{11}H_{13}NOSi$ $[M+H]^+$: 204.0839, found 204.0839.

1.1.21 Synthesis of methyl (2E)-3-{5-[2-(trimethylsilyl)ethynyl]pyridin-2-yl}prop-2-enoate, 41

The synthesis of methyl (2E)-3-{5-[2-(trimethylsilyl)ethynyl]pyridin-2-yl}prop-2-enoate (41) is shown in FIG. 1(*xviii*). Trimethylphosphonoacetate (21.0 mL, 129.8 mmol) and LiCl (5.5 g, 129.8 mmol) were added to anhydrous THE (300 mL) at 0° C. and the resultant solution was stirred for 15 min, whereupon compound 40 (22.0 g, 108.2 mmol) was added. To this solution was slowly added DBU (19.4 mL, 129.8 mmol), and the resultant slurry was stirred at RT for 16 h. This was poured into crushed ice, and extracted with EtOAc. The organics were washed with $H_2O$ and brine, dried ($MgSO_4$) and evaporated to give a crude brown solid (31.5 g). This was purified by $SiO_2$ chromatography to give compound 41 as a white solid (16.2 g, 58%): $^1H$ NMR (400 MHz, $CDCl_3$) δ 0.25 (s, 9H), 3.79 (s, 3H), 6.90 (d, J=15.7 Hz, 1H), 7.32 (dd, J=8.1, 0.9 Hz, 1H), 7.62 (d, J=15.7 Hz, 1H), 7.72 (dd, J=8.0, 2.1 Hz, 1H), 8.66 (d, J=2.1 Hz, 1H); $^{13}C$ NMR (101 MHz, $CDCl_3$) δ −0.3, 51.8, 100.1, 101.3, 120.7, 122.6, 123.2, 139.4, 142.6, 151.6, 152.8, 166.9; IR (ATR) $v_{max}/cm^{-1}$ 3020 w, 2955 w, 2901 w, 2160 w, 1717 s, 1644 m, 1582 m, 1547 m, 1473 m, 1318 s, 1204 s, 842 s; MS (ES) m/z=260.1 $[M+H]^+$; HRMS (ES) calcd. for $C_{14}H_{17}NO_2Si$ $[M+H]^+$: 260.1101, found 260.1101.

1.1.22 Synthesis of methyl (2E)-3-(5-ethynylpyridin-2-yl)prop-2-enoate, 42

The synthesis of methyl (2E)-3-(5-ethynylpyridin-2-yl)prop-2-enoate (42) is shown in FIG. 1(*xix*). Compound 41(5.0 g, 19.2 mmol) was dissolved in a mixture of DCM (80 mL) and MeOH (10 mL) and $K_2CO_3$ (5.3 g, 38.4 mmol) was added. The resultant suspension was stirred at RT for 16 h before being diluted with DCM and $H_2O$. The organics were washed with sat. $NH_4Cl$ and $H_2O$, dried ($MgSO_4$) to give a crude white solid (3.4 g). This was purified by recrystallisation from petroleum ether to give compound 42 as a white solid (3.06 g, 85%): $^1H$ NMR (400 MHz, $CDCl_3$) δ 3.31 (s, 1H), 3.81 (s, 3H), 6.93 (d, J=15.7 Hz, 1H), 7.36 (dd, J=8.1, 0.9 Hz, 1H), 7.65 (d, J=15.7 Hz, 1H), 7.77 (dd, J=8.0, 2.1 Hz, 1H), 8.71 (d, J=1.7 Hz, 1H); $^{13}C$ NMR (101 MHz, $CDCl_3$) δ 51.9, 80.3, 82.1, 119.7, 123.0, 123.3, 139.7, 142.5, 152.1, 153.0, 166.9; IR (ATR) $v_{max}/cm^{-1}$ 3245 m, 3015 w, 2970 w, 2951 w, 2104 w, 1738 m, 1609 s, 1632 w, 1443 m, 1368 m, 1293 m, 1272 s, 869 m; MS (ES) m/z=188.1 $[M+H]^+$; HRMS (ES) calcd. for $C_{11}H_{10}NO_2$ $[M+H]^+$: 188.0706, found 188.0706.

1.1.23 Synthesis of (2E)-3-(5-ethynylpyridin-2-yl)prop-2-enoic acid, 44

The synthesis of (2E)-3-(5-Ethynylpyridin-2-yl)prop-2-enoic acid (44) is shown in FIG. 1(*xx*). Compound 41 (5.41 g, 20.9 mmol) was dissolved in THF (40 mL), 20% aq. w/v NaOH (10 mL) was added, and the mixture was stirred at reflux for 18 h. The resultant suspension was cooled, diluted with $H_2O$ and EtOAc, and the pH was adjusted to 1 using 20% HCl. The organics were washed with $H_2O$ and brine, dried ($MgSO_4$) and evaporated to give compound 44 as an off-white solid (4.14 g, >100%): $^1H$ NMR (400 MHz, $CDCl_3$) δ 3.33 (s, 1H), 6.93 (d, J=15.1 Hz, 1H), 7.41 (d, J=6.8 Hz, 1H), 7.73 (d, J=15.1 Hz, 1H), 7.81 (dd, J=6.8, 2.0 Hz, 1H), 8.75 (s, 1H).

1.1.24 Synthesis of 2-methylpropyl (2E)-3-(5-ethynylpyridin-2-yl)prop-2-enoate, 45

The synthesis of 2-methylpropyl (2E)-3-(5-ethynylpyridin-2-yl)prop-2-enoate (45) is shown in FIG. 1(*xx*). Compound 44 (4.14 g, 23.9 mmol) was dissolved in DMF (60 mL), whereupon $K_2CO_3$ (6.6 g, 47.8 mmol) and 1-bromo-2-methylpropane (5.2 mL, 47.8 mmol) were added and the resultant suspension was stirred at RT for 18 h. This was diluted with DCM and $H_2O$ and the organics were washed with sat. $NH_4Cl$ and $H_2O$, dried ($MgSO_4$) and evaporated to give a crude brown oil (5.23 g). This was purified by $SiO_2$ chromatography (9:1, PE/EtOAc) to give compound 45 as a white solid (1.03 g, 19%): $^1H$ NMR (700 MHz, $CDCl_3$ δ 0.97 (d, J=6.8 Hz, 6H), 1.96-2.05 (hept, J=6.8 Hz, 1H), 3.30 (s, 1H), 4.00 (d, J=6.6 Hz, 2H), 6.94 (d, J=15.7 Hz, 1H), 7.38 (dd, J=8.0, 0.8 Hz, 1H), 7.65 (d, J=15.7 Hz, 1H), 7.78 (dd, J=8.0, 2.1 Hz, 1H), 8.72 (d, J=2.1 Hz, 1H); $^{13}C$ NMR (176 MHz, $CDCl_3$) δ 19.09, 27.78, 70.87, 80.29, 82.06, 119.61, 123.25, 123.50, 139.71, 142.20, 152.28, 152.97, 166.58; IR (ATR) $v_{max}/cm^{-1}$ 3238 m, 2966 w, 2953 w, 2876 w, 2108 w, 1695 s, 1640 s, 1550 m, 1313 s, 1292 s, 1160 s; MS (ES) m/z=230.1 $[M+H]^+$; HRMS (ES) calcd. for $C_{14}H_{16}NO_2$ $[M+H]^+$: 230.1176, found 230.1176.

1.1.25 Synthesis of 8-methoxy-8-oxooctanoic acid, 47

The synthesis of 8-methoxy-8-oxooctanoic acid (47) is shown in FIG. 1(*xxi*). Dimethyl suberate (112.5 g, 556 mmol) was dissolved in MeOH (400 mL) and the solution was cooled to 0° C. whereupon KOH (31.2 g, 556 mmol) was added and the resultant solution was stirred at RT for 4 h. Diethyl ether (400 mL) and $H_2O$ was added and the organic layer was separated and set aside. The aqueous layer was acidified to pH 3 and extracted with EtOAc. The organics were washed with $H_2O$ and brine, dried ($MgSO_4$) and evaporated to give a crude waxy solid. This was suspended in hexane and subsequently filtered after vigorous stirring for 0.5 h. The filtrate was evaporated to give compound 47 as a clear oil (60.51 g, 58%): $^1H$ NMR (400 MHz, $CDCl_3$) δ 1.27-1.42 (m, 4H), 1.57-1.69 (m, 4H), 2.30 (t, J=7.5 Hz, 2H), 2.34 (t, J=7.5 Hz, 2H), 3.66 (s, 3H), 10.25 (s, 1H).

1.1.26 Synthesis of methyl 7-[(oxan-2-yloxy)carbamoyl]heptanoate, 48

The synthesis of methyl 7-[(oxan-2-yloxy)carbamoyl] heptanoate (48) is shown in FIG. 1(*xxi*). Compound 47 (4.0 mL, 22.3 mmol) and 2-chloro-4,6-dimethoxy-1,3,5-triazine (4.88 g, 27.8 mmol) were dissolved in DCM (70 mL), and the solution was cooled to 0° C. 4-Methylmorpholine (3.06 mL, 27.8 mmol) was added dropwise over 5 min, and the resultant solution was stirred at 0° C. for 2 h, whereupon 0-(tetrahydropyran-2-yl)hydroxylamine (2.48 g, 21.2 mmol) and 4-methylmorpholine (2.77 mL, 26.0 mmol) were added and the solution was further stirred for 16 h. The solution was diluted with DCM, washed with $H_2O$, dried ($MgSO_4$) and evaporated to give a crude yellow oil (9.5 g). This was purified by $SiO_2$ chromatography (1:1, PE/EtOAc) to give compound 48 as a clear oil (5.26 g, 86%): $^1H$ NMR (400 MHz, $CDCl_3$) δ 1.27-1.32 (m, 4H), 1.54-1.70 (m, 7H), 1.71-1.87 (m, 3H), 2.09 (br, 2H), 2.28 (t, J=7.5 Hz, 2H), 3.57-3.63 (m, 1H), 3.64 (s, 3H), 3.86-3.98 (m, 1H), 4.92 (br, 1H), 8.59 (br, 1H); $^{13}C$ NMR (101 MHz, $CDCl_3$) δ 24.6, 25.0, 28.6, 33.9, 51.4, 62.6, 77.3, 102.4, 170.4, 174.2; IR (ATR) $v_{max}/cm^{-1}$ 3202 br, 2940 m, 2858 w, 1736 s, 1656 s, 1455 m, 1204 m, 1064 s. $^1H$ NMR (400 MHz, $CDCl_3$) δ 1.27-1.32 (m, 4H), 1.54-1.70 (m, 7H), 1.71-1.87 (m, 3H), 2.09 (br, 2H), 2.28 (t, J=7.5 Hz, 2H), 3.57-3.63 (m, 1H), 3.64 (s, 3H), 3.86-3.98 (m, 1H), 4.92 (br, 1H), 8.59 (br, 1H); $^{13}C$ NMR (101 MHz, $CDCl_3$) δ 24.6, 25.0, 28.6, 33.9, 51.4, 62.6; 77.3, 102.4, 170.4, 174.2; IR (ATR) $v_{max}/cm^1$3202 br, 2940 m, 2858 w, 1736 s, 1656 s, 1455 m, 1204 m, 1064 s; MS(ES): m/z=288.2 $[M+H]^+$; HRMS (ES) calcd. for $C_{14}H_{26}NO_5$ $[M+H]^+$: 288.1805, found 288.1805.

1.1.27 Synthesis of 7-[(oxan-2-yloxy)carbamoyl]heptanoic acid, 49

The synthesis of 7-[(oxan-2-yloxy)carbamoyl]heptanoic acid (49) is shown in FIG. 1(*xxi*). Compound 48 (5.0 g, 17.4 mmol) was dissolved in MeOH (60 mL) and $H_2O$ (20 mL), whereupon NaOH (2.78 g, 69.6 mmol) was added and the resultant solution was stirred at 50° C. for 18 h. The solution was evaporated, and the residue suspended in $H_2O$. The pH was carefully adjusted to pH 3/4 using 5% HCl and the solution was extracted with EtOAc. The organics were washed with $H_2O$ and brine, dried ($MgSO_4$) and evaporated to give compound 49 as a clear oil (4.27 g, 90%): $^1H$ NMR (400 MHz, $CDCl_3$) δ 1.28-1.40 (m, 4H), 1.52-1.69 (m, 7H), 1.74-1.84 (m, 3H), 2.11 (br, 2H), 2.32 (t, J=7.4 Hz, 2H), 3.58-3.66 (m, 1H), 3.88-4.00 (m, 1H), 4.93 (br, 1H), 8.96 (br, 1H), 10.12 (br, 1H); IR (ATR) $v_{max}/cm^1$3200 br, 2938, 2860 w, 1707 s, 1644 s, 1455 m, 1357 m, 1204 s, 1035 s, 871 s; MS(ES): m/z=296.1 $[M+H]^+$; HRMS (ES) calcd. for $C_{13}H_{23}NO_5Na$ $[M+H]^+$: 296.1468, found 296.1466.

1.1.28 Synthesis of methyl (2E)-3-(5-{2-[4-(4-{7-[(oxan-2-yloxy)carbamoyl]heptanoyl}piperazin-1-yl)phenyl]ethynyl}pyridin-2-yl)prop-2-enoate, 50

The synthesis of methyl (2E)-3-(5-{2-[4-(4-{7-[(oxan-2-yloxy)carbamoyl]heptanoyl}piperazin-1-yl)phenyl] ethynyl}pyridin-2-yl)prop-2-enoate (50) is shown in FIG. 1(*xxii*). Compound 49 (0.88 g, 3.23 mmol) and 2-chloro-4,6-dimethoxy-1,3,5-triazine (0.71 g, 4.03 mmol) was dissolved in DCM (60 mL) at 0° C., whereupon 4-methylmorpholine (0.44 mL, 4.03 mmol) was added dropwise over 5 min. The resultant mixture was stirred at 0° C. for 2 h whereupon compound 43 (1.07 g, 3.08 mmol) and 4-methylmorpholine (0.41 mL, 3.63 mmol) were added and the mixture was stirred for 16 h at RT. The mixture was diluted with DCM, washed with $H_2O$, dried ($MgSO_4$) and evaporated to give a crude yellow solid (1.31 g). This was purified by $SiO_2$ chromatography (98:2, DCM/MeOH) to give compound 50 as a yellow solid (1.25 g, 67%): $^1H$ NMR (700 MHz, $CDCl_3$) δ 1.29-1.42 (m, 4H), 1.55-1.67 (m, 7H), 1.70-1.87 (m, 3H), 2.01-2.19 (m, 2H), 2.35 (t, J=7.6 Hz, 2H), 3.22 (t, J=5.3 Hz, 2H), 3.26 (t, J=5.3 Hz, 2H), 3.57-3.64 (m, 3H), 3.76 (t, J=5.3 Hz, 2H), 3.80 (s, 3H), 3.91-3.98 (m, 1H), 4.94 (s, 1H), 6.81-6.88 (m, 2H), 6.90 (d, J=15.7 Hz, 1H), 7.36 (dd, J=8.0, 0.8 Hz, 1H), 7.41-7.46 (m, 2H), 7.65 (d, J=15.7 Hz, 1H), 7.75 (dd, J=8.0, 2.2 Hz, 1H), 8.66-8.74 (m, 1H), 8.75-8.94 (m, 1H); $^{13}C$ NMR (176 MHz, $CDCl_3$) δ 18.7, 25.0, 25.2, 28.1, 28.7, 28.9, 33.1, 33.2, 41.3, 45.4, 48.3, 48.6, 52.0, 62.6, 85.2, 95.2, 102.5, 113.0, 115.5, 121.6, 122.3, 123.7, 133.1, 138.7, 143.0, 151.0, 151.1, 152.4, 167.3, 171.8; IR (ATR) $v_{max}/cm^{-1}$ 3217 br, 3000 w, 2945 m, 2856 w 2211 w, 1738 s, 1640 s, 1605 s, 1577 m, 1516 s, 1437 s, 1366 s, 1231 s, 820 s; MS(ES): m/z=603.2 $[M+H]^+$; HRMS (ES) calcd. for $C_{34}H_{42}N_4O_6$ $[M+H]^+$: 603.3177, found 603.3178.

1.1.29 Synthesis of 2-methylpropyl (2E)-3-(5-{2-[4-(4-{7-[(oxan-2-yloxy)carbamoyl]heptanoyl}piperazin-1-yl)phenyl]ethynyl}pyridin-2-yl)prop-2-enoate, 54

The synthesis of 2-methylpropyl (2E)-3-(5-{2-[4-(4-{7-[(oxan-2-yloxy)carbamoyl]heptanoyl}piperazin-1-yl)phenyl]ethynyl}pyridin-2-yl)prop-2-enoate (54) is shown in FIG. 1(*xxiii*). Compound 49 (0.54 g, 1.97 mmol) and 2-chloro-4,6-dimethoxy-1,3,5-triazine (0.45 g, 2.58 mmol) was dissolved in DCM (50 mL) at 0° C., whereupon 4-methylmorpholine (0.32 mL, 2.97 mmol) was added dropwise over 5 mins. The resultant mixture was stirred at 0° C. for 2 h whereupon compound 46 (0.56 g, 1.44 mmol) and 4-methylmorpholine (0.32 mL, 2.97 mmol) were added and the mixture was stirred for 16 h at RT. The mixture was diluted with DCM, washed with $H_2O$, dried ($MgSO_4$) and evaporated to give a crude yellow solid (1.7 g). This was purified by $SiO_2$ chromatography (98:2, DCM/MeOH) to give compound 54 as a yellow solid (0.55 g, 59%): $^{1}$H NMR (700 MHz, $CDCl_3$) δ 0.98 (d, J=6.8 Hz, 6H), 1.35-1.40 (m, 4H), 1.50-1.61 (m, 3H), 1.63-1.67 (m, 4H), 1.74-1.86 (m, 3H), 2.01 (hept, J=6.8 Hz, 1H), 2.07-2.20 (m, 2H), 2.37 (t, J=7.5 Hz, 2H), 3.24 (t, J=5.3 Hz, 2H), 3.27 (t, J=5.3 Hz, 2H), 3.61-3.64 (m, 3H), 3.78 (t, J=5.3 Hz, 2H), 3.92-3.97 (m, 1H), 4.00 (d, J=6.6 Hz, 2H), 4.95 (s, 1H), 6.85-6.89 (m, 2H), 6.93 (d, J=15.8 Hz, 1H), 7.39 (d, J=8.0 Hz, 1H), 7.44-7.48 (m, 2H), 7.66 (d, J=15.8 Hz, 1H), 7.77 (dd, J=8.0, 2.1 Hz, 1H), 8.57 (s, 1H), 8.73 (d, J=2.1 Hz, 1H); $^{13}$C NMR (176 MHz, $CDCl_3$) δ 19.1, 24.9, 25.0, 27.8, 28.0, 28.5, 28.7, 32.9, 41.2, 45.2, 48.2, 48.5, 62.5, 70.8, 85.0, 95.0, 102.4, 112.9, 115.4, 121.4, 122.7, 123.4, 133.0, 138.6, 142.5, 150.8, 151.1, 152.2, 166.7, 171.6; (ATR) $v_{max}/cm^{-1}$ 3191 br, 2940 m, 2857 w, 2209 w, 1708 s, 1641 s, 1605 s, 1517 s, 1234 s, 1204 s, 1021 s, 753 m; MS(ES): m/z=645.3 $[M+H]^+$; HRMS (ES) calcd. for $C_{37}H_{49}N_4O_6$ $[M+H]^+$: 645.3647, found 645.3647.

1.1.30 Synthesis of tert-butyl (2E)-3-(4-{2-[4-(4-{7-[(oxan-2-yloxy)carbamoyl]heptanoyl}piperazin-1-yl)phenyl]ethynyl}phenyl)prop-2-enoate, 56

The synthesis of tert-butyl (2E)-3-(4-{2-[4-(4-{7-[(oxan-2-yloxy)carbamoyl]heptanoyl}piperazin-1-yl)phenyl]ethynyl}phenyl)prop-2-enoate (56) is shown in FIG. 1(*xxiv*). Compound 49 (0.22 g, 0.80 mmol) and 2-chloro-4,6-dimethoxy-1,3,5-triazine (0.18 g, 1.00 mmol) were dissolved in DCM (30 mL), and the solution was cooled to 0° C. 4-Methylmorpholine (0.11 mL, 1.00 mmol) was added dropwise over 5 min, and the resultant solution was stirred at 0° C. for 2 h, whereupon compound 6 (0.3 g, 0.77 mmol) and 4-methylmorpholine (0.1 mL, 0.90 mmol) were added and the solution was further stirred for 18 h. The solution was diluted with DCM, washed with $H_2O$, dried ($MgSO_4$) and evaporated to give a crude yellow solid (0.62 g). This was purified by $SiO_2$ chromatography (97:3 to 95:5, DCM/MeOH) to give compound 56 as a yellow solid (0.30 g, 61%): $^{1}$H NMR (400 MHz, $CDCl_3$) δ 1.31-1.43 (m, 4H), 1.53 (s, 9H), 1.55-1.72 (m, 7H), 1.74-1.89 (m, 3H), 2.13 (s, 2H), 2.37 (t, J=7.5 Hz, 2H), 3.19-3.32 (m, 4H), 3.56-3.70 (m, 3H), 3.79 (t, J=5.1 Hz, 3H), 3.87-4.01 (m, 1H), 4.95 (s, 1H), 6.37 (d, J=16.0 Hz, 1H), 6.89 (d, J=8.5 Hz, 2H), 7.39-7.53 (m, 6H), 7.56 (d, J=16.0 Hz, 1H), 8.48 (s, 1H); $^{13}$C NMR (176 MHz, $CDCl_3$) δ 18.5, 24.9, 25.0, 28.0, 28.2, 28.5, 28.7, 32.9, 33.1, 41.2, 45.3, 48.4, 48.7, 62.5, 80.6, 88.0, 91.9, 102.4, 113.8, 115.5, 120.6, 125.3, 127.8, 129.1, 130.4, 131.7, 132.8, 134.0, 142.7, 150.6, 166.2, 170.5, 171.6; IR (ATR) $v_{max}/cm^{-1}$ 3218 br, 2933 m, 2855 w, 2209 w, 1700 s, 1633 s, 1596 s, 1520 s, 1518 m, 1440 m, 1325 m, 1234 s, 1207 s, 1153 s, 1159 m, 1128 m, 1036 s, 820 s; MS(ES): m/z=644.4 $[M+H]^+$; HRMS (ES) calcd. for $C_{38}H_{50}N_3O_6$ $[M+H]^+$: 644.3700, found 644.3675.

1.1.31 Synthesis of tert-butyl (2E)-3-(5-{2-[4-(4-{7-[(oxan-2-yloxy)carbamoyl]heptanoyl}piperazin-1-yl)phenyl]ethynyl}thiophen-2-yl)prop-2-enoate 58

The synthesis of tert-butyl (2E)-3-(5-{2-[4-(4-{7-[(oxan-2-yloxy)carbamoyl]heptanoyl}piperazin-1-yl)phenyl]ethynyl}thiophen-2-yl)prop-2-enoate (58) is shown in FIG. 1(*xxv*). Compound 49 (0.22 g, 0.80 mmol) and 2-chloro-4,6-dimethoxy-1,3,5-triazine (0.18 g, 1.00 mmol) were dissolved in DCM (30 mL), and the solution was cooled to 0° C. 4-Methylmorpholine (0.11 mL, 1.00 mmol) was added dropwise over 5 min, and the resultant solution was stirred at 0° C. for 2 h, whereupon compound 27 (0.3 g, 0.76 mmol) and 4-methylmorpholine (0.1 mL, 0.90 mmol) were added and the solution was further stirred for 20 h. The solution was diluted with DCM, washed with $H_2O$, dried ($MgSO_4$) and evaporated to give a crude orange oil (0.6 g). This was purified by $SiO_2$ chromatography (97:3 to 95:5, DCM/MeOH) to give compound 58 as a yellow oil (0.32 g, 65%): $^{1}$H NMR (400 MHz, $CDCl_3$) δ 1.34-1.40 (m, 4H), 1.51 (s, 9H), 1.59-1.69 (m, 6H), 1.75-1.84 (m, 4H), 2.12 (s, 2H), 2.32-2.41 (m, 2H), 3.20-3.29 (m, 4H), 3.59-3.65 (m, 3H), 3.77 (t, J=5.2 Hz, 2H), 3.87-4.00 (m, 1H), 4.94 (s, 1H), 6.12 (d, J=15.6 Hz, 1H), 6.79-6.91 (m, 2H), 7.06-7.14 (m, 2H), 7.38-7.45 (m, 2H), 7.59 (d, J=15.6 Hz, 1H), 8.70 (s, 1H); $^{13}$C NMR (176 MHz, $CDCl_3$) δ 18.6, 24.9, 25.0, 25.2, 28.0, 28.1, 28.2, 28.2, 28.5, 28.7, 32.9, 33.0, 41.2, 45.2, 48.2, 48.5, 51.5, 56.0, 62.5, 63.8, 80.6, 81.4, 96.0, 102.4, 113.0, 115.4, 119.3, 126.2, 130.6, 132.0, 132.7, 135.5, 140.3, 150.7, 165.9, 170.5, 171.7; IR (ATR) $v_{max}/cm^{-1}$ 3233 br, 2934 m, 2860 w, 2203 w, 1700 s, 1674 s, 1620 s, 1604 s, 1513 m, 1442 m, 1368 s, 1232 s, 1150 s, 1036 m, 655 s; MS(ES): m/z=650.3 $[M+H]^+$; HRMS (ES) calcd. For $C_{36}H_{48}N_3O_6S$ $[M+H]^+$: 650.3264, found 650.3262.

1.1.32 Synthesis of methyl (2E)-3-4-[2-(trimethylsilyl)ethynyl]phenylprop-2-enoate, 60

The synthesis of methyl (2E)-3-4-[2-(trimethylsilyl)ethynyl]phenylprop-2-enoate (60) is shown in FIG. 1(*xxvi*). Anhydrous THF (10 mL) was added into a Schlenk round bottom flask followed by the addition of methyl 2-(diethoxyphosphoryl)acetate (1.4 mL, 6 mmol) and LiCl (0.25 g, 5.9 mmol). The resulting reaction mixture was stirred at 0° C. for 15 mins. Compound 1 (1 g, 4.9 mmol) was then added, followed by the slow addition of DBU (0.81 mL, 5.4 mmol). The reaction mixture was allowed to warm to RT and further stirred for 16 h. The reaction mixture was poured into crushed ice and extracted with EtOAc, the organic extracts were washed with $H_2O$ and brine, dried over $MgSO_4$ and evaporated to give a light brown solid crude (1.4 g). The crude was purified by $SiO_2$ column chromatography (Pet. Et:EtOAc, 9:1 as eluent) to give compound 60 as a white solid (87.2 mg, 69%): $^{1}$H NMR (CDCl3, 400 MHz) δ 0.25 (s, 9H), 3.81 (s, 3H), 6.43 (d, J 16 Hz, 1H), 7.43-7.49 (m, 4H), 7.65 (d, J 16 Hz, 1H); $^{13}$C NMR (101 MHz, $CDCl_3$) δ 167.38, 144.03, 134.45, 132.54, 127.99, 125.16, 118.69, 104.61, 96.87, 51.93, 0.32, 0.04.

1.1.33 Synthesis of methyl (2E)-3-(4-ethynylphenyl)prop-2-enoate, 5

The synthesis of methyl (2E)-3-(4-ethynylphenyl)prop-2-enoate (5) is shown in FIG. 1(*xxvi*). MeOH:DCM (1:3, 2 mL) was added into a round bottom flask, followed by the addition of compound 60 (0.87 g, 3.4 mmol) and $K_2CO_3$ (0.7 g, 5.06 mmol). The reaction mixture was stirred at RT for 3 h. The resulting solution was then diluted in DCM and the organics were washed with $NH_4Cl$ (sat) and $H_2O$, dried over $MgSO_4$ and evaporated to give a crude white solid. The crude was then purified by recrystallisation from heptane to give compound 5 as a white crystalline solid (0.5 g, 77%): $^{1}$H NMR δ 3.18 (s, 1H), 3.81 (s, 3H), 6.42-6.46 (d, J 16.02 Hz, 1H), 7.48-7.50 (m, 4H), 7.64-7.68 (d, J 16.02 Hz, 1H); $^{13}$C NMR (101 MHz, $CDCl_3$) δ 167.32, 143.89, 134.84, 132.73, 128.05, 124.09, 118.97, 83.28, 79.35, 51.96.

1.1.34 Synthesis of 2-(2-methoxyethoxy)ethyl (2E)-3-(4-ethynylphenyl)prop-2-enoate, 61

The synthesis' of 2-(2-methoxyethoxy)ethyl (2E)-3-(4-ethynylphenyl)prop-2-enoate (61) is shown in FIG. 1(*xxvi*).

Compound 5 (22.5 mg, 0.12 mmol) was dissolved in diethylene glycol monomethyl ether (2 mL), followed by the addition of $K_2CO_3$ (1 mg, 0.007 mmol) and the reaction was then stirred at RT for 24 h. The resulting reaction mixture was diluted in $H_2O$ and extracted with DCM, the organic extracts were washed with $H_2O$, dried over $MgSO_4$ and evaporated yielding a crude yellow oil (157.8 mg). The crude product was then purified by Kugelrohr distillation (70-80° C., 9 Torr) to give compound 61 as a yellow oil (25.9 mg, 62%). $^1$H NMR ($CDCl_3$, 400 MHz) δ 3.18 (s, 1H), 3.40 (s, 3H), 3.56-3.59 (m, 2H), 3.67-3.70 (m, 2H), 3.77-3.80 (m, 2H), 4.37-4.40 (m, 2H), 6.48 (d, J=16 Hz, 1H), 7.45-7.51 (m, 4H), 7.67 (d, J=16 Hz, 1H); $^{13}$C NMR ($CDCl_3$, 101 MHz) δ 166.84, 144.06, 134.84, 132.73, 128.07, 124.08, 119.08, 83.28, 79.36, 72.05, 70.69, 69.42, 63.90, 59.27; MS (ESI) m/z=275.1 $[M+H]^+$; HRMS (ESI) calcd. For $C_{16}H_{19}O_4[M+H]^+$: 275.1283, found 275.1286.

1.1.35 Synthesis of 2-(2-methoxyethoxy)ethyl (2E)-3-(4-{2-[4-(4-{8-[(oxan-2-yloxy)aminol octanoyl}piperazin-1-yl)phenyl]ethynyl}phenyl) prop-2-enoate, 63

The synthesis of 2-(2-methoxyethoxy)ethyl (2E)-3-(4-{2-[4-(4-{8-[(oxan-2-yloxy)amino]octanoyl}piperazin-1-yl) phenyl]ethynyl}phenyl)prop-2-enoate (63) is shown in FIG. 1(*xxvii*). Compound 49 (328 mg, 1.20 mmol) and 2-chloro-4,6-dimethoxy-1,3,5-triazine (270 mg, 1.51 mmol) were added into a round bottom flask containing DCM (40 mL) and the resulting solution was cooled down to ° C., followed by the dropwise addition of 4-methylmorpholine (156 µL, 1.44 mmol). The reaction mixture was stirred at 0° C. until the total consumption of 2-chloro-4,6-dimethoxy-1,3,5-triazine. Compound 62 (500 mg, 1.15 mmol) and 4-methylmorpholine (156 µL, 1.44 mmol) were added and the reaction was then stirred at RT for 16 h. The resulting reaction mixture was diluted in DCM, washed with $H_2O$, dried over $MgSO_4$ and evaporated yielding a crude orange solid which was purified by $SiO_2$ chromatography (9:1, DCM/MeOH) to yield compound 62 as an orange solid (0.5 g, 65%). $^1$H NMR ($CDCl_3$, 400 MHz) δ 1.41-1.34 (m, 6H), 1.70-1.63 (m, 6H), 3.21-3.28 (m, 4H), 3.57-3.59 (m, 2H), 3.61-3.66 (m, 4H), 3.68-3.70 (m, 2H), 3.71-3.73 (m, 1H), 3.77-3.81 (m, 4H), 3.83-3.86 (m, 2H), 3.95 (s, 3H), 4.36-4.41 (m, 2H), 4.95 (s, br, 1H), 6.48 (d J 15.9 Hz, 1H), 6.88 (d J 8.8 Hz, 2H), 7.44-7.46 (m, 2H), 7.47-7.51 (m, 4H), 7.68 (d J 15.9 Hz, 1H).

1.1.36 Synthesis of 6-[2-(trimethylsilyl)ethynyl] pyridine-3-carbaldehyde, 65

The synthesis of 6-[2-(trimethylsilyl)ethynyl]pyridine-3-carbaldehyde (65) is shown in FIG. 1(*xxviii*). 2-Chloropyridine-3-carboxaldehyde (10 g, 70.6 mmol), trimethylsilylacetylene (13.7 mL, 99.5 mmol), $Na_2PdCl_4$ (0.41 g, 1.4 mmol), CuI (0.2 g, 1.06 mmol), $PtBu_3HBF_4$ (0.81 g, 2.8 mmol) and $Na_2CO_3$ (11.13 g, 105 mmol) were added into a round bottom flask containing toluene (150 mL) previously sparged with Ar. The reaction mixture was stirred at 100° C. for 20 h. After evaporating, the reaction crude mixture was purified by $SiO_2$column chromatography (Petroleum ether: EtOAc, 7:3 as eluent), to yield compound 65 as a brown solid (4.4 g, 31%). $^1$H NMR (400 MHz, $CDCl_3$) δ 0.30 (s, 9H), 7.60 (d J 7.5 Hz, 1H), 8.12 (dd J 8.1, 2.1 Hz, 1H), 9.0 (dd J 2.1, 0.8 Hz, 1H), 10.1(s, 1H).

1.1.37 Synthesis of 6-ethynylpyridine-3-carbaldehyde, 66

The synthesis of 6-ethynylpyridine-3-carbaldehyde (66) is shown in FIG. 1(*xxviii*).

Compound 65 (4.4 g, 21.64 mmol) was dissolved in MeOH:DCM (1:3, 180 mL), followed by the addition of $K_2CO_3$ (3.23 g, 23.4 mmol). The reaction mixture was stirred at RT for 2 h. The reaction crude was then dissolved in DCM and washed with $NH_4Cl$ and $H_2O$, dried over $MgSO_4$ and evaporated. After Kugelrohr distillation at 150° C. (9 Torr) pure compound 66 was obtained as an off-white solid (1.4 g, 45%). $^1$H NMR (400 MHz, $CDCl_3$) δ 3.41 (s, 1H), 7.64 (d J 8.0 Hz, 1H), 8.15 (dd J 8.0, 2.1 Hz, 1H), 9.05 (dd J 2.1, 0.8 Hz, 1H), 10.12 (s, 1H).

1.1.38 Synthesis of diethyl ((iso-butoxycarbonyl)methyl) phosphonate, 67

The synthesis of diethyl ((iso-butoxycarbonyl)methyl) phosphonate (67) is shown in FIG. 1 (xxix). 2-Methyl-1-propanol (0.74 mL, 8.0 mmol) was added into a Schlenk round bottom flask under Ar containing anhydrous toluene (40 mL), followed by the addition of diethylphosphonoacetic acid (1.35 mL, 8.4 mmol), DIPEA (3.62 mL, 20.8 mmol) and propyl phosphonic anhydride (6.62 mL, 10.4 mmol). The resulting reaction mixture was stirred at RT for 4 h. The reaction crude mixture was then diluted with $H_2O$ and the organics were extracted with EtOAc. The combined organic extracts were washed with HCl (10% aq.), $NaHCO_3$ (sat.) and brine, dried over $MgSO_4$ and evaporated. Compound 67 (1.92 g, 95%) was used in further steps without purification. $^1$H NMR (400 MHz, $CDCl_3$) d 0.94 (d J 6.7 Hz, 6H), 1.34 (t J 14.1, 7.0 Hz, 6H), 1.90-2.00 (m, 1H), 2.97 (d J 21.6 Hz, 2H), 3.92 (dd J 6.7, 0.5 Hz, 2H), 4.13-4.21 (m, 4H).

1.1.39 Synthesis of 2-methylpropyl (2E)-3-(6-ethynylpyridin-3-yl)prop-2-enoate, 68

The synthesis of 2-methylpropyl (2E)-3-(6-ethynylpyridin-3-yl)prop-2-enoate (68) is shown in FIG. 1(*xxx*). Compound 67 (1.92 g, 7.6 mmol) and LiCl (0.314 g, 7.41 mmol) were added into a Schlenk round bottom flask under Ar containing anhydrous THF (10 mL), the resulting reaction mixture was cooled down to 0° C. and stirred for 15 mins. Compound 66 (0.810 g, 6.18 mmol) was then added, followed by the drop-wise addition of DBU (1.01 mL, 6.8 mmol). The reaction mixture was allowed to warm to RT and continued to stir for further 16 h. The reaction crude was poured into crushed ice and extracted with EtOAc, the organic extracts were washed with brine, dried over $MgSO_4$ and evaporated. Purification by $SiO_2$ column chromatography yielded compound 68 as a bright yellow solid (1.3 g, 92%). 1H NMR (400 MHz, $CDCl_3$) d 0.99 (d J 6.7 Hz, 6H), 1.97-2.07 (m, 1H), 3.27 (s, 1H), 4.01 (d J 6.7 Hz, 2H), 6.54 (d J 16.1 Hz, 1H), 7.50 (d J 8.2 Hz, 1H), 7.65 (d J 16.1 Hz, 1H), 7.82 (dd J 8.2, 2.2 Hz, 1H), 8.72 (d J 2.2 Hz, 1H); $^{13}$C NMR (101 MHz, $CDCl_3$) δ 166.31, 149.86, 143.29, 139.98, 134.56, 130.11, 127.61, 121.54, 82.51, 79.33, 71.19, 27.95, 19.28; HRMS (ESI) calcd. for $C_{14}H_{16}NO_2$ $[M+H]^+$: 230.1181, found 230.1181.

1.1.40 Synthesis of 2-methylpropyl (2E)-3-(6-{2-[4-(4-{7-[(oxan-2-yloxy)carbamoyl] heptanoyl}piperazin-1-yl) phenyl]ethynyl}pyridin-3-yl)prop-2-enoate, 70

The synthesis of 2-methylpropyl (2E)-3-(6-{2-[4-(4-{7-[(oxan-2-yloxy)carbamoyl]heptanoyl}piperazin-1-yl) phenyl]ethynyl}pyridin-3-yl)prop-2-enoate (70) is shown in FIG. 1(*xxxi*). Compound 49 (370 mg, 1.34 mmol) and 2-chloro-4,6-dimethoxy-1,3,5-triazine (300 mg, 1.7 mmol) were dissolved in DCM and the resulting solution was cooled down to 0° C. followed by the drop-wise addition of 4-Methylmorpholine (250 mL, 2.27 mmol), the reaction mixture was continued to stir at 0° C. for 4 h. Compound 69 (500 mg, 1.28 mmol) and 4-methylmorpholine (102 mL, 0.92 mmol) were then added and the resulting reaction mixture was allowed to warm to RT and continued to stir overnight. The resulting reaction mixture crude was diluted in DCM, washed with $H_2O$, dried over $MgSO_4$ and evaporated to give a crude yellow solid (1 g). This was then purified by $SiO_2$ column chromatography (DCM:MeOH, 9:1) to yield compound 70 as a bright yellow solid (0.6 g, 72%): $^1$H NMR (400 MHz, $CDCl_3$) δ 0.99 (d J 6.7 Hz, 6H), 1.33-1.42 (m, 6H), 1.64-1.71 (m, 6H), 1.76-1.87 (m, 4H), 1.99-2.06 (m, 1H), 2.10-2.17 (m, 2H), 3.24-3.32 (m, 4H), 3.60-3.67 (m, 4H), 3.71-3.74 (m, 1H), 3.84-3.87 (m, 1H), 4.01 (d J 6.7 Hz, 2H), 4.95 (s, 1H), 6.53 (d J 16 Hz, 1H), 7.66 (d 116 Hz, 1H), 7.52-7.56 (m, 1H), 7.84 (d J 8.3 Hz, 1H), 8.72 (d J 2.1 Hz, 1H), 6.89 (d J 8.8 Hz, 2H), 7.50-7.54 (m, 2H).

1.1.41 Synthesis of 1-(4-iodophenyl)-4-methylpiperazine, 72

The synthesis of 1-(4-iodophenyl)-4-methylpiperazine (72) is shown in FIG. 1(*xxxii*).

Compound 4 (2.88 g, 10.0 mmol) was dissolved in DMF (20 mL) under Ar whereupon iodomethane (0.93 mL, 15.0 mmol) and $Et_3N$ (2.09 mL, 15.0 mmol) were added and the solution was stirred at RT for 72 h. $H_2O$ was added and the resultant precipitate was filtered to give a crude beige solid (6.4 g). This was purified by $SiO_2$ chromatography (DCM/MeOH, 9:1) to give compound 72 as an off-white solid (1.22 g, 40%): $^1$H NMR (400 MHz, $CDCl_3$) δ 2.34 (s, 3H), 2.51-2.58 (m, 4H), 3.13-3.21 (m, 4H), 6.64-6.71 (m, 2H), 7.46-7.55 (m, 2H); $^{13}$C NMR (101 MHz, $CDCl_3$) δ 46.1, 48.6, 54.9, 81.3, 118.0, 137.7, 150.8; IR (ATR) $v_{max}$/cm$^{-1}$ 2959 w, 2832 m, 2793 m, 1672 m, 1490 s, 1447 m, 1390 m, 1292 s, 1235 s, 1144 s, 1009 m, 908 s, 811 s; MS(ES): m/z=303.0 [M+H]$^+$; HRMS (ES) calcd. for $C_{11}H_{15}N_2I$ [M+H]$^+$: 303.0353, found 303.0351.

1.1.42 Synthesis of 1-methyl-4-(2-nitrophenyl)piperazine, 74

The synthesis of 1-methyl-4-(2-nitrophenyl)piperazine (74) is shown in FIG. 1(*xxxiii*). 1-Fluoro-2-nitrobenzene (9 mL, 85.0 mmol) was added to DMSO (60 mL), whereupon N-methylpiperazine (18.9 mL, 170.0 mmol), and $K_2CO_3$ (23.4 g, 170 mmol) were added. The resultant red solution was stirred at 110° C. for 24 h, before being cooled and diluted with $H_2O$. The mixture was extracted with DCM (3×), washed with sat. $NH_4Cl$ and $H_2O$, dried ($MgSO_4$) and evaporated to give compound 74 as a red oil that was carried directly to the next step (21.0 g, >100%): $^1$H NMR (300 MHz, $CDCl_3$) δ 2.35 (s, 3H), 2.52-2.60 (m, 4H), 3.03-3.14 (m, 4H), 6.98-7.06 (m, 1H), 7.14 (dd, J=8.2, 1.7 Hz, 1H), 7.40-7.53 (m, 1H), 7.75 (dd, J=8.2, 1.7 Hz, 1H).

1.1.43 Synthesis of 2-(4-methylpiperazin-1-yl)aniline, 75

The synthesis of 2-(4-methylpiperazin-1-yl)aniline (75) is shown in FIG. 1(*xxxiii*). Compound 74 (21.0 g, 85.0 mmol) was dissolved in EtOH (200 mL), whereupon concentrated hydrochloric acid (c. HCl) (20 mL) and Sn(II)$Cl_2$ (48.4 g, 255.0 mmol) were added and the resultant mixture was stirred at reflux for 18 h. The mixture was cooled, and the solvent evaporated to give a crude residue which was dissolved in DCM. The organics were washed with 5% NaOH and $H_2O$, dried ($MgSO_4$) and evaporated to give a crude yellow solid (4.7 g). This was purified by $SiO_2$ chromatography (9:1, DCM/MeOH) to give compound 75 as a yellow solid (3.08 g, 19%): $^1$H NMR (400 MHz, $CDCl_3$) δ 2.36 (s, 3H), 2.45-2.65 (m, 4H), 2.95 (t, J=4.9 Hz, 4H), 3.96 (br, 2H), 6.68-6.77 (m, 2H), 6.93 (td, J=7.7, 1.2 Hz, 1H), 7.02 (dd, J=7.7, 1.2 Hz, 1H); $^{13}$C NMR (101 MHz, $CDCl_3$) δ 46.2, 50.9, 55.9, 115.0, 118.5, 119.8, 124.5, 139.1, 141.4; IR (ATR) $v_{max}$/cm$^{-1}$ 13389 m, 3294 w, 2939 w, 2980 w, 1619 s, 1503 s, 1449 s, 1283 s, 1139 s, 1011 s, 927 m.

1.1.44 Synthesis of 1-(2-iodophenyl)-4-methylpiperazine, 76

The synthesis of 1-(2-iodophenyl)-4-methylpiperazine (76) is shown in FIG. 1(*xxxiii*).

Compound 75 (2.0 g, 10.4 mmol) was dissolved in c. HCl (3 mL) and $H_2O$ (12 mL) and the resultant solution was cooled to 0° C. $NaNO_2$ (0.86 g, 12.5 mmol, solution in 3 mL $H_2O$) was added slowly over 2 mins and the resultant suspension was stirred at 0° C. for 2 h, whereupon KI (3.45 g, 20.8 mmol) was added portion-wise before the suspension was stirred at RT for 72 h. The suspension was extracted with DCM and washed with sat. $NaHCO_3$ and water, dried ($MgSO_4$) and evaporated to give a crude solid. This was purified by $SiO_2$ chromatography (9:1, DCM/MeOH) to give compound 76 as a dark solid (2.64 g, 84%): $^1$H NMR (300 MHz, $CDCl_3$) δ 2.54 (s, 3H), 2.90 (s, 4H), 3.18 (t, J=4.9 Hz, 4H), 6.81 (td, J=7.8, 1.5 Hz, 1H), 7.06 (dd, J=8.0, 1.5 Hz, 1H), 7.31 (ddd, J=8.0, 7.3, 1.5 Hz, 1H), 7.83 (dd, J=7.8, 1.5 Hz, 1H); $^{13}$C NMR (176 MHz, $CDCl_3$) δ 45.2, 51.0, 54.9, 98.0, 121.2, 125.9, 129.3, 139.9, 152.4; IR (ATR) $v_{max}$/cm$^{-1}$ 3006 w, 2879 m, 2833 m, 1738 w, 1579 w, 1468 s, 1461 s, 1371 s, 1289 m, 1230 s, 1145 s, 1012 s, 972 m, 762 m.

1.1.45 Synthesis of (3-chloro-2-oxopropyl)triphenylphosphonium chloride, 78

The synthesis of (3-chloro-2-oxopropyl)triphenylphosphonium chloride (78) is shown in FIG. 1(*xxxiv*). 1,3-Dichloroacetone (15.0 g, 118 mmol) and triphenylphosphine (31.0 g, 118 mmol) were dissolved in toluene (60 mL) and the suspension was stirred at RT for 72 h. The resultant suspension was filtered, and the isolated solid was washed with toluene and $Et_2O$ to give compound 78 as a white solid (43.1 g, 94%): $^1$H NMR (400 MHz, DMSO) δ 4.88 (s, 2H), 5.88 (d, J=12.8 Hz, 2H), 7.72-7.87 (m, 15H); all other data matched the literature (doi:10.1016/j.poly.2014.11.029).

1.1.46 Synthesis of 1-chloro-3-(triphenylphosphanylidene)propan-2-one, 79

The synthesis of 1-chloro-3-(triphenylphosphanylidene) propan-2-one (79) is shown in FIG. 1(*xxxiv*). Compound 78 (43.1 g, 110.7 mmol) was dissolved in MeOH (60 mL) whereupon $Na_2CO_3$ (5.87 g, 55.4 mmol, solution in 60 mL $H_2O$) was added and the resultant suspension was stirred rapidly for 0.5 h. The suspension was diluted with approx. 300 mL $H_2O$ and the mixture was filtered. The isolated solid was then dissolved in DCM, dried ($MgSO_4$) and evaporated to give compound 79 as a white solid (32.1 g, 82%): $^1H$ NMR (400 MHz, $CDCl_3$) δ 4.01 (s, 2H), 4.29 (d, J=24.0 Hz, 1H), 7.44-7.51 (m, 6H), 7.54-7.60 (m, 3H), 7.61-7.69 (m, 6H); all other data matched the literature (https://doi.org/10.1021/jo101864n).

1.1.47 Synthesis of (3E)-1-chloro-4-{5-[2-(trimethylsilyl)ethynyl]pyridin-2-yl}but-3-en-2-one, 80

The synthesis of (3E)-1-chloro-4-{5-[2-(trimethylsilyl)ethynyl]pyridin-2-yl}but-3-en-2-one (80) is shown in FIG. 1(*xxxiv*). Compound 40 (7.5 g, 36.9 mmol) and compound 79 (13.0 g, 36.9 mmol) were dissolved in DCM (60 mL) and the solution was stirred at RT for 48 h. The resultant dark solution was evaporated and the crude solid was purified by $SiO_2$ chromatography to give compound 80 as a white solid (7.67 g, 75%): $^1H$ NMR (400 MHz, $CDCl_3$) δ 0.27 (s, 9H), 4.32 (s, 2H), 7.40 (dd, J=8.1, 0.9 Hz, 1H), 7.44 (d, J=15.6 Hz, 1H), 7.65 (d, J=15.6 Hz, 1H), 7.77 (dd, J=8.1, 2.1 Hz, 1H), 8.69 (d, J=2.1 Hz, 1H); $^{13}C$ NMR (75 MHz, $CDCl_3$) δ −0.3, 47.8, 100.9, 101.2, 121.4, 124.4, 125.6, 139.5, 142.4, 151.1, 152.9, 191.2; IR (ATR) $v_{max}/cm^{-1}$ 3033 w, 2959 w, 2920 w, 2157 w, 1709 s, 1622 m, 1473 w, 1399 w, 1248 m, 981 m, 867 s, 841 s; MS(ES): m/z=278.1 $[M+H]^+$; HRMS (ES) calcd. for $C_{14}H_{17}NOCl$ $[M+H]^+$: 278.0768, found 278.0769.

1.1.48 Synthesis of 4-[(E)-2-{5-[2-(trimethylsilyl)ethynyl]pyridin-2-yl}ethenyl]-1,3-thiazol-2-amine, 81

The synthesis of 4-[(E)-2-{5-[2-(trimethylsilyl)ethynyl]pyridin-2-yl}ethenyl]-1,3-thiazol-2-amine (81) is shown in FIG. 1(*xxxiv*). Compound 80 (8.5 g, 30.6 mmol) and thiourea (2.8 g, 36.7 mmol) were dissolved in EtOH (70 mL) and the solution was stirred at reflux for 18 h. The mixture was cooled, and evaporated to give a crude residue that was purified by $SiO_2$ chromatography (1:1, cyclohexane/EtOAc) to give compound 81 as an off-white solid (4.24 g, 46%): $^1H$ NMR (400 MHz, $CDCl_3$) δ 0.25 (s, 9H), 6.83 (s, 1H), 7.08 (d, J=15.4 Hz, 1H), 7.12 (s, 2H), 7.41 (d, J=15.4 Hz, 1H), 7.46 (dd, J=8.1, 0.8 Hz, 1H), 7.80 (dd, J=8.1, 2.2 Hz, 1H), 8.58 (dd, J=2.2, 0.8 Hz, 1H); $^{13}C$ NMR (101 MHz, $CDCl_3$) δ 0.2, 89.2, 91.1, 98.1, 102.5, 109.6, 116.8, 121.7, 127.2, 127.4, 139.2, 149.2, 154.8, 168.1; IR (ATR) $v_{max}/cm^1$3305 br, 3117 br, 2959 w, 2899 w, 2157 m, 1724 m, 1628 m, 1582 m, 1536 m, 1504 m, 1471 m, 1367 m, 1249 s, 860 s, 842 s, 758 s; MS(ES): m/z=300.1 $[M+H]^+$; HRMS (ES) calcd. for $C_{15}H_{18}N_3SSi$ $[M+H]^+$: 300.0985, found 300.0985.

1.1.49 Synthesis of 4-[(E)-2-(5-ethynylpyridin-2-yl)ethenyl]-1,3-thiazol-2-amine, 82

The synthesis of 4-[(E)-2-(5-ethynylpyridin-2-yl)ethenyl]-1,3-thiazol-2-amine (82) is shown in FIG. 1(*xxxiv*). Compound 81 (5.0 g, 16.7 mmol) was dissolved in THF (80 mL) and the solution was cooled to −40° C. Tetrabutylammonium fluoride (TBAF) (18.3 mL, 18.3 mmol, 1.0 M in THF) was added dropwise, and the resultant solution was stirred at −40° C. for 1 h, and then allowed to reach RT. The solution was diluted with $H_2O$ and extracted with DCM. The organics were washed with $H_2O$, dried ($MgSO_4$) and evaporated to give a crude dark solid. This was purified by $SiO_2$ chromatography (cyclohexane/EtOAc, 1:1), to give compound 82 as a yellow solid (2.68 g, 71%): $^1H$ NMR (400 MHz, DMSO-$d_6$) δ 4.45 (s, 1H), 6.83 (s, 1H), 7.09 (d, J=15.4 Hz, 1H), 7.12 (s, 2H), 7.40 (d, J=15.4 Hz, 1H), 7.49 (dd, J=8.3, 0.9 Hz, 1H), 7.83 (dd, J=8.3, 2.2 Hz, 1H), 8.61 (dd, J=2.2, 0.9 Hz, 1H); $^{13}C$ NMR (101 MHz, DMSO-$d_6$) δ 80.9, 84.3, 109.5, 116.4, 121.6, 127.3, 139.4, 149.2, 152.0, 154.9, 168.1; IR (ATR) $v_{max}/cm^{-1}$ 3284 br, 3113 br, 3016 w, 2105 w, 1738 s, 1626 s, 1581 s, 1528 m, 1468 w, 1366 s, 1217 s, 917 m; MS(ES): m/z=228.1 $[M+H]^+$; HRMS (ES) calcd. for $C_{12}H_{10}N_3S$ $[M+H]^+$: 228.0590, found 228.0588.

1.1.50 Synthesis of 4-(4-iodophenyl)morpholine, 83

The synthesis of 4-(4-iodophenyl)morpholine (83) is shown in FIG. 1(*xxxv*). 4-Phenylmorpholine (12.5 g, 76.6 mmol) and $NaHCO_3$ (10.3 g, 122.6 mmol) were suspended in $H_2O$ (100 mL), and the mixture was cooled to ca. 12° C. Iodine (20.4 g, 80.4 mmol) was added slowly, and the resultant suspension was stirred rapidly at RT for 4 h. Sat. aq. $Na_2S_2O_3$ was added and the precipitated solid was isolated by filtration to give a crude dark grey solid (27 g). This was purified by recrystallisation from EtOH to give compound 83 as a grey solid (16.3 g, 74%): $^1H$ NMR (300 MHz, $CDCl_3$) δ 3.07-3.16 (m, 4H), 3.80-3.89 (m, 4H), 6.61-6.72 (m, 2H), 7.47-7.58 (m, 2H); $^{13}C$ NMR (176 MHz, $CDCl_3$) δ 48.8, 66.6, 81.7, 117.6, 137.8, 150.8; IR (ATR) $v_{max}/cm^{-1}$ 2966 w, 2890 w, 2856 w, 2829 w, 1583 m, 1490 m, 1258, 1234 s, 1118 s, 922 s, 811 s; MS(ES): m/z=290.0 $[M+H]^+$; HRMS (ES) calcd. for $C_{10}H_{13}NOI$ $[M+H]^+$: 290.0044, found 290.0037.

1.2 Preparation of Reference Compounds

1.2.1 Synthesis of methyl (2E)-3-(5-{2-[2-(4-methylpiperazin-1-yl)phenyl]ethynyl}pyridin-2-yl)prop-2-enoate, 77

The synthesis of methyl (2E)-3-(5-{2-[2-(4-methylpiperazin-1-yl)phenyl]ethynyl}pyridin-2-yl)prop-2-enoate (77) is shown in FIG. 1(*xxxiii*). $Et_3N$ (20 mL) was degassed by sparging with Ar for 1 h. Compound 76 (175 mg, 0.58 mmol), compound 42 (120 mg, 0.64 mmol), $Pd(PPh_3)_2Cl_2$ (21 mg, 0.03 mmol) and CuI (6 mg, 0.03 mmol) were then added under Ar and the resultant suspension was stirred at 60° C. for 18 h. The solvent was then evaporated to give a crude solid which was purified by $SiO_2$ chromatography (95:5, DCM/MeOH) to give compound 77 as a yellow oil (105 mg, 50%): $^1H$ NMR (400 MHz, $CDCl_3$) δ 2.39 (br, 3H), 2.68 (br, 4H), 3.29 (br, 4H), 3.82 (s, 3H), 6.94 (d, J=15.7 Hz, 1H), 6.96-7.00 (m, 2H), 7.28-7.35 (m, 1H), 7.40 (d, J=8.0 Hz, 1H), 7.51 (dd, J=7.8, 1.6 Hz, 1H), 7.68 (d, J=15.7 Hz, 1H), 7.79 (dd, J=8.0, 2.1 Hz, 1H), 8.76 (d, J=1.6 Hz, 1H); $^{13}C$ NMR (101 MHz, $CDCl_3$) δ 51.3, 51.9, 55.5, 91.2, 93.4, 115.7, 118.0, 121.4, 121.8, 122.4, 123.6, 130.3, 134.1, 138.6, 142.7, 151.3, 152.2, 154.3, 167.1; IR (ATR) $v_{max}/cm^{-1}$ 3006 w, 2879 m, 2833 m, 1738 w, 1579 w, 1468 s, 1461 s, 1371 s, 1289 m, 1230 s, 1145 s, 1012 s, 972 m, 762 m.

1.3 Preparation of Exemplary Compounds

1.3.1 Synthesis of tert-butyl (2E)-3-(4-{2-[4-(piperazin-1-yl)phenyl]ethynyl}phenyl)prop-2-enoate, 6

Figure 2I:
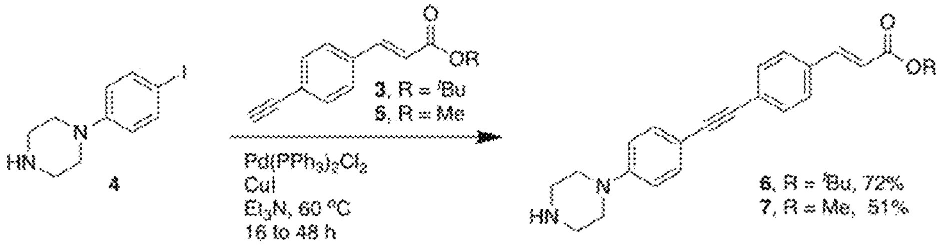
Figure 2:
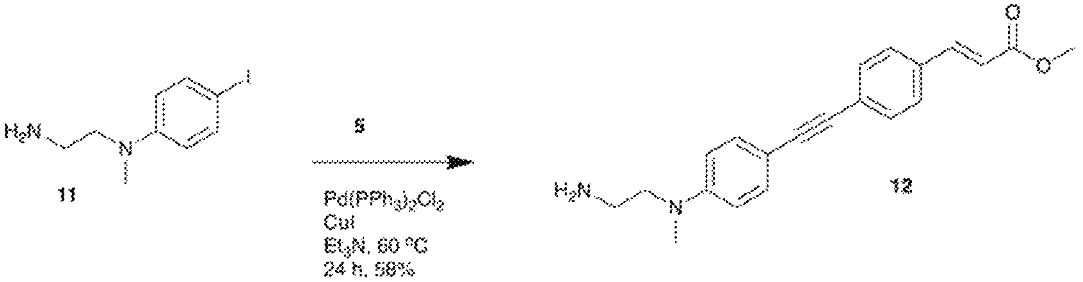
Figure 2:
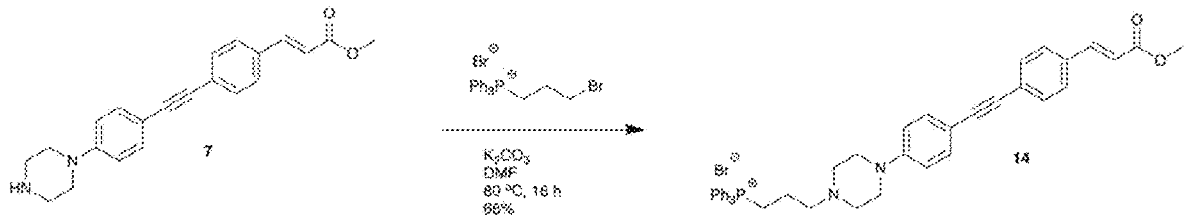
Figure 2V:
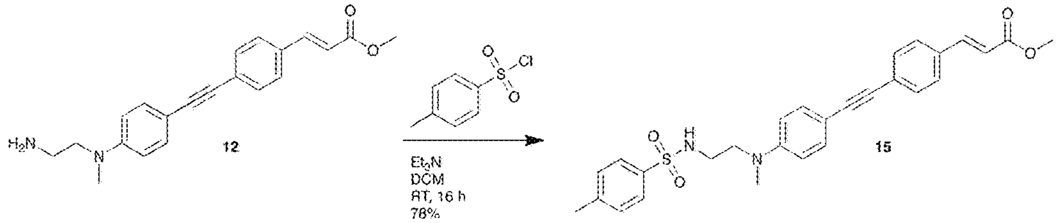
Figure 2:
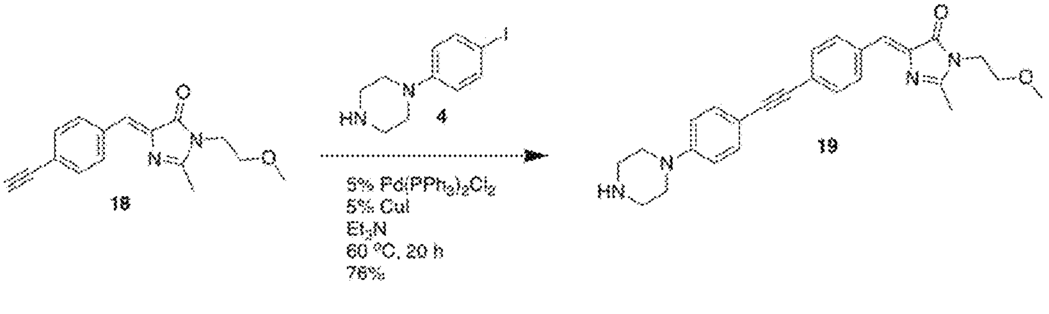
Figure 2:
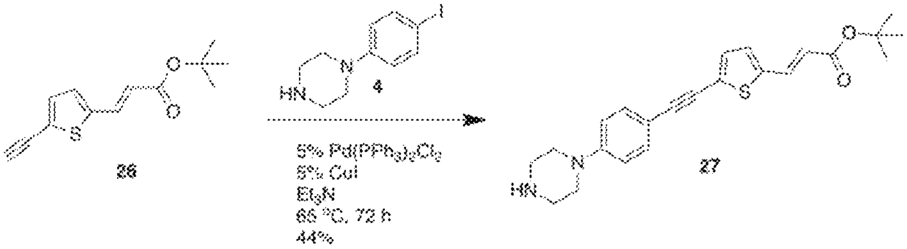
Figure 2:
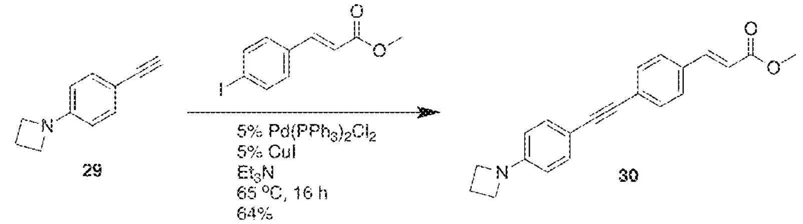
Figure 2X:
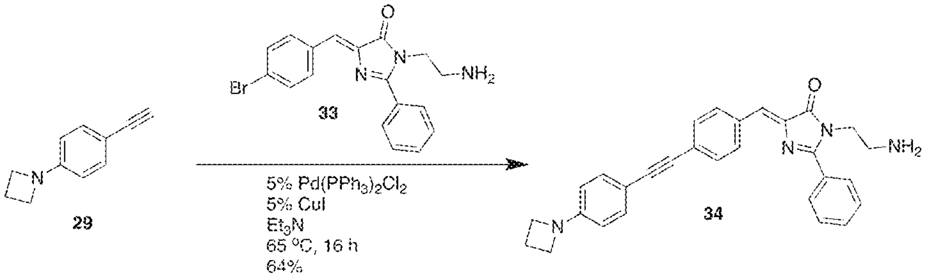
Figure 2:
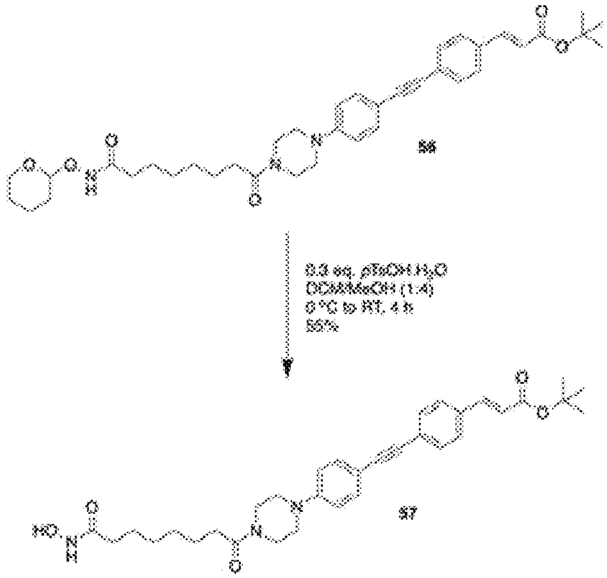

The synthesis of exemplary compound 6 is illustrated in FIG. 2(*i*). $Et_3N$ (80 mL) was degassed by sparging with Ar for 1 h. Compound 4 (2.16 g, 7.5 mmol), compound 3 (1.80 g, 7.88 mmol), $Pd(PPh_3)_2Cl_2$ (260 mg, 0.39 mmol) and CuI (71 mg, 0.39 mmol) were then added under Ar and the resultant suspension was stirred at 60° C. for 24 h. The solvent was then evaporated to give a crude solid which was purified by $SiO_2$ chromatography (9:1, DCM/MeOH, 1% $Et_3N$) and then recrystallization from MeOH to give compound 6 as a yellow solid (2.11 g, 72%): $^1H$ NMR (400 MHz, $CDCl_3$) δ 1.53 (s, 9H), 3.22-3.28 (m, 4H), 3.38-3.45 (m, 4H), 6.37 (d, J=15.9 Hz, 1H), 6.77-6.95 (m, 2H), 7.33-7.53 (m, 6H), 7.56 (d, J=15.9 Hz, 1H); IR (ATR) $v_{max}/cm^{-1}$ 2967 w, 2916 w, 2830 w, 2212 w, 1687 s, 1629 m, 1595 m, 1518 m, 1326 m, 1241 m, 1159 m, 1128 m, 986 m, 831 s, 819 s; MS(ASAP): m/z=389.2 $[M+H]^+$; HRMS (ASAP) calcd. for $C_{25}H_{29}N_2O_2$ $[M+H]^+$: 389.2229, found 389.2231.

1.3.2 Synthesis of methyl (2E)-3-(4-{2-[4-(piperazin-1-yl)phenyl]ethynyl}phenyl)prop-2-enoate, 7

The synthesis of exemplary compound 7 is illustrated in FIG. 2(*i*). $Et_3N$ (150 mL) was degassed by sparging with Ar for 1 h. Compound 4 (4.50 g, 15.6 mmol), compound 5 (3.05 g, 16.4 mmol), $Pd(PPh_3)_2Cl_2$ (550 mg, 0.78 mmol) and CuI (150 mg, 0.78 mmol) were then added under Ar and the resultant suspension was stirred at 60° C. for 24 h. The solvent was then evaporated to give a crude solid which was purified by $SiO_2$ chromatography (9:1, DCM/MeOH, 1% $Et_3N$) and then recrystallization from MeOH to give compound 7 as a yellow solid (2.74 g, 51%): $^1H$ NMR (600 MHz, DMSO-$d_6$) δ 2.82-2.94 (m, 4H), 3.14-3.24 (m, 4H), 3.73 (s, 3H), 6.67 (d, J=16.0 Hz, 1H), 6.94 (d, J=8.4 Hz, 2H), 7.39 (d, J=8.4 Hz, 2H), 7.52 (d, J=8.0 Hz, 2H), 7.67 (d, J=16.0 Hz, 1H), 7.74 (d, J=8.0 Hz, 2H); $^{13}C$ NMR (151 MHz, DMSO-$d_6$) δ 44.9, 47.5, 51.5, 87.6, 92.7, 110.7, 114.5, 118.3, 124.9, 128.6, 131.3, 132.5, 133.5, 143.6, 151.2, 166.6; IR (ATR) $v_{max}/cm^{-1}$ 3039 w, 2952 w, 2909 w, 2830 w, 2204 w, 2173 w, 1698 s, 1630 s, 1593 m, 1518 m, 1312 m, 1243 s, 1168 s, 987 m, 831 s, 817 s; MS(ASAP): m/z=347.2 $[M+H]^+$; HRMS (ASAP) calcd. for $C_{22}H_{23}N_2O_2$ $[M+H]^+$: 347.1760, found 347.1736.

1.3.3 Synthesis of methyl (2E)-3-[4-(2-{4-[(2-aminoethyl)(methyl)amino]phenyl}ethynyl) phenyl]prop-2-enoate, 12

The synthesis of methyl (2E)-3-[4-(2-{4-[(2-aminoethyl)(methyl)amino]phenyl}ethynyl) phenyl]prop-2-enoate, 12 is shown in FIG. 2(*ii*). Compound 11 (3.46 g, 12.53 mmol) was dissolved in $Et_3N$ (120 mL) and the solution was degassed by sparging with Ar for 1 h. Compound 5 (2.57 g, 13.8 mmol), $Pd(PPh_3)_2Cl_2$ (440 mg, 0.63 mmol) and CuI (120 mg, 0.63 mmol) were then added under Ar and the resultant suspension was stirred at 60° C. for 72 h. The solvent was then evaporated to give a crude solid which was purified by $SiO_2$ chromatography (9:1, DCM/MeOH, 0.5% $Et_3N$) to give compound 12 as a yellow solid (2.44 g, 58%): $^1H$ NMR (600 MHz, DMSO-$d_6$) δ 2.94 (t, J=7.0 Hz, 2H), 2.97 (s, 3H), 3.56 (t, J=7.0 Hz, 2H), 3.73 (s, 3H), 6.67 (d, J=16.0 Hz, 1H), 6.79 (d, J=9.0 Hz, 2H), 7.40 (d, J=8.9 Hz, 2H), 7.47-7.54 (m, 2H), 7.67 (d, J=16.0 Hz, 1H), 7.74 (d, J=8.3 Hz, 2H); $^{13}C$ NMR (151 MHz, DMSO-$d_6$) δ 36.3, 38.1, 49.6, 51.5, 78.7, 79.0, 79.2, 87.4, 93.1, 108.6, 111.9, 118.2, 118.2, 125.1, 128.6, 131.2, 132.7, 133.3, 143.6, 148.9, 166.6; IR (ATR) $v_{max}/cm^{-1}$ 3403 br, 3042 w, 2952 w, 2888 w, 2208 m, 1698 s, 1632 m, 1608 m, 1594 s, 1522 s, 1313 s, 1169 s, 1134 s, 817 s; MS(ASAP): m/z=335.2 $[M+H]^+$; HRMS (ASAP) calcd. for $C_{21}H_{23}N_2O_2[M+H]^+$: 335.1760, found 335.1743.

1.3.4 Synthesis of methyl (2E)-3-(4-{2-[4-(4-acetylpiperazin-1-yl)phenyl]ethynyl}phenyl) prop-2-enoate, 13

The synthesis of methyl (2E)-3-(4-{2-[4-(4-acetylpiperazin-1-yl)phenyl]ethynyl}phenyl) prop-2-enoate, 13 is shown in FIG. 2(*iii*). Compound 7 (0.35 g, 1.01 mmol) was dissolved in DCM (10 mL), whereupon acetyl chloride (86 μL, 1.21 mmol) and pyridine (98 μL, 1.21 mmol) were added and the resultant solution was stirred at RT for 16 h. The solution was diluted with DCM, washed with sat. $NH_4Cl$ and $H_2O$, dried ($MgSO_4$) and evaporated to give a crude yellow solid (0.4 g). This was purified by $SiO_2$ chromatography (97.5:2.5, DCM/MeOH) to give compound 13 as a yellow solid (0.38 g, 97%): $^1H$ NMR (600 MHz, $CDCl_3$) δ 2.15 (s, 3H), 3.24 (t, J=5.3 Hz, 2H), 3.27 (t, J=5.3 Hz, 2H), 3.63 (t, J=5.2 Hz, 2H), 3.78 (t, J=5.3 Hz, 2H), 3.81 (s, 3H), 6.44 (d, J=16.0 Hz, 1H), 6.88 (d, J=8.4 Hz, 2H), 7.41-7.47 (m, 2H), 7.46-7.54 (m, 4H), 7.67 (d, J=16.0 Hz, 1H); $^{13}C$ NMR (151 MHz, $CDCl_3$) δ 21.3, 41.1, 45.9, 48.3, 48.6, 51.7, 88.0, 92.1, 113.8, 115.6, 118.1, 125.7, 128.0, 131.8, 132.9, 133.7, 144.0, 150.5, 167.3, 169.0; IR (ATR) $v_{max}/cm^{-1}$ 3039 w, 2947 w, 2836 w, 2205 w, 2173 w, 1699 m, 1627 s, 1594 m, 1521 m, 1446 m, 1425 m, 1311 m, 1236 s, 1164 s, 994 s, 835 s, 822 s; MS(ASAP): m/z=388.2 $[M+H]^+$; HRMS (ASAP) calcd. for $C_{24}H_{24}N_2O_3$ $[M+H]^+$: 388.1787, found 388.1793.

1.3.5 Synthesis of (3-{4-[4-(2-{4-[(1E)-3-methoxy-3-oxoprop-1-en-1-yl]phenyl}ethynyl) phenyl]piperazin-1-yl}propyl)triphenylphosphonium bromide, 14

The synthesis of (3-{4-[4-(2-{4-[(1E)-3-methoxy-3-oxoprop-1-en-1-yl]phenyl}ethynyl) phenyl]piperazin-1-yl}propyl)triphenylphosphonium bromide, 14 is shown in FIG. 2(*iv*). Compound 7 (0.35 g, 1.01 mmol) was dissolved in anhydrous DMF (10 mL) under Ar, whereupon $K_2CO_3$ (0.167 g, 1.2 mmol) and (3-bromopropyl)triphenylphosphonium bromide (0.47 g, 1.01 mmol) were added and the resultant solution was stirred at 80° C. for 16 h. The solution was cooled, diluted with $H_2O$ and extracted with EtOAc. The organics were washed with $H_2O$ and brine, dried ($MgSO_4$) and evaporated to give a crude yellow solid (0.5 g). This was purified by $SiO_2$ chromatography (95:5, DCM/MeOH) and further recrystallisation from a DCM/heptane solution to give compound 14 as a yellow solid (0.44 g, 60%): $^1H$ NMR (600 MHz, $CDCl_3$) δ 1.82-1.91 (m, 2H), 2.52-2.58 (m, 4H), 2.74 (t, J=6.3 Hz, 2H), 3.16-3.23 (m, 4H), 3.79 (s, 3H), 3.91-3.99 (m, 2H), 6.41 (d, J=16.0 Hz, 1H), 6.77-6.84 (m, 2H), 7.32-7.42 (m, 2H), 7.39-7.52 (m, 4H), 7.64 (d, J=16.0 Hz, 1H), 7.66-7.73 (m, 6H), 7.75-7.81 (m, 3H), 7.81-7.90 (m, 6H); $^{13}C$ NMR (151 MHz, $CDCl_3$) δ 19.8 (d, J=3.2 Hz), 20.1 (d, J=51.8 Hz), 47.9, 51.7, 52.7, 57.1 (d, J=16.5 Hz), 87.6, 92.5, 112.7, 114.9, 117.9, 118.2, 118.7, 125.8, 127.9, 130.4 (d, J=12.5 Hz), 131.7, 132.7, 133.4, 133.6 (d, J=10.0 Hz), 135.0 (d, J=3.1 Hz), 144.0, 150.8, 167.3; IR (ATR) $v_{max}/cm^{-1}$ 3362 br, 2952 w, 2876 w, 2826 w, 2206 w, 1703 m, 1630 m, 1595 s, 1519 s, 1437 s, 1425 m, 1324 m, 1240 s, 1169 s, 1111 s, 996 s, 823 s; MS(ES): m/z=649.4 $[M]^+$; HRMS (ES) calcd. for $C_{43}H_{42}N_2O_2P$ $[M]^+$: 649.2984, found 649.2991.

1.3.6 Synthesis of methyl (2E)-3-{4-[2-(4-{methyl[2-(4-methylbenzenesulfonamido) ethyl]amino}phenyl)ethynyl]phenyl}prop-2-enoate, 15

The synthesis of methyl (2E)-3-{4-[2-(4-{methyl[2-(4-methylbenzenesulfonamido) ethyl]amino}phenyl)ethynyl]phenyl}prop-2-enoate, 15 is shown in FIG. 2(*v*). Compound 12 (0.35 g, 1.05 mmol) was dissolved in DCM (30 mL), whereupon p-toluenesulfonyl chloride (0.24 g, 1.26 mmol) and $Et_3N$ (0.18 mL, 1.26 mmol) were added and the resultant solution was stirred at RT for 16 h. The solution was diluted with DCM, washed with $H_2O$, dried ($MgSO_4$) and evaporated to give a crude yellow solid (0.5 g). This was purified by $SiO_2$ chromatography (99:1, DCM/MeOH) to give compound 15 as a yellow solid (0.47 g, 92%): $^1$H NMR (600 MHz, $CDCl_3$) δ 2.42 (s, 3H), 2.92 (s, 3H), 3.15 (q, J=6.4 Hz, 2H), 3.48 (t, J=6.4 Hz, 2H), 3.81 (s, 3H), 4.78 (t, J=6.4 Hz, 1H), 6.43 (d, J=16.0 Hz, 1H), 6.57-6.62 (m, 2H), 7.29 (d, J=8.1 Hz, 2H), 7.34-7.39 (m, 2H), 7.45-7.52 (m, 4H), 7.66 (d, J=16.0 Hz, 1H), 7.70-7.74 (m, 2H); $^{13}$C NMR (151 MHz, $CDCl_3$) δ 21.5, 38.6, 40.3, 51.7, 52.2, 87.5, 92.8, 110.5, 112.0, 117.9, 126.0, 127.0, 128.0, 129.8, 131.6, 133.0, 133.3, 136.7, 143.6, 144.1, 148.8, 167.4; IR (ATR) $v_{max}$/cm$^{-1}$ 3241 br, 2949 w, 2921 w, 2857 w, 2210 m, 1711 m, 1632 w, 1595 s, 1524 s, 1320 m, 1156 s, 1145 s, 819 s; MS(ASAP): m/z=489.2 $[M+H]^+$; HRMS (ASAP) calcd. for $C_{28}H_{29}N_2O_4S$ $[M+H]^+$: 489.1848, found 489.1866.

1.3.7 Synthesis of (4Z)-1-(2-methoxyethyl)-2-methyl-4-[(4-{2-[4-(piperazin-1-yl)phenyl ethynyl}phenyl)methylidene]-4,5-dihydro-1H-imidazol-5-one, 19

The synthesis of (4Z)-1-(2-methoxyethyl)-2-methyl-4-[(4-{2-[4-(piperazin-1-yl)phenyl]ethynyl}phenyl)methylidene]-4,5-dihydro-1H-imidazol-5-one, 19 is shown in FIG. 2(*vi*).

$Et_3N$ (90 mL) was degassed by sparging with Ar for 1 h. Compound 4 (1.43 g, 4.97 mmol), compound 18 (1.60 g, 5.96 mmol), $Pd(PPh_3)_2Cl_2$ (175 mg, 0.25 mmol) and CuI (48 mg, 0.25 mmol) were then added under Ar and the resultant suspension was stirred at 60° C. for 18 h. The suspension was diluted with $CHCl_3$, and the organics were washed with sat. $NaHCO_3$, $H_2O$ and brine, dried ($MgSO_4$) and evaporated to give a crude orange solid. This was purified by $SiO_2$ chromatography (92.5:7.5, DCM/MeOH, 1% $Et_3N$) to give compound 19 as a bright orange solid (1.61 g, 76%): $^1$H NMR (400 MHz, $CDCl_3$) δ 2.43 (s, 3H), 2.95-3.10 (m, 4H), 3.15-3.27 (m, 4H), 3.31 (s, 3H), 3.53 (t, J=5.1 Hz, 2H), 3.78 (t, J=5.1 Hz, 2H), 6.81-6.91 (m, 2H), 7.05 (s, 1H), 7.37-7.48 (m, 2H), 7.48-7.56 (m, 2H), 8.06-8.17 (m, 2H); $^{13}$C NMR (101 MHz, $CDCl_3$) δ 16.0, 41.0, 45.8, 49.2, 59.0, 70.5, 88.3, 92.7, 113.0, 115.0, 125.4, 126.1, 131.5, 131.9, 132.8, 133.5, 138.7, 151.4, 163.5, 170.6; IR (ATR) $v_{max}$/cm$^{-1}$ 2943 w, 2929 w, 2206 m, 1700 s, 1639 s, 1592 s, 1561 m, 1538 m, 1519 m, 1403 m, 1357 m, 1262 s, 1136 m, 835 m; MS(ES): m/z=429.2 $[M+H]^+$; HRMS (ES) calcd. for $C_{26}H_{29}N_4O_2$ $[M+H]^+$: 429.2291, found 429.2279.

1.3.8 Synthesis of (4Z)-1-[2-(morpholin-4-yl)ethyl]-2-phenyl-4-[(4-{2-[4-(piperazin-1-yl) phenyl] ethynyl}phenyl)methylidene]-4,5-dihydro-1H-imidazol-5-one, 23

The synthesis of (4Z)-1-[2-(morpholin-4-yl)ethyl]-2-phenyl-4-[(4-{2-[4-(piperazin-1-yl) phenyl]ethynyl}phenyl) methylidene]-4,5-dihydro-1H-imidazol-5-one, 23 is shown in FIG. 2(*vii*). $Et_3N$ (90 mL) was degassed by sparging with Ar for 1 h. Compound 4 (2.00 g, 6.94 mmol), compound 22 (3.21 g, 8.33 mmol), $Pd(PPh_3)_2Cl_2$ (250 mg, 0.35 mmol) and CuI (67 mg, 0.35 mmol) were then added under Ar and the resultant suspension was stirred at 60° C. for 40 h. The suspension was diluted with DCM, and the organics were washed with sat. $NaHCO_3$, $H_2O$ and brine, dried ($MgSO_4$) and evaporated to give a crude orange solid. This was purified by $SiO_2$ chromatography (95:5, DCM/MeOH, 1% $Et_3N$) to give compound 23 as a bright red solid (2.80 g, 74%): $^1$H NMR (400 MHz, $CDCl_3$) δ $^1$H NMR (400 MHz, $CDCl_3$) δ 2.23-2.32 (m, 4H), 2.45 (t, J=6.3 Hz, 2H), 3.02 (s, 4H), 3.21 (s, 4H), 3.44-3.58 (m, 4H), 3.91 (t, J=6.3 Hz, 2H), 6.80-6.91 (m, 2H), 7.20 (s, 1H), 7.40-7.47 (m, 2H), 7.48-7.65 (m, 5H), 7.75-7.89 (m, 2H), 8.13-8.23 (m, 2H); $^{13}$C NMR (101 MHz, $CDCl_3$) δ 39.0, 53.6, 56.6, 66.8, 88.3, 93.1, 112.7, 114.9, 125.8, 127.8, 128.4, 128.8, 130.0, 131.2, 131.5, 132.3, 132.8, 133.5, 139.0, 151.5, 162.9, 171.6; MS(ES): m/z=546.3 $[M+H]^+$; HRMS (ES) calcd. for $C_{34}H_{36}N_5O_2$ $[M+H]^+$: 546.2869, found 546.2824.

1.3.9 Synthesis of tert-butyl (2E)-3-(5-{2-[4-(piperazin-1-yl)phenyl]ethynyl}thiophen-2-yl) prop-2-enoate, 27

The synthesis of tert-butyl (2E)-3-(5-{2-[4-(piperazin-1-yl)phenyl]ethynyl}thiophen-2-yl) prop-2-enoate, 27 is shown in FIG. 2(*viii*). $Et_3N$ (75 mL) was degassed by sparging with Ar for 1 h. Compound 4 (2.31 g, 8.00 mmol), compound 26 (2.11 g, 9.01 mmol), $Pd(PPh_3)_2Cl_2$ (280 mg, 0.4 mmol) and CuI (76 mg, 0.4 mmol) were then added under Ar and the resultant suspension 30 was stirred at 65° C. for 72 h. The suspension was diluted with DCM and washed with $H_2O$ and brine, dried ($MgSO_4$) and evaporated to give a crude orange solid. This was purified by $SiO_2$ chromatography (92:8, DCM:MeOH) to give compound 27 as a bright yellow/orange solid (1.4 g, 44%): $^1$H NMR (400 MHz, $CDCl_3$) δ 1.52 (s, 9H), 3.35-3.43 (m, 4H), 3.53-3.61 (m, 4H), 6.13 (d, J=15.7 Hz, 1H), 6.87 (d, J=8.9 Hz, 2H), 7.10 (d, J=3.9 Hz, 1H), 7.13 (d, J=3.9 Hz, 1H), 7.44 (d, J=8.8 Hz, 2H), 7.59 (d, J=15.7 Hz, 1H); $^{13}$C NMR (151 MHz, $CDCl_3$) δ 28.2, 44.9, 47.9, 80.6, 81.4, 96.0, 113.1, 115.4, 119.3, 126.2, 130.6, 132.0, 132.7, 135.5, 140.3, 150.8, 165.9; IR (ATR) $v_{max}$/cm$^{-1}$ 2977 w, 2929 w, 2820 w, 2194 w, 1698 s, 1617 m, 1602 m, 1526 w, 1323 m, 1141 s, 812 w; MS(ES): m/z=395.3 $[M+H]^+$; HRMS (ES) calcd. for $C_{23}H_{27}N_2O_2S$ $[M+H]^+$: 395.1793, found 395.1792.

1.3.10 Synthesis of methyl (2E)-3-(4-{2-[4-(azetidin-1-yl)phenyl]ethynyl}phenyl)prop-2-enoate, 30

The synthesis of methyl (2E)-3-(4-{2-[4-(azetidin-1-yl) phenyl]ethynyl}phenyl)prop-2-enoate (30) is shown in FIG. 2(*ix*). Compound 29 (0.182 g, 1.16 mmol) was dissolved in $Et_3N$ (30 mL) and the solution was degassed by sparging with Ar for 1 h. Methyl (2E)-3-(4-iodophenyl)prop-2-enoate (0.288 g, 1.0 mmol), $Pd(PPh_3)_2Cl_2$ (35 mg, 0.05 mmol) and CuI (10 mg, 0.05 mmol) were then added under Ar and the resultant suspension was stirred at 60° C. for 16 h. The suspension was diluted with diethyl ether ($Et_2O$), passed through Celite/$SiO_2$ and evaporated to give a crude yellow solid. This was purified by $SiO_2$ chromatography (8:2, PE/EtOAc), and further recrystallised from acetonitrile (MeCN) to give compound 30 as a bright yellow crystalline solid (0.204 g, 64%): $^1$H NMR (400 MHz, $CDCl_3$) δ 2.38 (pent, J=7.2 Hz, 2H), 3.81 (s, 3H), 3.90-3.97 (m, 4H), 6.35-6.40 (m, 2H), 6.43 (d, J=16.0 Hz, 1H), 7.36-7.40 (m, 2H), 7.44-7.51 (m, 4H), 7.66 (d, J=7.2 Hz, 1H); $^{13}$C NMR (101 MHz, $CDCl_3$) δ 16.7, 51.7, 52.0, 87.2, 93.2, 110.4, 110.7, 117.8, 126.2, 127.9, 131.6, 132.7, 133.2, 144.1, 151.6, 167.3; IR (ATR) $v_{max}$/cm$^{-1}$ 2963 w, 2922 w, 2855 w, 2207 m, 1713 s, 1632 m, 1595 m, 1522 m, 1366 m, 1325 m, 1314 m, 1173 s, 820 s, 731 s; MS(ES): m/z=318.1 $[M+H]^+$; HRMS (ES) calcd. for $C_{21}H_{20}NO_2[M+H]^+$: 318.1494, found 318.1494.

1.3.11 Synthesis of (4Z)-1-(2-aminoethyl)-4-[(4-{2-[4-(azetidin-1-yl)phenyl]ethynyl}phenyl) methylidene]-2-phenyl-4,5-dihydro-1H-imidazol-5-one, 34

The synthesis of (4Z)-1-(2-aminoethyl)-4-[(4-{2-[4-(azetidin-1-yl)phenyl]ethynyl}phenyl) methylidene]-2-phenyl- 4,5-dihydro-1H-imidazol-5-one (34) is illustrated in FIG. 2(*x*). $Et_3N$ (50 mL) was degassed by sparging with Ar for 1 h. Compound 33 (0.52 g, 1.4 mmol), compound 29 (0.25 g, 1.59 mmol), $Pd(PPh_3)_2Cl_2$(56 mg, 0.08 mmol) and CuI (15 mg, 0.08 mmol) were then added under Ar and the resultant suspension was stirred at 60° C. for 20 h. The solution was evaporated to give a crude residue which was purified by $SiO_2$ chromatography (97:3, DCM/MeOH, 1% $Et_3N$) to give compound 34 as a red solid (0.52 g, 83%): $^1H$ NMR (400 MHz, DMSO-$d_6$) δ 2.33 (p, J=7.3 Hz, 2H), 2.66 (t, J=6.7 Hz, 2H), 3.73 (t, J=6.7 Hz, 2H), 3.87 (t, J=7.3 Hz, 4H), 6.36-6.44 (m, 2H), 7.17 (s, 1H), 7.34-7.38 (m, 2H), 7.51-7.57 (m, 2H), 7.58-7.66 (m, 3H), 7.89-7.94 (m, 2H), 8.24-8.33 (m, 2H).

1.3.12 Synthesis of methyl (2E)-3-(5-{2-[4-(piperazin-1-yl)phenyl]ethynyl}pyridin-2-yl)prop-2-enoate, 43

The synthesis of Methyl (2E)-3-(5-{2-[4-(piperazin-1-yl) phenyl]ethynyl}pyridin-2-yl)prop-2-enoate (43) is shown in FIG. 2(*xi*). $Et_3N$ (125 mL) was degassed by sparging with Ar for 1 h. Compound 4 (2.88 g, 10.0 mmol), compound 42 (2.05 g, 11.0 mmol), $Pd(PPh_3)_2Cl_2$ (350 mg, 0.5 mmol) and CuI (95 mg, 0.5 mmol) were then added under Ar and the resultant suspension was stirred at 60° C. for 72 h. The solvent was then evaporated to give a crude solid which was purified by $SiO_2$ chromatography (95:5 to 9:1, DCM/MeOH, 1% $Et_3N$) to give compound 43 as a bright yellow solid (3.12 g, 90%): $^1H$ NMR (400 MHz, DMSO-$d_6$) δ 3.08-3.40 (m, 4H), 6.91 (d, J=15.7 Hz, 3H), 7.41 (d, J=8.3 Hz, 2H), 7.69 (d, J=15.7 Hz, 1H), 7.78 (dd, J=8.2, 0.8 Hz, 1H), 7.96 (dd, J=8.1, 2.2 Hz, 1H), 8.73 (d, J=2.1 Hz, 1H); $^{13}C$ NMR (101 MHz, DMSO) δ 51.8, 84.8, 95.7, 109.8, 114.3, 121.0, 121.5, 124.4, 132.7, 138.8, 143.0, 150.5, 151.6, 166.3; IR (ATR) $v_{max}/cm^{-1}$ 2950 m, 2835 w, 2209 m, 1711 s, 1639 m, 1605 s, 1577 m, 1516 s, 1319 s, 821 s; MS (ES) m/z=348.2 $[M+H]^+$; HRMS (ES) calcd. for $C_{21}H_{22}N_3O_2$ $[M+H]^+$: 348.1707, found 348.1707.

1.3.13 Synthesis of methylpropyl (2E)-3-(5-{2-[4-(piperazin-1-yl)phenyl]ethynyl}pyridin-2-yl)prop-2-enoate, 46

The synthesis of methylpropyl (2E)-3-(5-{2-[4-(piperazin-1-yl)phenyl]ethynyl}pyridin-2-yl)prop-2-enoate (46) is shown in FIG. 2(*xii*). $Et_3N$ (60 mL) was degassed by sparging with Ar for 1 h. Compound 4 (0.74 g, 2.58 mmol), compound 45 (0.65 g, 2.83 mmol), $Pd(PPh_3)_2Cl_2$ (91 mg, 0.13 mmol) and CuI (25 mg, 0.13 mmol) were then added under Ar and the resultant suspension was stirred at 60° C. for 72 h. The solvent was then evaporated to give a crude solid which was purified by $SiO_2$ chromatography (95:5 to 9:1, DCM/MeOH, 1% $Et_3N$) to give compound 46 as a bright yellow solid (0.62 g, 62%): $^1H$ NMR (400 MHz, $CDCl_3$) δ 0.98 (d, J=6.7 Hz, 6H), 2.01 (hept, J=6.7 Hz, 1H), 2.93-3.07 (m, 4H), 3.17-3.28 (m, 4H), 4.01 (d, J=6.7 Hz, 2H), 6.88 (d, J=8.9 Hz, 2H), 6.93 (d, J=15.7 Hz, 1H), 7.39 (dd, J=8.1, 0.9 Hz, 1H), 7.45 (d, J=8.9 Hz, 2H), 7.67 (d, J=15.7 Hz, 1H), 7.77 (dd, J=8.0, 2.1 Hz, 1H), 8.73 (dd, J=2.1, 0.8 Hz, 1H); IR (ATR) $v_{max}/cm^{-1}$ 2959 m, 2874 w, 2834 w, 2209 m, 1709 s, 1640 m, 1605 s, 1515 s, 1203 s, 1146 s, 821 s; MS (ES) m/z=390.2 $[M+H]^+$; HRMS (ES) calcd. for $C_{24}H_{28}N_3O_2$ $[M+H]^+$: 390.2177, found 390.2176.

1.3.14 Synthesis of methyl (2E)-3-{5-[2-(4-{4-[7-(hydroxycarbamoyl)heptanoyl]piperazin-1-yl}phenyl)ethynyl]pyridin-2-yl}prop-2-enoate, 51

The synthesis of methyl (2E)-3-{5-[2-(4-{4-[7-(hydroxycarbamoyl)heptanoyl]piperazin-1-yl}phenyl)ethynyl]pyridin-2-yl}prop-2-enoate (51) is shown in FIG. 2(*xiii*). Compound 50 (0.78 g, 1.29 mmol) was dissolved in DCM/MeOH (1:2, 60 mL) and cooled to 0° C., whereupon pTSA·$H_2O$ (0.32 g, 1.68 mmol) was added. The resultant solution was stirred at 0° C. for 2 h, and for a further 3.5 h at RT before being diluted with DCM, washed with sat.

$NaHCO_3$ and $H_2O$, dried ($MgSO_4$) and evaporated to give a crude yellow solid (0.7 g). This was purified by $SiO_2$ chromatography (95:5 to 9:1 DCM/MeOH) to give compound 51 as a bright yellow solid (280 mg, 42%): $^1H$ NMR (700 MHz, DMSO-$d_6$) δ 1.23-1.28 (m, 4H), 1.44-1.49 (m, 4H), 1.92 (t, J=7.4 Hz, 2H), 2.32 (t, J=7.4 Hz, 2H), 3.23 (t, J=5.4 Hz, 2H), 3.26-3.29 (m, 2H), 3.58 (t, J=5.4 Hz, 4H), 3.74 (s, 3H), 6.90 (d, J=15.7 Hz, 1H), 6.96-7.00 (m, 2H), 7.42-7.45 (m, 2H), 7.68 (d, J=15.7 Hz, 1H), 7.75-7.83 (m, 1H), 7.96 (dd, J=8.1, 2.2 Hz, 1H), 8.63 (s, 1H), 8.73 (d, J=2.1 Hz, 1H), 10.31 (s, 1H); $^{13}C$ NMR (176 MHz, DMSO-$d_6$) δ 24.6, 25.0, 28.4, 28.5, 32.2, 32.2, 40.5, 44.4, 46.9, 47.2, 51.7, 84.9, 95.4, 110.4, 114.7, 120.9, 121.5, 124.4, 132.7, 138.8, 142.9, 150.5, 150.8, 151.6, 166.3, 169.1, 170.7; IR (ATR) $v_{max}/cm^{-1}$ 3241 br, 2933 w, 2910 w, 2846 w, 2212 w, 1723 m, 1650 s, 1601 s, 1514 m, 1231 m, 1207 m, 1033 m, 830 m; MS(ES): m/z=519.3 $[M+H]^+$; HRMS (ES) calcd. for $C_{29}H_{35}N_4O_5$ $[M+H]^+$: 519.2603, found 519.2602.

1.3.15 Synthesis of 2-methylpropyl (2E)-3-{5-[2-(4-{4-[7-(hydroxycarbamoyl)heptanoyl]piperazin-1-yl}phenyl)ethynyl]pyridin-2-yl}prop-2-enoate, 55

The synthesis of 2-methylpropyl (2E)-3-{5-[2-(4-{4-[7-(hydroxycarbamoyl)heptanoyl]piperazin-1-yl}phenyl)ethynyl]pyridin-2-yl}prop-2-enoate (55) is shown in FIG. 2(*xiv*). Compound 54 (0.55 g, 0.85 mmol) was dissolved in DCM/MeOH (1:2, 60 mL) and cooled to 0° C., whereupon pTSA·$H_2O$ (0.21 g, 1.11 mmol) was added. The resultant solution was stirred at 0° C. for 2 h, and for a further 3.5 h at RT before being diluted with DCM, washed with sat. $NaHCO_3$ and $H_2O$, dried ($MgSO_4$) and evaporated to give a crude yellow solid (0.7 g). This was purified by $SiO_2$ chromatography (9:1, DCM/MeOH) to give compound 55 as a bright yellow solid (340 mg, 71%): $^1H$ NMR (700 MHz, DMSO-$d_6$) δ 0.94 (d, J=6.7 Hz, 6H), 1.23-1.30 (m, 4H), 1.46-1.51 (m, 4H), 1.90-2.01 (m, 3H), 2.33 (t, J=7.5 Hz, 2H), 3.23 (t, J=5.5 Hz, 2H), 3.29 (t, J=5.5 Hz, 2H), 3.59 (t, J=5.3 Hz, 4H), 3.97 (d, J=6.6 Hz, 2H), 6.92 (d, J=15.8 Hz, 1H), 6.96-7.01 (m, 2H), 7.40-7.48 (m, 2H), 7.68 (d, J=15.8 Hz, 1H), 7.80 (d, J=8.1 Hz, 1H), 7.96 (dd, J=8.1, 2.2 Hz, 1H), 8.64 (d, J=1.5 Hz, 1H), 8.74 (d, J=2.2 Hz, 1H), 10.32 (s, 1H); $^{13}C$ NMR (176 MHz, DMSO-$d_6$) δ 18.9, 24.6, 25.0, 27.3, 28.4, 28.5, 32.2, 32.2, 40.5, 44.4, 46.9, 47.2, 70.1, 84.9, 95.4, 110.4, 114.7, 120.8, 121.9, 124.3, 132.6, 132.8, 138.7, 138.9, 142.7, 142.8, 150.6, 150.8, 151.6, 151.6, 165.8, 169.1, 170.7; IR (ATR) $v_{max}/cm^{-1}$ 3245 br, 2933 m, 2846 m, 2212 w, 1710 m, 1649 s, 1601 s, 1544 m, 1369 m, 1231 s, 1031 m, 971 m; MS(ES): m/z=561.3 $[M+H]^+$; HRMS (ES) calcd. for $C_{32}H_{41}N_4O_5$ $[M+H]^+$: 561.3071, found 561.3071.

1.3.16 Synthesis of tert-butyl (2E)-3-{4-[2-(4-{4-[7-(hydroxycarbamoyl)heptanoyl]piperazin-1-yl}phenyl)ethynyl]phenyl}prop-2-enoate, 57

The synthesis of tert-butyl (2E)-3-{4-[2-(4-{4-[7-(hydroxycarbamoyl)heptanoyl]piperazin-1-yl}phenyl)ethynyl] phenyl}prop-2-enoate (57) is shown in FIG. 2(*xv*). Compound 56 (0.14 g, 0.22 mmol) was dissolved in DCM/MeOH (1:4, 12.5 mL) and cooled to 0° C., whereupon pTSA·$H_2O$ (12.7 mg, 0.067 mmol) was added, and the resultant solution was stirred for 2 h at 0° C., and for 2 h at RT. The solution was evaporated to give a crude solid was purified by $SiO_2$ chromatography (95:5 to 9:1, DCM/MeOH) to give compound 57 as a yellow solid (67.5 mg, 55%): $^1H$ NMR (600 MHz, DMSO-$d_6$) δ 1.23-1.30 (m, 4H), 1.46-1.50 (m, 12H), 1.93 (t, J=7.4 Hz, 2H), 2.33 (t, J=7.4 Hz, 2H), 3.19-3.24 (m, 2H), 3.24-3.29 (m, 2H), 3.58 (t, J=4.9 Hz, 4H), 6.56 (d, J=16.0 Hz, 1H), 6.98 (d, J=8.7 Hz, 2H), 7.41 (d, J=8.7 Hz, 2H), 7.51 (d, J=8.2 Hz, 2H), 7.56 (d, J=16.0 Hz, 1H), 7.72 (d, J=8.2 Hz, 2H), 8.66 (s, 1H), 10.33 (s, 1H); $^{13}C$ NMR (176 MHz, DMSO-$d_6$) δ 24.6, 25.0, 27.8, 28.4, 28.5, 32.2, 32.2, 40.6, 44.4, 47.0, 47.4, 80.0, 87.6, 92.4, 111.1, 114.8, 120.5, 124.6, 128.5, 131.4, 132.5, 133.7, 142.6, 150.6, 165.4, 169.1, 170.7; IR (ATR) $v_{max}/cm^{-1}$ 3231 br, 2929 w, 2854 w, 2206 w, 1704 m, 1653 s, 1632 m, 1598 s, 1540 m, 1324 m, 1234 s, 1154 s, 1054 m, 968 m, 826 s; MS(ES): m/z=560.3 $[M+H]^+$; HRMS (ES) calcd. for $C_{33}H_{42}N_3O_5$ $[M+H]^+$: 560.3119, found 560.3119.

1.3.17 Synthesis of tert-butyl (2E)-3-{5-[2-(4-{4-[7-(hydroxycarbamoyl)heptanoyl]piperazin-1-yl}phenyl)ethynyl]thiophen-2-yl}prop-2-enoate, 59

The synthesis of tert-butyl (2E)-3-{5-[2-(4-{4-[7-(hydroxycarbamoyl)heptanoyl]piperazin-1-yl}phenyl)ethynyl] thiophen-2-yl}prop-2-enoate (59) is shown in FIG. 2(*xvi*). Compound 58 (0.3 g, 0.46 mmol) was dissolved in DCM/MeOH (1:4, 12.5 mL) and cooled to 0° C., whereupon pTSA·$H_2O$ (27 mg, 0.14 mmol) was added. The resultant solution was stirred at 0° C. for 2 h, and for a further 2 h at RT before being evaporated to give a crude yellow oil. This was purified by $SiO_2$ chromatography (DCM/MeOH, 95:5 to 9:1) to give compound 59 as a bright yellow solid (49 mg, 19%): $^1H$ NMR (400 MHz, DMSO-$d_6$) δ 1.21-1.30 (m, 4H), 1.43-1.56 (m, 13H), 1.93 (t, J=7.3 Hz, 2H), 2.33 (t, J=7.5 Hz, 2H), 3.18-3.26 (m, 2H), 3.26-3.31 (m, 2H), 3.54-3.64 (m, 4H), 6.18 (d, J=15.7 Hz, 1H), 6.97 (d, J=9.0 Hz, 2H), 7.32 (d, J=3.8 Hz, 1H), 7.41 (d, J=8.9 Hz, 2H), 7.49 (d, J=3.8 Hz, 1H), 7.66 (dd, J=15.7, 0.6 Hz, 1H), 8.65 (s, 1H), 10.32 (s, 1H); $^{13}C$ NMR (176 MHz, DMSO) δ 24.6, 25.0, 27.8, 28.4, 28.5, 32.2, 32.2, 40.5, 44.4, 46.8, 47.2, 80.2, 80.9, 96.6, 110.2, 114.7, 118.9, 125.3, 132.2, 132.5, 132.7, 135.6, 139.6, 150.8, 165.1, 169.1, 170.7; IR (ATR) $v_{max}/cm^{-1}$ 3235 br, 2978 w, 2928 w, 2855 w, 2832 w, 2188 w, 1704 m, 1654 s, 1603 s, 1525 m, 1249 s, 1145 s; MS (ES) m/z=566.2 $[M+H]^+$; HRMS (ES) calcd. for $C_{31}H_{30}N_3O_5S$ $[M+H]^+$: 566.2689, found 566.

1.3.18 Synthesis of 2-(2-methoxyethoxy)ethyl-(2E)-3-(4-{2-[4-(piperazin-1yl) phenyl]ethynyl}phenyl) prop-2-enoate, 62

The synthesis of 2-(2-methoxyethoxy)ethyl-(2E)-3-(4-{2-[4-(piperazin-1yl)phenyl]ethynyl}phenyl) prop-2-enoate (62) is shown in FIG. 2(*xvii*). Compound 4 (788 mg, 2.73 mmol), compound 61 (788.3 mg, 2.87 mmol), $Pd(PPh_3)_2Cl_2$ (91.24 mg, 0.13 mmol) and CuI (24.75 mg, 0.13 mmol) were added into a Schlenk flask under Ar. Degassed $Et_3N$ (10 mL) was then added and the resultant suspension was stirred at 60° C. for 24 h. The solvent was then evaporated to give a crude orange solid, which was purified by $SiO_2$ chromatography (9:1, DCM/MeOH) to yield compound 62 as an orange solid (794 mg, 67%). $^1H$ NMR ($CDCl_3$, 400 MHz) δ 3.16-3.24 (m, 2H), 3.4 (s, 3H), 3.46-3.51 (m, 4H), 3.56-3.59 (m, 2H), 3.63-3.70 (m, 6H), 3.77-3.80 (m, 2H), 4.36-4.40 (m, 2H), 6.48 (d, J=16 Hz, 1H), 6.88 (dt, J 8.9, 2 Hz, 2H), 7.46-7.52 (m, 6H), 7.68 (d, J=16 Hz, 1H); $^{13}C$ NMR (101 MHz, $CDCl_3$) δ 166.95, 144.31, 133.17, 132.01, 128.18, 116.68, 72.06, 70.69, 69.45, 63.87, 59.27, 46.51, 46.00, 43.47, 8.80; HRMS (ESI) calcd. for $C_{26}H_{31}N_2O_4$ $[M+H]^+$ 435.2284, found 435.2283.

1.3.19 Synthesis of 2-(2-methoxyethoxy)ethyl(2E)-3-{4-[2-(4-{4-[8-(hydroxyamino) octanoyl]piperazin-1-yl}phenyl) ethynyl]phenyl}prop-2-enoate, 64

The synthesis of 2-(2-methoxyethoxy)ethyl (2E)-3-{4-[2-(4-{4-[8-(hydroxyamino) octanoyl]piperazin-1-yl}phenyl) ethynyl]phenyl}prop-2-enoate (64) is shown in FIG. 2(*xviii*). Compound 63 (384 mg, 0.55 mmol) was dissolved in DCM:MeOH (1:2) and the resulting solution was cooled down to 0° C., followed by the addition of para-toluenesulfonic acid monohydrate (pTsOH·$H_2O$) (56.3 mg, 0.28 mmol). The reaction mixture was then stirred at RT for 5 h. Additional pTsOH·$H_2O$ (56.3 mg, 0.28 mmol) was added and the reaction mixture was continued to stir at RT for further 16 h. The reaction crude was then diluted in DCM, washed with $NaHCO_3$ (sat.) and brine, dried over $MgSO_4$ and evaporated to give an orange solid crude. The crude was purified by $SiO_2$ column chromatography (DCM:MeOH, 9:1 as eluent) to give compound 64 as an orange solid (60.3 mg, 18%): $^1H$ NMR (DMSO-$d_6$, 400 MHz) δ 1.22-1.32 (m, 6H), 1.44-1.52 (m, 6H), 1.93 (t J 14.7 Hz, 7.3 Hz, 2H), 2.33 (t J 14.7 Hz, 7.3 Hz, 3H), 3.19-3.23 (m, 4H), 3.24 (s, 3H), 3.43-3.46 (m, 3H), 3.54-3.60 (m, 8H), 3.65-3.69 (m, 2H), 4.23-4.29 (m, 3H), 6.72 (d J 16 Hz, 1H), 6.97 (d J 8.9 Hz, 2H), 7.42 (d J 8.9 Hz, 2H), 7.52 (d J 8.4 Hz, 2H), 7.67 (d J 16 Hz, 1H), 7.7 (d J 8.4 Hz, 1H), 8.64-8.67 (m, 1H), 10.33 (s, 1H); $^{13}C$ NMR (101 MHz, DMSO-$d_6$) δ 132.39, 128.49, 114.60, 71.04, 69.39, 57.88, 39.94, 39.73, 39.52, 39.31, 39.10, 38.89, 38.69, 32.03, 28.23, 24.83; HRMS (ESI) calcd. for $C_{34}H_{44}N_3O_7$ $[M+H]^+$: 606.3179, found 606.3193.

1.3.20 Synthesis of 2-methylpropyl (2E)-3-(6-{2-[4-(piperazin-1-yl)phenyl]ethynyl}pyridin-3-yl)prop-2-enoate, 69

The synthesis of 2-methylpropyl (2E)-3-(6-{2-[4-(piperazin-1-yl)phenyl]ethynyl}pyridin-3-yl)prop-2-enoate (69) is shown in FIG. 2(*xix*). Compound 4 (1.21 g, 4.2 mmol), compound 68 (1.0 g, 4.4 mmol), $Pd(PPh_3)_2Cl_2$ (147 mg, 0.21 mmol) and CuI (39 mg, 0.21 mmol) were added into a Schlenk round bottom flask under Ar, followed by the addition of $Et_3N$ previously sparged with $N_2$ for 1 h (50 mL). The resulting reaction mixture was stirred at 60° C. for 24 h. After $SiO_2$ column chromatography (DCM:MeOH, 9:1) compound 69 was obtained as a bright yellow solid (1.1 g, 67%). 1H NMR (400 MHz, $CDCl_3$) δ 0.99 (d J 6.7 Hz, 6H), 1.98-2.05 (m, 1H), 3.20-3.26 (m, 4H), 3.40-3.44 (m, 4H), 4.01 (d J 6.7 Hz, 2H), 6.52 (d J 16.0 Hz, 1H), 6.88 (d J 9.0 Hz, 2H), 7.48-7.55 (m, 3H), 7.65 (d J 16.0 Hz, 1H), 7.81 (dd J 8.45, 2.2 Hz, 1H), 8.72 (d J 2.2 Hz, 1H); $^{13}C$ NMR (101 MHz, $CDCl_3$) d 166.51, 151.05, 150.13, 144.99, 140.39, 138.20, 134.32, 133.67, 126.91, 120.65, 119.00, 115.71, 92.36, 88.06, 71.10, 44.61, 27.97, 19.29; HRMS (ESI) calcd. for $C_{24}H_{28}N_3O_2$ $[M+H]^+$: 390.2182, found 390.2181.

1.3.21 Synthesis of 2-methylpropyl(2E)-3-{6-[2-(4-{4-[7-(hydroxycarbamoyl)heptanoyl]piperazin-1-yl}phenyl) ethynyl]pyridin-3-yl}prop-2-enoate, 71

The synthesis of 2-methylpropyl (2E)-3-{6-[2-(4-{4-[7-(hydroxycarbamoyl) heptanoyl]piperazin-1-yl}phenyl) ethynyl]pyridin-3-yl}prop-2-enoate (71) is shown in FIG.

2(*xx*). Compound 70 (500 mg, 0.76 mmol) was dissolved in DCM:MeOH (1:2) and the resulting solution was cooled down to 0° C. pTsOH·$H_2O$ (197.6 mg, 0.988 mmol) was then added and the reaction mixture was then allowed to warm to RT and continued to stir for 6 h. The crude reaction mixture was diluted in DCM, washed with $NaHCO_3$ (sat) and brine, dried over $MgSO_4$ and evaporated to give a crude bright yellow solid (0.3 g). This was then purified by $SiO_2$ column chromatography (DCM:MeOH, 9:1) to yield compound 71 as a bright yellow solid (90.4 mg, 21%): $^1H$ NMR (400 MHz, DMSO-$d_6$) δ 0.95 (d J 6.7 Hz, 6H), 1.22-1.31 (m, 6H), 1.44-1.53 (m, 6H), 1.91-1.95 (m, 2H), 1.96-2.00 (m, 1H), 3.55-3.62 (m, 4H), 3.97 (d J 6.6 Hz, 2H), 6.85 (d J 16.0 Hz, 1H), 7.01 (d J 9.0 Hz, 2H), 7.44-7.52 (m, 3H), 7.72 (d J 16.0 Hz, 1H), 8.23 (dd J 8.4 Hz, 2.3 Hz, 1H), 8.88-8.91 (m, 1H), 10.34 (s, 1H); HRMS (ESI) calcd. for $C_{32}H_{41}N_4O_5$ $[M+H]^+$: 561.3077, found 561.3087.

1.3.22 Synthesis of methyl (2E)-3-(5-{2-[4-(4-methylpiperazin-1-yl)phenyl]ethynyl}pyridin-2-yl) prop-2-enoate, 73

The synthesis of methyl (2E)-3-(5-{2-[4-(4-methylpiperazin-1-yl)phenyl]ethynyl}pyridin-2-yl)prop-2-enoate (73) is shown in FIG. 2(*xxi*). $Et_3N$ (60 mL) was degassed by sparging with Ar for 1 h. Compound 72 (1.11 g, 3.66 mmol), compound 42 (0.75 g, 4.02 mmol), $Pd(PPh_3)_2Cl_2$ (128 mg, 0.18 mmol) and CuI (34 mg, 0.18 mmol) were then added under Ar and the resultant suspension was stirred at 60° C. for 72 h. The solvent was then evaporated to give a crude solid which was purified by $SiO_2$ chromatography (95:5 to 9:1, DCM/MeOH, 1% $Et_3N$), followed by recrystallisation from MeCN to give compound 73 as a bright yellow solid (1.02 g, 77%): $^1H$ NMR (700 MHz, $CDCl_3$) δ 2.35 (s, 3H), 2.56 (t, J=5.0 Hz, 4H), 3.26-3.30 (m, 4H), 3.82 (s, 3H), 6.87 (d, J=8.6 Hz, 2H), 6.92 (d, J=15.6 Hz, 1H), 7.36 (d, J=8.0 Hz, 1H), 7.41-7.46 (m, 2H), 7.66 (d, J=15.6 Hz, 1H), 7.76 (dd, J=8.0, 2.1 Hz, 1H), 8.72 (d, J=2.1 Hz, 1H); $^{13}C$ NMR (176 MHz, $CDCl_3$) δ 46.1, 47.9, 51.8, 54.8, 84.8, 95.4, 111.9, 114.9, 121.6, 122.0, 123.5, 132.9, 138.5, 142.9, 150.8, 151.3, 152.2, 167.2; IR (ATR) $v_{max}/cm^{-1}$ 3066 w, 3036 w, 2878 w, 2797 w, 2212 m, 1714 s, 1640 m, 1603 m, 1543 m, 1515 s, 1305 s, 1241 s, 1190 s, 1161 s, 1006 m; MS (ES) m/z=362.2 $[M+H]^+$; HRMS (ES) calcd. for $C_{22}H_{24}N_3O_2$ $[M+H]^+$: 362.1863, found 362.1863.

1.3.23 Synthesis of 4-[(E)-2-(5-{2-[4-(morpholin-4-yl)phenyl]ethynyl}pyridin-2-yl)ethenyl]-1,3-thiazol-2-amine, 84

The synthesis of 4-[(E)-2-(5-{2-[4-(morpholin-4-yl)phenyl]ethynyl}pyridin-2-yl)ethenyl]-1,3-thiazol-2-amine (84) is shown in FIG. 2(*xxii*). A mixture of $Et_3N$ (30 mL) and DMF (60 mL) was degassed by sparging with Ar for 1 h. Compound 83 (2.3 g, 8.0 mmol), compound 82 (2.0 g, 8.8 mmol), $Pd(PPh_3)_2Cl_2$ (281 mg, 0.4 mmol) and CuI (76 mg, 0.4 mmol) were then added under Ar and the resultant solution was stirred at 60° C. for 72 h. The suspension was cooled, $H_2O$ added, and the mixture was filtered to give a crude brown solid. This was suspended in a mixture of DCM/EtOAc/acetone (1:1:1), stirred for 0.5 h and filtered to give compound 84 as a light yellow solid (3.03 g, >100%): $^1H$ NMR (400 MHz, DMSO-$d_6$) δ 3.18-3.23 (m, 4H), 3.73 (t, J=5.1 Hz, 4H), 6.82 (s, 1H), 6.97 (d, J=8.3 Hz, 3H), 7.06-7.17 (m, 3H), 7.36-7.45 (m, 3H), 7.49 (d, J=7.9 Hz, 1H), 7.83 (d, J=7.9 Hz, 1H), 8.64 (dd, J=0.8 Hz, 1H).

Example 2: Measurement of Absorption and Fluorescence Emission of Exemplified Compounds Peak absorption and fluorescence emission wavelengths of compounds 6, 7, 12, 13, 14, 15, 19, 23, 27, 30 and 34 were measured in a variety of solvents, and the results are shown in Table 1. Absorption measurements were recorded at a concentration of 10 μM, and emission measurements were recorded at a concentration of 100 nM. Emission spectra were recorded with excitation at the peak of absorption ($S_0 \rightarrow S_1$).

TABLE 1

Peak absorption and emission wavelengths of compounds 6, 7, 12, 13, 14, 15, 19, 23, 27, 30 and 34 in a variety of solvents.

| Compound | Solvent | $\lambda_{abs}$(max)/nm | $\lambda_{em}$(max)/nm |
|---|---|---|---|
| 6 | Toluene | 358 | 482 |
| | DCM | 368 | 550 |
| 7 | Toluene | 361 | 504 |
| | DCM | 362 | 563 |
| 12 | Toluene | 380 | 482 |
| | DCM | 371 | 551 |
| 13 | Toluene | 358 | 464 |
| | DCM | 361 | 547 |
| 14 | Toluene | 367 | 506 |
| | DCM | 361 | 531 |
| 15 | Toluene | 381 | 473 |
| | DCM | 377 | 545 |
| 19 | Toluene | 403 | 515 |
| | Chloroform | 403 | 584 |
| | MeOH | 395 | — |
| 23 | Chloroform | 424 | 616 |
| 27 | Toluene | 380 | 493 |
| | DCM | 371 | 524 |
| 30 | Chloroform | 374 | 535 |
| 34 | Chloroform | 432 | 628 |

Example 3: Photophysical Comparison of Para-Substituted and Ortho-Substituted Compounds To compare the photophysical behaviour of para-substituted compounds of the invention with ortho-substituted compounds, compound 73 and reference compound 77 were synthesised in accordance with Example 1:

73

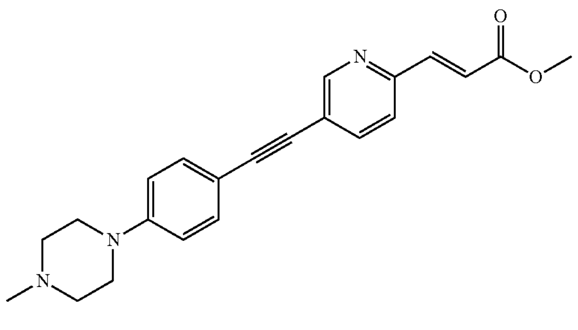

-continued

77

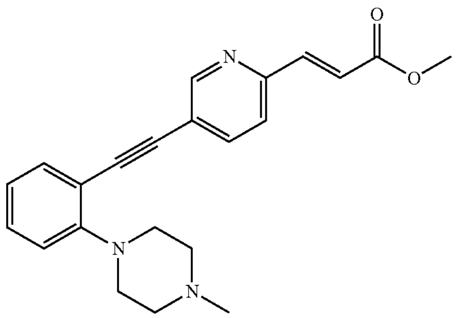

Figure 3A:
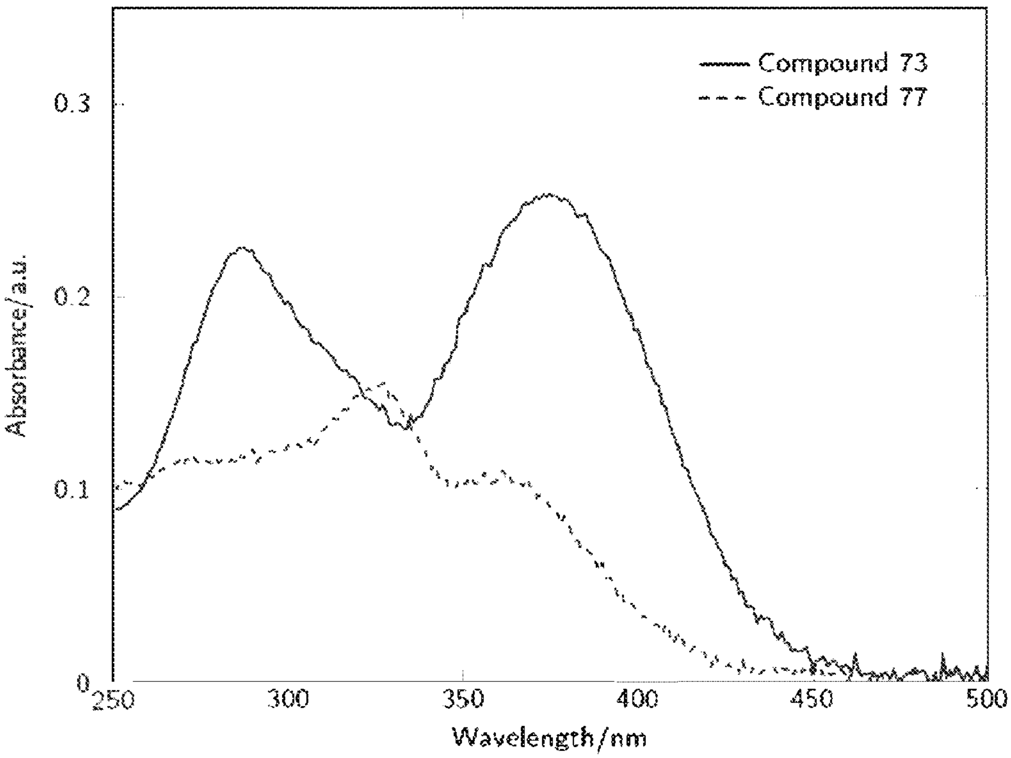

Solutions of compounds 73 and 77 were prepared at concentrations of 10 μM and 100 nM in chloroform. The absorption spectra of each compound (10 μM) was recorded using a CARY100 UV-Visible spectrometer, from 200-800 nm, and is shown in FIG. 3*a* after solvent background subtraction. FIG. 3*a* illustrates the substantial hypsochromic shift and reduction in extinction coefficient as a result of moving the donor moiety from the para-position in 73 to the ortho-position of 77. Also shown in FIG. 3*a* is the approximate bandwidth of a 405 nm violet excitation laser light source that is commonplace on fluorescence microscopes used for cellular imaging studies. Compound 73 is capable of efficient excitation by this light source, but 77 absorbed only very weakly at this wavelength.

Figure 3B:
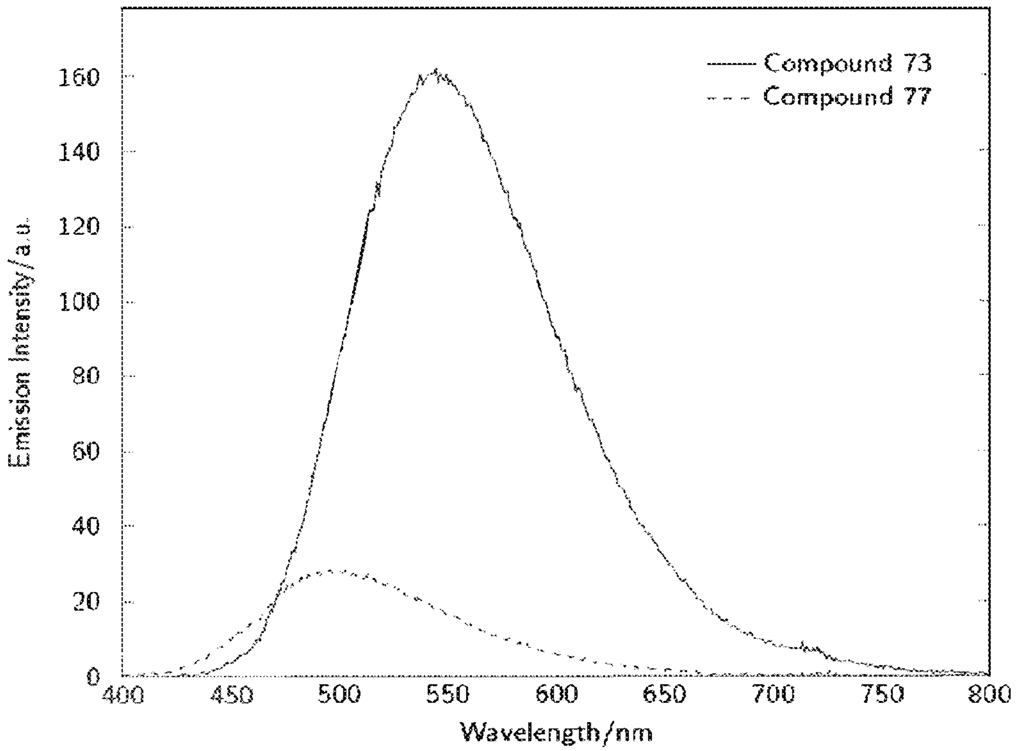

To assess this effect and to compare the fluorescence emission properties of 73 and 77, solutions of both compounds in chloroform (100 nM) were excited at both 360 nm and 405 nm. At 360 nm excitation, 73 and 77 were excited with high efficiency since this wavelength is close to the absorption maxima of both compounds. FIG. 3*b* shows that, although both compounds can be excited at this wavelength, compound 73 exhibited substantially stronger fluorescence emission as a result of improved quantum yield. Compound 73 also exhibited a significant bathochromic shift compared to compound 77 indicating that charge transfer is more efficient in the para-substituted compound which translates to a more significant dipole moment across the molecule and, hence, a larger Stokes shift.

Figure 3C:
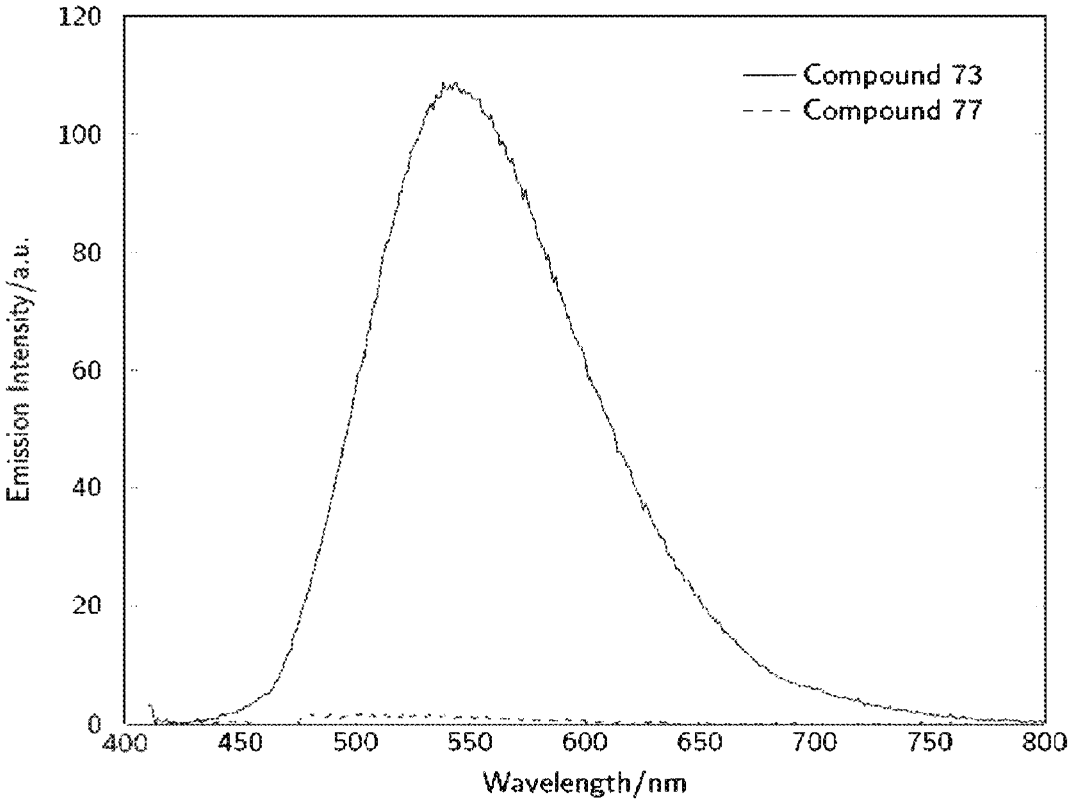

Both compounds were also excited at 405 nm to compare their respective suitabilities towards imaging using a typical fluorescence microscope. FIG. 3*c* shows that, whilst the emission from compound 73 at an excitation of 405 nm was of a similar intensity to excitation at 360 nm, compound 77 displayed only very weak fluorescence emission at 405 nm since this compound does not absorb efficiently at 405 nm. Hence, 77 would not be a suitable fluorophore in a cellular imaging experiment using a 405 nm excitation source.

In conclusion, the para-substituted diphenylacetylene fluorophores exhibit improved photophysical properties over the corresponding ortho-substituted compounds due to stronger, and longer wavelength absorption of light, and more efficient fluorescence emission with augmented charge transfer behaviour.

Example 4: Synthesis of conjugates

4.1 Conjugation to Anti-Cancer Drug Molecule

Compound 6 was conjugated to the approved cancer drug, vorinostat. In order to assess the impact of the conjugation on the activity of vorinostat, three compounds were prepared: A THP-protected analogue of vorinostat (compound 37); a THP-protected analogue of vorinostat conjugated to compound 6 (compound 38); and an unprotected vorinostat analogue conjugated to compound 6 (compound 39).

4.1.1 Synthesis of THP-Protected Analogue of Vorinostat (Compound 37)

Figure 4I:
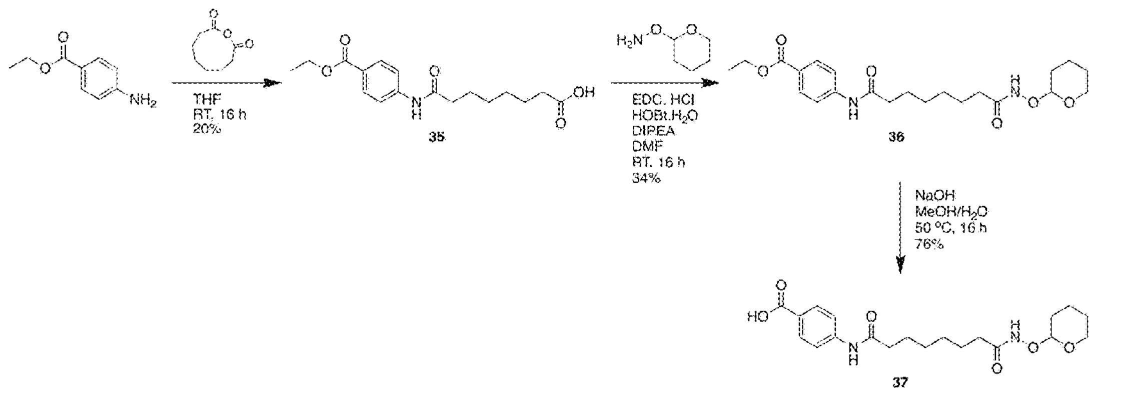
Figure 4:
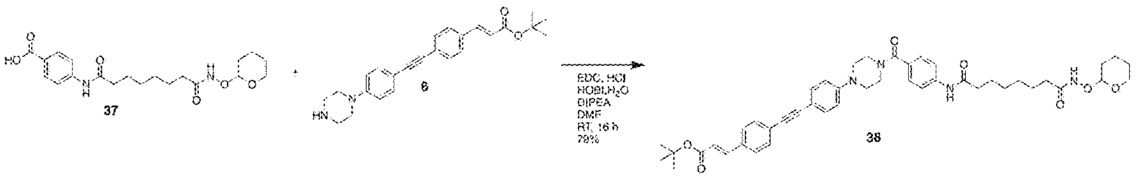

The synthesis of the protected analogue of vorinostat is illustrated in FIG. 4(*a*). Ethyl 4-amino benzoate (16.87 g, 102 mmol) was dissolved in anhydrous THE under $N_2$. Oxanone-2,9-dione (Suberic anhydride) (15.95 g, 102 mmol) was added and the resultant solution was stirred at RT for 16 h. The suspension was diluted with $H_2O$, and the precipitate was filtered and washed with $H_2O$. This was purified by $SiO_2$ chromatography (7:3 to 1:1, heptane/EtOAc) to give compound 35 as a white solid (6.62 g, 20%), which was carried directly to the next step: $^1H$ NMR (400 MHz, DMSO-$d_6$) δ 1.22-1.34 (m, 7H), 1.42-1.53 (m, 2H), 1.53-1.64 (m, 2H), 2.15-2.22 (m, 2H), 2.33 (t, J=7.4 Hz, 2H), 4.27 (q, J=7.1 Hz, 2H), 7.70-7.74 (m, 2H), 7.86-7.91 (m, 2H), 10.20 (s, 1H), 11.94 (br, 1H). Compound 35 (1.8 g, 5.60 mmol) was dissolved in anhydrous DMF (20 mL) under $N_2$, whereupon 1-ethyl-3-(3-dimethylaminopropyl)carbodiimide (EDC)·HCl (1.28 g, 6.70 mmol) and hydroxybenzothiazole (HOBt) (hydrate, 0.91 g, 6.7 mmol) were added and the resultant suspension was stirred for 0.5 h at RT. O-(Tetrahydro-2H-pyran-2-yl)hydroxylamine (0.78 g, 6.70 mmol) and N,N-diisopropylethylamine (DIPEA) (1.46 mL, 8.40 mmol) were then added and the solution was stirred at RT for 16 h. The solution was diluted with $H_2O$ and extracted with DCM. The organics were washed with $H_2O$, dried ($MgSO_4$) and evaporated to give a crude light yellow oil. This was purified by $SiO_2$ chromatography (7:3, heptane/acetone) to give compound 36 as an off-white solid (0.81 g, 34%), which was carried directly to the next step without further purification. Compound 36 (0.62 g, 1.47 mmol) and NaOH (0.13 g, 3.13 mmol) were dissolved in $MeOH/H_2O$ (18 mL, 2:1) and the resultant solution was stirred at 50° C. for 16 h. The solution was cooled, diluted with $H_2O$, acidified to pH 4 and then extracted with EtOAc. The organics were washed with $H_2O$ and brine, dried ($MgSO_4$) and evaporated to give compound 37 as a white solid (0.44 g, 76%): $^1H$ NMR (400 MHz, DMSO-$d_6$) δ 1.20-1.34 (m, 4H), 1.44-1.69 (m, 10H), 1.97 (t, J=7.3 Hz, 2H), 2.33 (t, J=7.4 Hz, 2H), 3.45-3.52 (m, 1H), 3.87-3.94 (m, 1H), 4.79 (br, 1H), 7.67-7.72 (m, 2H), 7.84-7.89 (m, 2H), 10.17 (s, 1H), 10.90 (s, 1H), 12.68 (br, 1H); $^{13}C$ NMR (101 MHz, DMSO-$d_6$) δ 18.3, 24.7, 27.8, 28.3, 28.4, 32.1, 36.4, 61.3, 100.8, 118.2, 124.8, 130.4, 143.4, 166.9, 169.0, 171.8; IR (ATR) $v_{max}/cm^{-1}$ 3301 w, 2972 w, 2944 w, 2855 w, 1662 s, 1593 m, 1523 m, 1405 m, 1295 m, 913 m, 734 s; MS(ES): m/z=393.4 $[M+H]^+$; HRMS (ES) calcd. for $C_{20}H_{29}N_2O_4$ $[M+H]^+$: 393.2026, found 393.2027.

4.1.2 Synthesis of THP-Protected Analogue of Vorinostat Conjugated to Compound 6 (Compound 38)

Compound 37 (0.36 g, 0.9 mmol) was dissolved in anhydrous DMF (10 mL) under $N_2$, whereupon EDC·HCl (0.18 g, 1.17 mmol) and HOBt (hydrate, 0.12 g, 0.9 mmol) were added and the resultant suspension was stirred for 0.5 h at RT. Compound 6 (0.35 g, 0.9 mmol) and DIPEA (0.24 mL, 1.35 mmol) were then added and the solution was stirred at RT for 40 h. The solution was diluted with $H_2O$ and extracted with DCM. The organics were washed with $H_2O$, dried ($MgSO_4$) and evaporated to give a crude yellow oil (0.69 g). This was purified by $SiO_2$ chromatography (97:3, DCM/MeOH) to give compound 38 as a yellow solid (0.54 g, 79%): $^1$H NMR (400 MHz, $CDCl_3$) δ 1.20-1.35 (m, 4H), 1.52 (s, 9H), 1.53-1.70 (m, 7H), 1.72-1.82 (m, 3H), 2.02-2.12 (m, 2H), 2.31 (t, J=7.4 Hz, 2H), 3.25 (br, 4H), 3.57-4.00 (m, 6H), 4.95 (s, 1H), 6.36 (d, J=16.0 Hz, 1H), 6.86 (d, J=8.6 Hz, 2H), 7.38 (d, J=8.4 Hz, 2H), 7.41-7.50 (m, 6H), 7.54 (d, J=16.0 Hz, 1H). 7.66 (d, J=8.0 Hz, 2H), 8.67 (s, 1H), 9.36 (s, 1H); $^{13}$C NMR (101 MHz, $CDCl_3$) δ 18.5, 24.9, 25.0, 25.2, 28.0, 28.1, 28.3, 28.5, 32.9, 37.1, 48.6, 62.4, 80.6, 88.0, 91.8, 102.3, 114.0, 115.7, 119.5, 120.5, 125.2, 127.8, 128.1, 130.0, 131.7, 132.8, 133.9, 140.3, 142.7, 150.3, 166.2, 170.3, 170.7, 172.4; IR (ATR) $v_{max}$/cm$^{-1}$ 3252 br, 2933 w, 2858 w, 2251 w, 2210 w, 1698 m, 1666 m, 1630 m, 1596 s, 1519 s, 1436 m, 1235 m, 1152 s, 1136 s, 731 s; MS(ES): m/z=763.5 [M+H]$^+$; HRMS (ES) calcd. for $C_{45}H_{55}N_4O_7$ [M+H]$^+$: 763.4071, found 763.4086.

4.1.3 Synthesis of the Unprotected Vorinostat Analogue Conjugated to Compound 6 (Compound 39)

Compound 38 (0.36 g, 0.47 mmol) was dissolved in MeOH/DCM (20 mL, 3:1) and cooled to 0° C. p-Toluenesulfonic acid (pTSA)·$H_2O$ (29 mg, 0.15 mmol) was then added and the resultant solution was stirred rapidly at RT for 3 h. A further amount of pTSA·$H_2O$ (14 mg, 0.075 mmol) was then added and the solution was stirred for 1 h. The solution was evaporated to give a crude yellow solid, which was purified by $SiO_2$ chromatography (95:5, DCM/EtOH to 9:1, DCM/MeOH) to give a light yellow solid which was further recrystallised from EtOH to give compound 39 as a pale yellow solid (131 mg, 41%): $^1$H NMR (400 MHz, DMSO-$d_6$) δ 1.21-1.35 (m, 4H), 1.48 (s, 9H), 1.51-1.64 (m, 4H), 1.94 (t, J=7.4 Hz, 2H), 2.31 (t, J=7.4 Hz, 2H), 3.25-3.42 (m, 4H), 3.62 (br, 4H), 6.54 (d, J=16.0 Hz, 1H), 6.98 (d, J=8.8 Hz, 2H), 7.40-7.43 (m, 4H), 7.51 (d, J=8.3 Hz, 2H), 7.55 (d, J=16.0 Hz, 1H), 7.67 (d, J=8.6 Hz, 2H), 7.71 (d, J=8.3 Hz, 2H), 8.66 (s, 1H), 10.06 (s, 1H), 10.33 (s, 1H); $^{13}$C NMR (101 MHz, DMSO-$d_6$) δ 25.0, 25.0, 27.9, 28.4, 32.3, 36.4, 47.3, 80.1, 87.7, 92.5, 111.3, 114.9, 118.4, 120.5, 124.7, 128.2, 128.5, 129.8, 131.4, 132.6, 133.7, 140.7, 142.7, 150.6, 165.5, 169.0, 169.1, 171.6; IR (ATR) $v_{max}$/cm$^{-1}$ 3285 br, 2975 w, 2931 w, 2851 w, 2822 w, 2208 w, 2167 w, 1706 m, 1655 m, 1626 m, 1596 s, 1520 s, 1391 m, 1234 m, 1154 s, 1136 s, 976 m, 825 s, 736 s; MS(ES): m/z=679.6 [M+H]$^+$; HRMS (ES) calcd. for $C_{40}H_{47}N_4O_6$ [M+H]$^+$: 679.3496, found 679.3510.

Example 5: Conjugate Assays

5.1 Cell Viability Assays

Figure 5A:
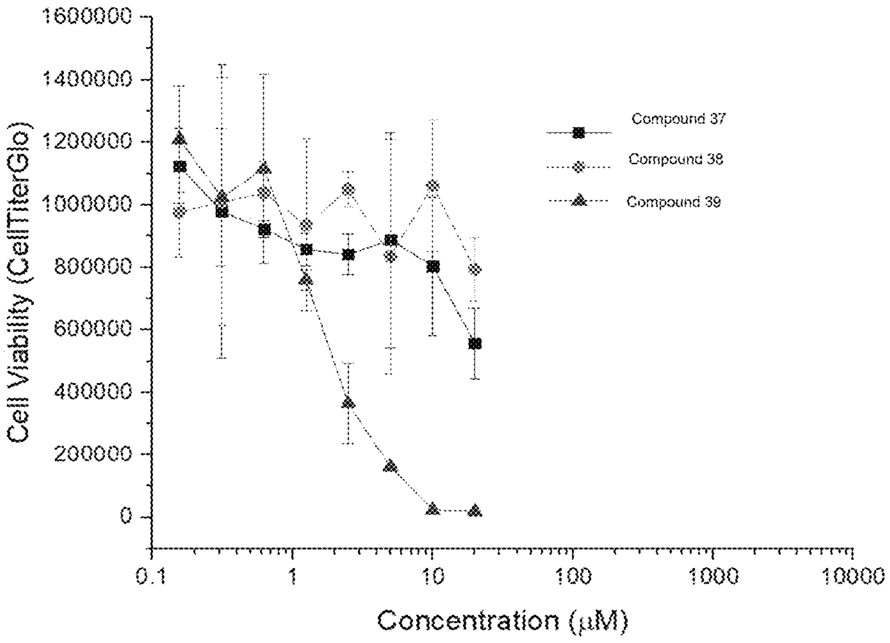
FIG. 5 illustrates cell viability using the CellTitreGlow assay for primary, HPV-negative oral squamous carcinoma cells (a) cell line SJG-26; and (b) cell line SJG-41.
Figure 5B:
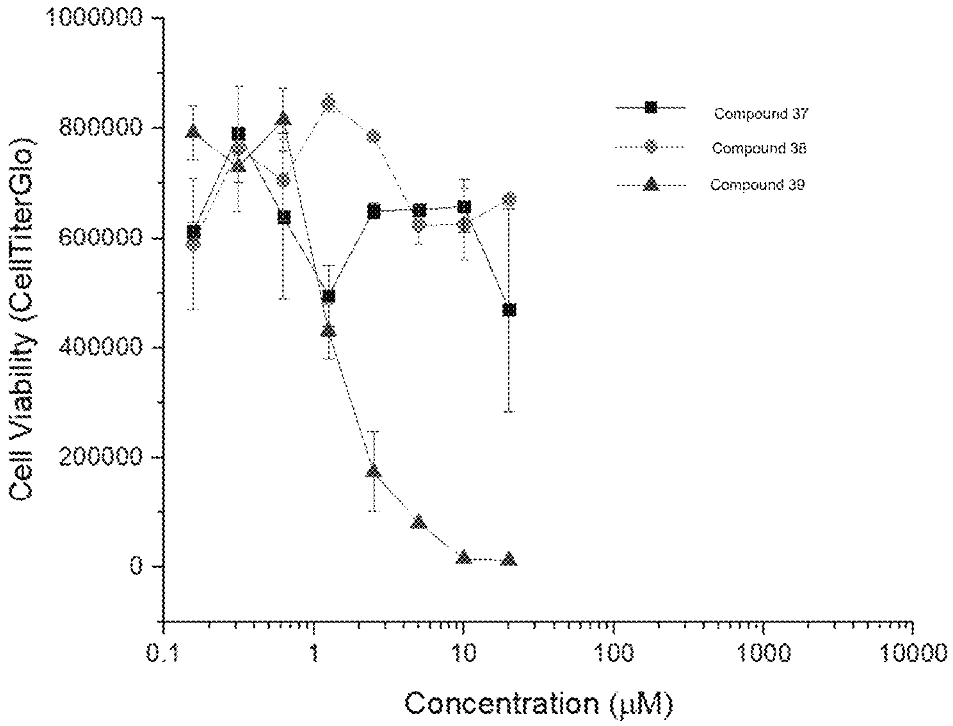

Cell viability was measured using the CellTitreGlo® assay according to the manufacturer's instructions. Two primary, HPV-negative oral squamous carcinoma cells (SJG-26 and SJG-41) were treated for 72 hours with compound 37, compound 38 and compound 39 before performing the assay. Cells were not irradiated. The $IC_{50}$ of vorinostat alone (not shown) was found to be 1.6 μM; the $IC_{50}$ of compound 39 was nearly identical (1.3 μM for SJG-26 and 1.4 μM for SJG-41). The results of the assays are shown in FIG. 5*a* (Cell line SJG-26) and 5b (Cell Line SJG-41).

5.2 MTT Cell Viability Assay

Figure 6A:
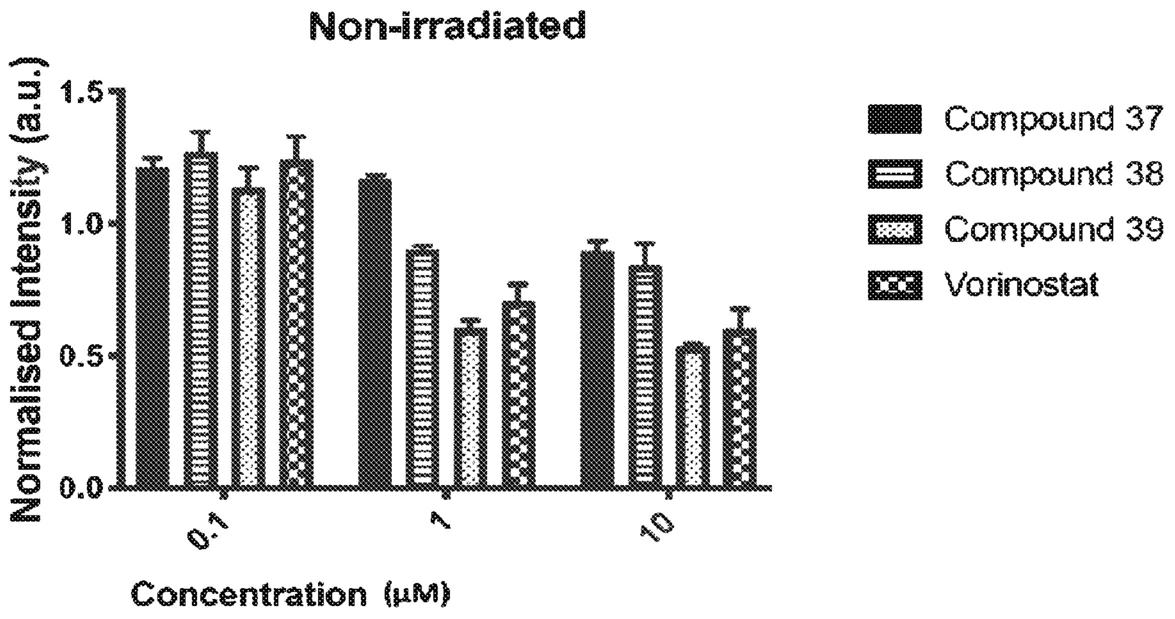
FIG. 6 illustrates MTT viability assay results for (a) non-irradiated, and (b) irradiated assays.
Figure 6B:
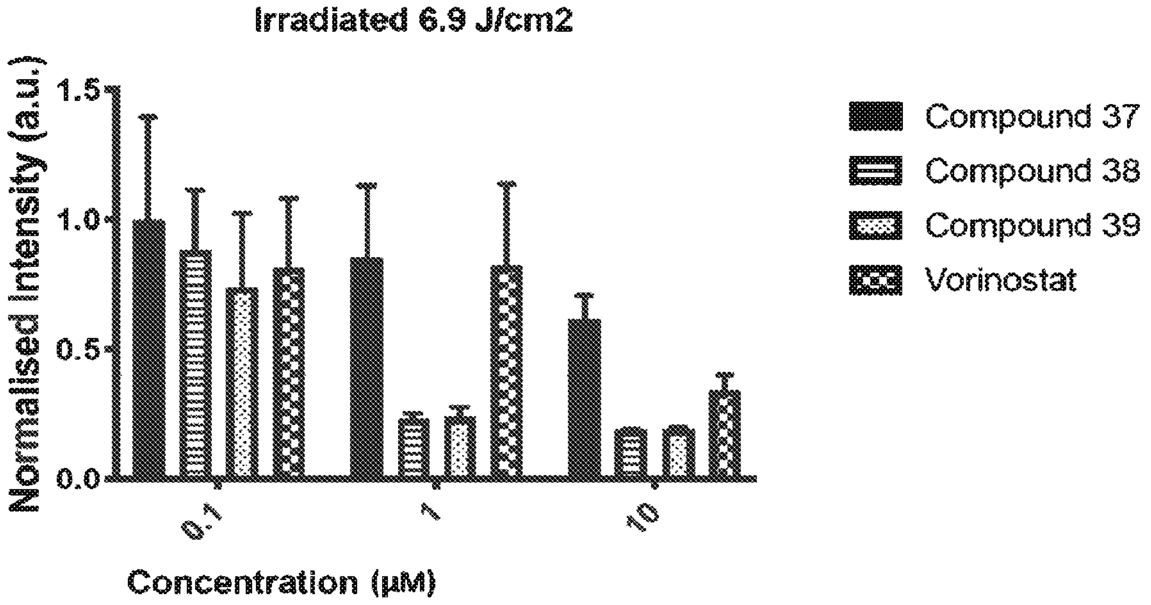

MTT assays were conducted according to the following procedure: cells were treated with compounds 37/38/39 at varying concentrations for 1 h at 37° C./5% $CO_2$whereupon they were irradiated at 56 Jmm$^{-2}$ for 5 min. Cells were then incubated for 24 h at 37° C./5%. The culture medium was removed, and cells were rinsed with PBS. Phenol free medium was added and a 12 mM MTT stock solution was added, whereupon the cells were incubated at 37° C. for 2 h. DMSO was further added and cells were incubated at 37° C. in a humidified chamber. Absorption measurements were then recorded at 540 nm to determine the extent of cell viability. The results are shown in FIG. 6.

MTT cell viability assay on SJG-41 cells treated with compound 37, compound 38, compound 39 and vorinostat for 24 hours prior to assay. Note assays measurements were normalised to DMSO treated cells (dashed line). Unirradiated compound 38 has no effect on cell viability while compound 39 causes cell death with similar potency to vorinostat alone, suggesting that conjugation of vorinostat to the fluorescent compound of the invention does not adversely impact on the cytotoxicity of vorinostat. However, after irradiation, compound 39 and compound 38 cause significant cell death. The potency of compound 39 compared to unmodified vorinostat is approximately 10-fold greater. Therefore, compound 39 exhibits an inherent cytotoxic activity from the hydroxamic acid that can be supplemented and augmented by application of UV, 405 nm or two-photon 800 nm light to induce an additional photoactivated cell-killing effect.

Example 6: Localisation of Compounds in Mammalian Cells

To study the localisation of compounds in biological cells, co-staining of compounds of formula I with specific organelle markers (fluorescent dyes and antibodies) within biological cells was conducted. The following compounds were studied: compounds 6, 7, 12, 13, 14 and 15.

Experimental

6.1 Cell lines and Media

HaCaT keratinocyte cell lines were used for the following experimental procedures. The cells were incubated in cell culture media (94% Dulbecco's Modified Eagle Medium (DMEM), 5% Foetal Bovine Serum (FBS) and 1% Penicillin Streptomycin solution (Pen-Strep).

6.2 Staining with Organelle Dyes

The cells were plated in 8-well plates, at a concentration of 25,000 cells per ml. 200 μl of cell suspension was added to each well, and the cells were incubated for 2 days before staining and imaging was carried out.

In order to visualise the mitochondria, cells were probed with the mitochondrial dye MitoTracker® Deep Red. Cells to be stained were incubated with 200 μl MitoTracker® Deep Red solution (200 nM MitoTracker® and 1 μM Formula I compound in cell culture media) per well (N=3) for 30 minutes.

Nile Red was used to identify lipids within the cells. 200 μl Nile Red Lipophilic dye (10 μg/ml Nile Red and 1 μM Formula I compound in cell culture media) was added to each well (N=3) and incubated for 30 minutes.

For the detection of lysosomes within the cells, LysoTracker® Red DND-99 dye was used. 200 μl LysoTracker® Red DND-99 (50 nM LysoTracker® and 1

μM Formula I compound solution in cell culture media) was added to each well (N=3) and incubated for 30 minutes.

For visualisation of the endoplasmic reticulum (ER), cells were stained with BODIPY® ER-Tracker® Red. 200 μl BODIPY ER-Tracker® Red (1 μM BODIPY® and 1 μM Formula I compound solution in cell culture media) was added to each well (N=3) and incubated for 30 minutes.

Following incubation, the cell culture media containing dye was removed, and cells were washed twice with 200 μl phosphate buffered saline (PBS). After washing, 200 μl PBS was added into each well for imaging.

6.3 Staining with Anti-Lamin A/C Antibody

For visualisation of the nuclear lamina, cells were probed with an anti-lamin A/C antibody. The cells were plated on 22×22 mm cover slips (10,000 cells/ml) and incubated for 2 days before staining. The cells were washed with PBS to remove excess media before staining. The cells were fixed with 4% paraformaldehyde (PFA) for 10 minutes at room temperature, before being washed twice in PBS for 5 minutes. Following washing, the cells were permeabilised in 0.4% Triton X-100 in PBS for 10 minutes. The cells were subsequently washed three times in PBS for 5 minutes, before being incubated in blocking buffer (1% BSA, 0.1% fish gelatine and 0.1% Triton X-100 in PBS) for 15 minutes at room temperature. The cells were incubated in primary antibody (mouse anti-lamin A/C IgG in blocking buffer) for 1 hour at room temperature. The cells were then washed twice in blocking buffer and incubated in secondary antibody (anti-mouse Alexa-594 IgG in blocking buffer) for 30 minutes at room temperature. Cells were washed twice in PBS for 10 minutes at room temperature.

6.4 Staining with Compounds of Formula I

For cell staining with compounds of formula I, 5 μM of the compound of formula I in PBS was added to the cells for 30 minutes at room temperature. Cells were then washed five times for 5 minutes in PBS. Following washing, the cells were mounted onto non-charged microscopy slides using 6 μl Mowiol® per cover slip as mounting media.

6.5 Imaging

A Zeiss 880 confocal microscope was used for all the imaging work.

TABLE 2

Imaging Conditions

| Compound | Excitation (nm) | Emission Range (nm) |
|---|---|---|
| Formula I Compounds | 405 | 450-550 |
| MitoTracker ® Deep Red | 633 | 640-680 |
| Nile Red | 594 | 600-640 |
| LysoTracker ® Red DND-99 | 594 | 600-640 |
| BODIPY ® ER-Tracker Red | 594 | 600-640 |
| Alexa-594 Anti-mouse IgG | 594 | 600-640 |

6.6 Analysis

ImageJ Coloc2 software was used to calculate co-localization statistics between the compounds of formula I and the organelle marker images. The background was subtracted from each image and a region of interest (ROI) was used to target the analysis. The point spread function (PSF) of each image was calculated as 2.0 and Coastes' iterations was set to 100. The statistic quantified was the Pearson's Correlation Coefficient (PCC). PCC gives a number ranging from +1 to −1:1=perfect co-localisation; 0=no relationship; and, −1=perfect anti-co-localisation.

6.7 Results

For each compound, an individual image for each of the organelle markers was captured, and these are shown in FIGS. 7 to 12. With the left-hand image (column 1) in green being the compound of Formula I, the central red image (column 2) being the organelle marker and the right-hand image (column 3) being an overlay of both images.

Figure 7:
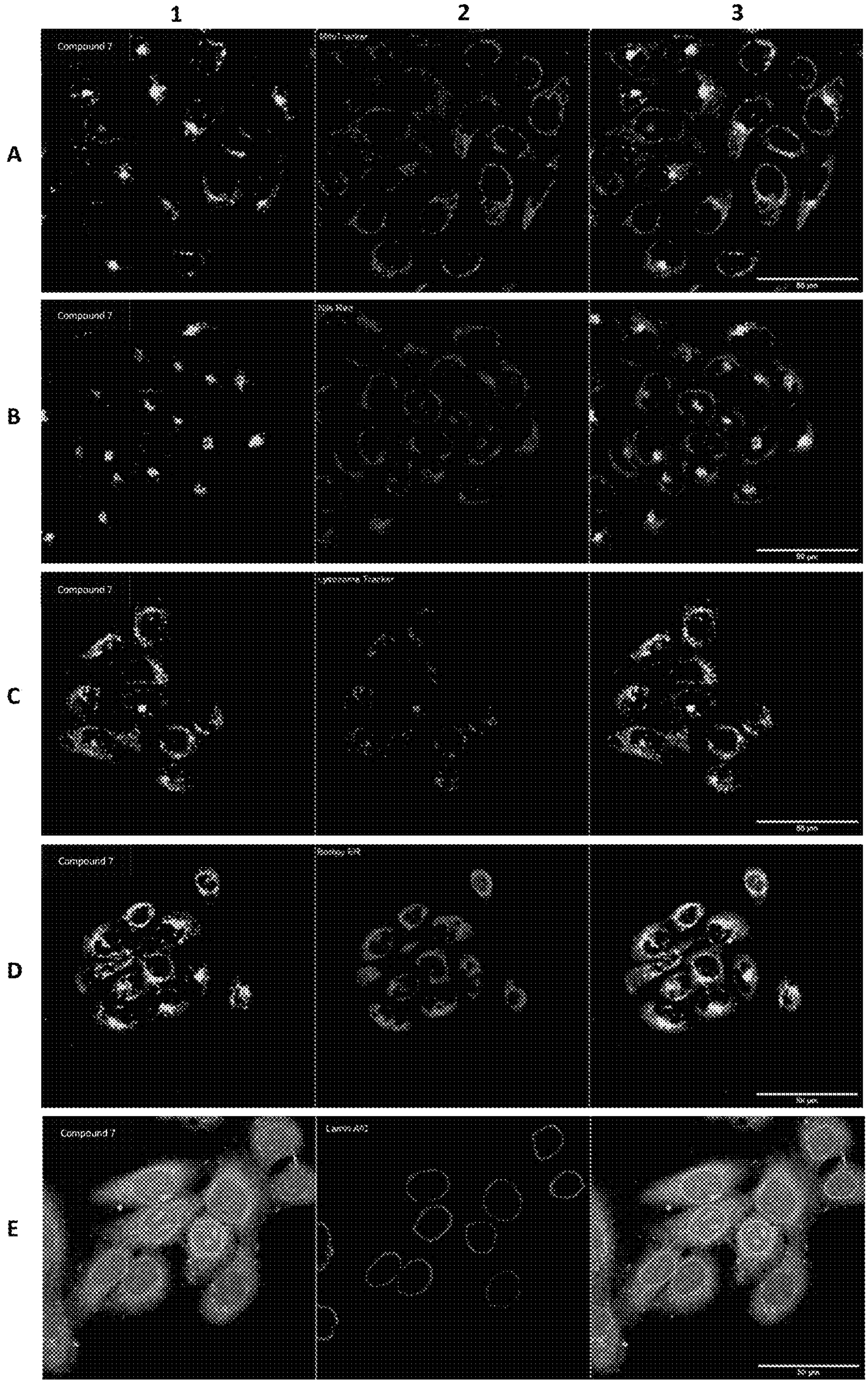
FIG. 7 shows tiled images of co-staining of HaCaT keratinocytes treated with compound 7 and a range of organelle markers.

FIG. 7 shows tiled images of co-staining of HaCaT keratinocytes probed with compound 7 and a range of organelle markers. Column 1 shows compound 7 visualised in green, column 2 shows different organelle markers visualised in red and column 3 shows an overlay of both compound 7 (green) and organelle markers (red). Row A shows MitoTracker staining (red) used to investigate mitochondrial localisation of compound 7. Row B shows Nile Red staining (red) used to investigate lipophilic localisation of compound 7. Row C shows LysoTracker® Red DND-99 staining (red), used to investigate lysosomal localisation of compound 7. Row D shows BODIPY® ER-Tracker Red (red), used to investigate localisation of compound 7 to the endoplasmic reticulum (ER). Row E shows anti-lamin A/C antibody staining (red), used to investigate localisation of compound 7 to the nuclear lamina.

Figure 8:
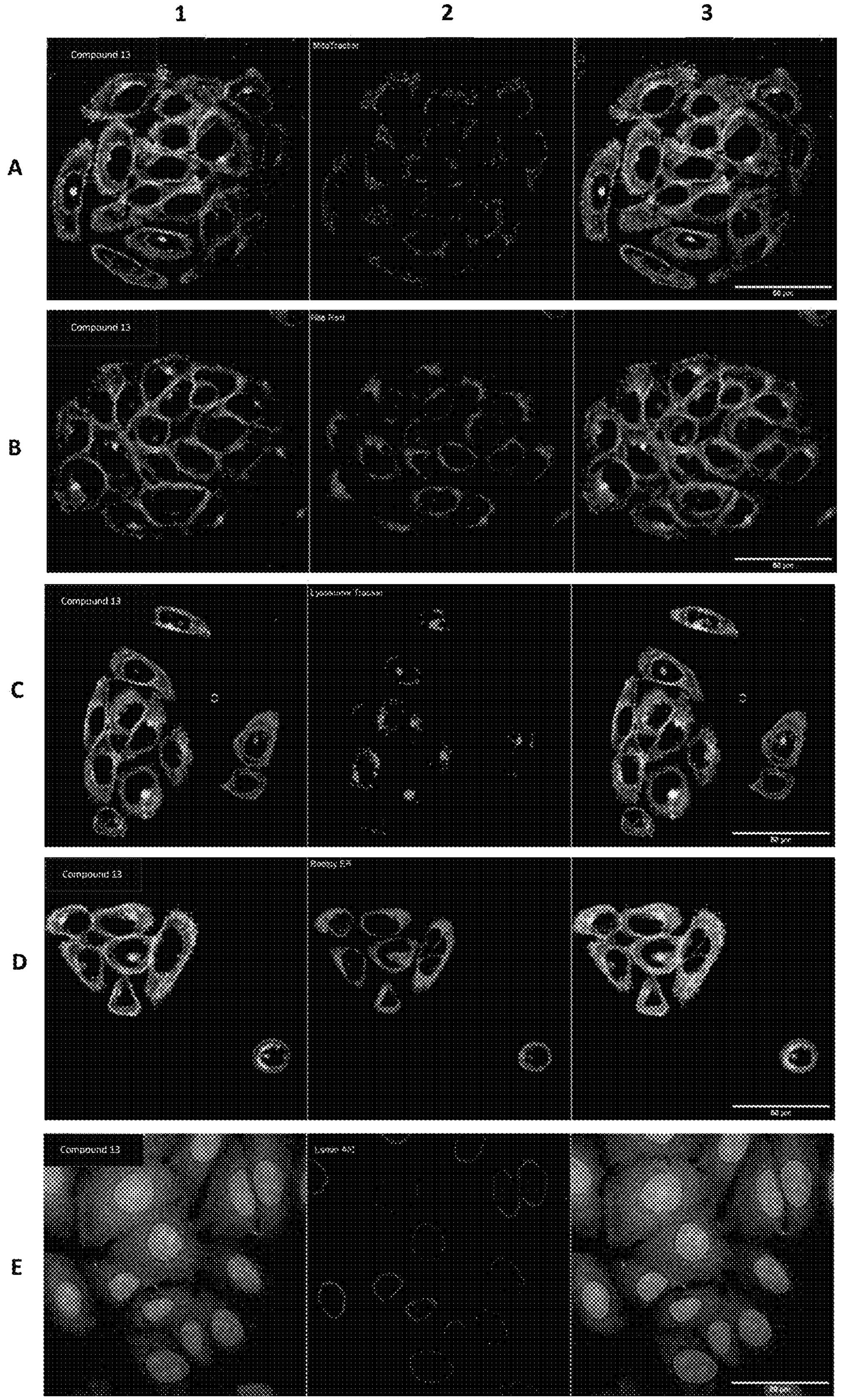
FIG. 8 shows tiled images of co-staining of HaCaT keratinocytes treated with compound 13 and a range of organelle markers.

FIG. 8 shows tiled images of co-staining of HaCaT keratinocytes probed with compound 13 and a range of organelle markers. Column 1 shows compound 13 visualised in green, column 2 shows different organelle markers visualised in red and column 3 shows an overlay of staining of both compound 13 (green) and organelle markers (red). Row A shows MitoTracker staining (red) used to investigate mitochondrial localisation of compound 13. Row B shows Nile Red staining (red) used to investigate lipophilic localisation of compound 13. Row C shows LysoTracker® Red DND-99 staining (red), used to investigate lysosomal localisation of compound 13. Row D shows BODIPY® ER-Tracker Red (red), used to investigate localisation of compound 13 to the endoplasmic reticulum (ER). Row E shows anti-lamin A/C antibody staining (red), used to investigate localisation of compound 13 to the nuclear lamina.

Figure 9:
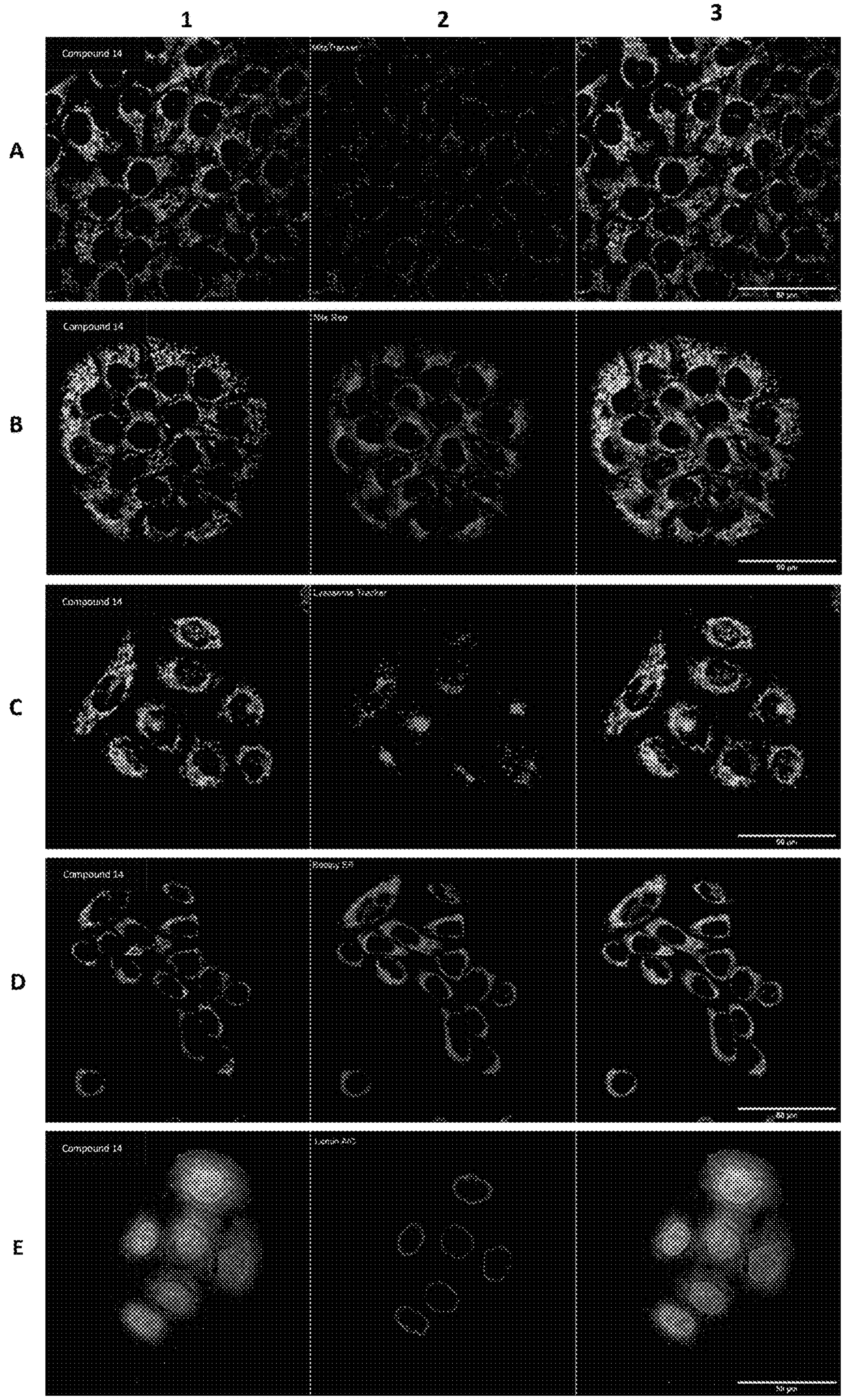
FIG. 9 shows tiled images of co-staining of HaCaT keratinocytes treated with compound 14 and a range of organelle markers.

FIG. 9 shows tiled-images of co-staining of HaCaT keratinocytes probed with compound 14 and a range of organelle markers. Column 1 shows compound 14 visualised in green, column 2 shows different organelle markers visualised in red and column 3 shows an overlay of staining of both compound 14 (green) and organelle markers (red). Row A shows MitoTracker staining (red) used to investigate mitochondrial localisation of compound 14. Row B shows Nile Red staining (red) used to investigate lipophilic localisation of compound 14. Row C shows LysoTracker® Red DND-99 staining (red), used to investigate lysosomal localisation of compound 14. Row D shows BODIPY® ER-Tracker Red (red), used to investigate localisation of compound 14 to the endoplasmic reticulum (ER). Row E shows anti-lamin A/C antibody staining (red), used to investigate localisation of compound 14 to the nuclear lamina.

Figure 10:
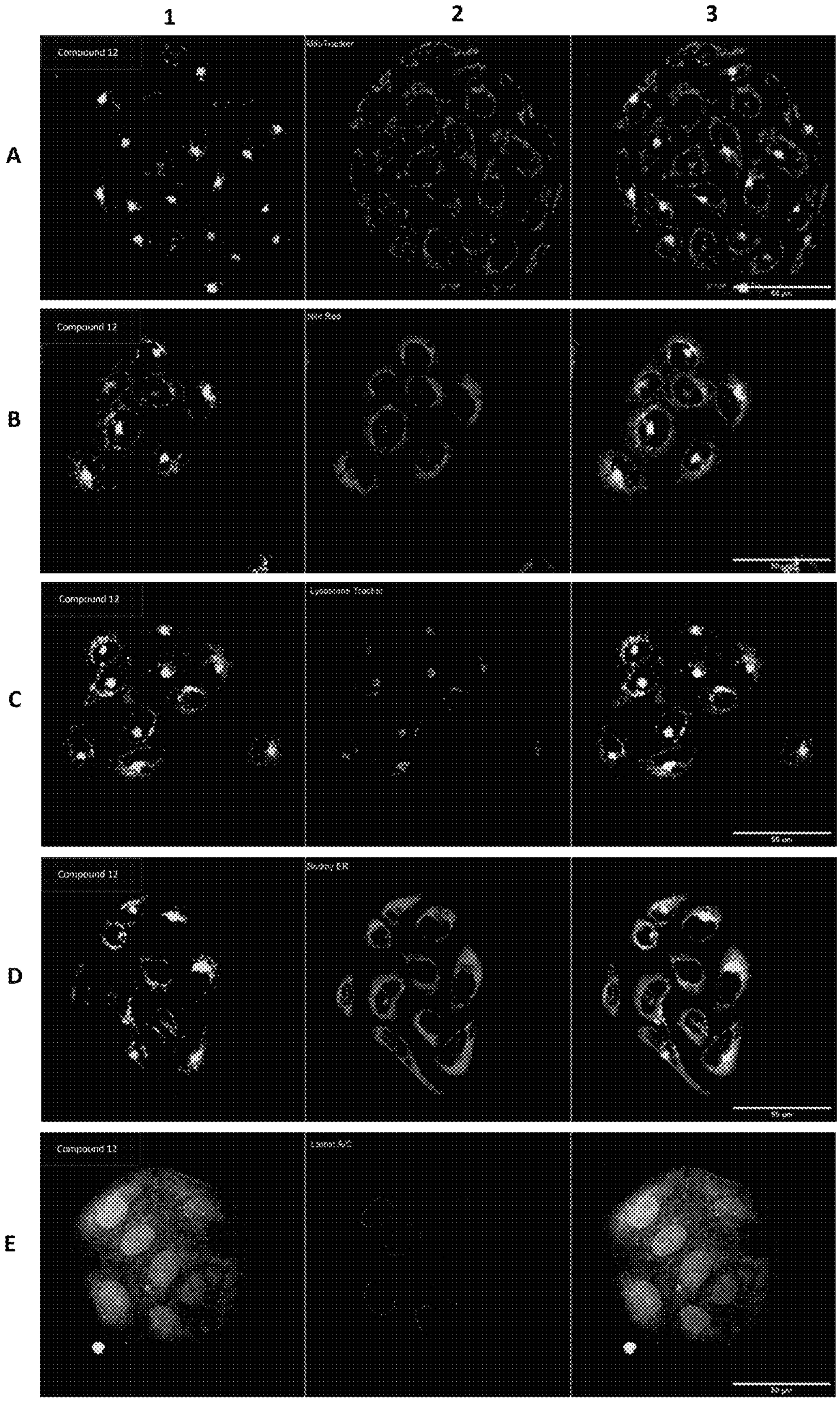
FIG. 10 shows tiled images of co-staining of HaCaT keratinocytes treated with compound 12 and a range of organelle markers.

FIG. 10 shows tiled images of co-staining of HaCaT keratinocytes probed with compound 12 and a range of organelle markers. Column 1 shows compound 12 visualised in green, column 2 shows different organelle markers visualised in red and column 3 shows an overlay of staining of both compound 12 (green) and organelle markers (red). Row A shows MitoTracker staining (red) used to investigate mitochondrial localisation of compound 12. Row B shows Nile Red staining (red) used to investigate lipophilic localisation of compound 12. Row C shows LysoTracker® Red DND-99 staining (red), used to investigate lysosomal localisation of compound 12. Row D shows BODIPY® ER-Tracker Red (red), used to investigate localisation of compound 12 to the endoplasmic reticulum (ER). Row E shows anti-lamin A/C antibody staining (red), used to investigate localisation of compound 12 to the nuclear lamina.

Figure 11:
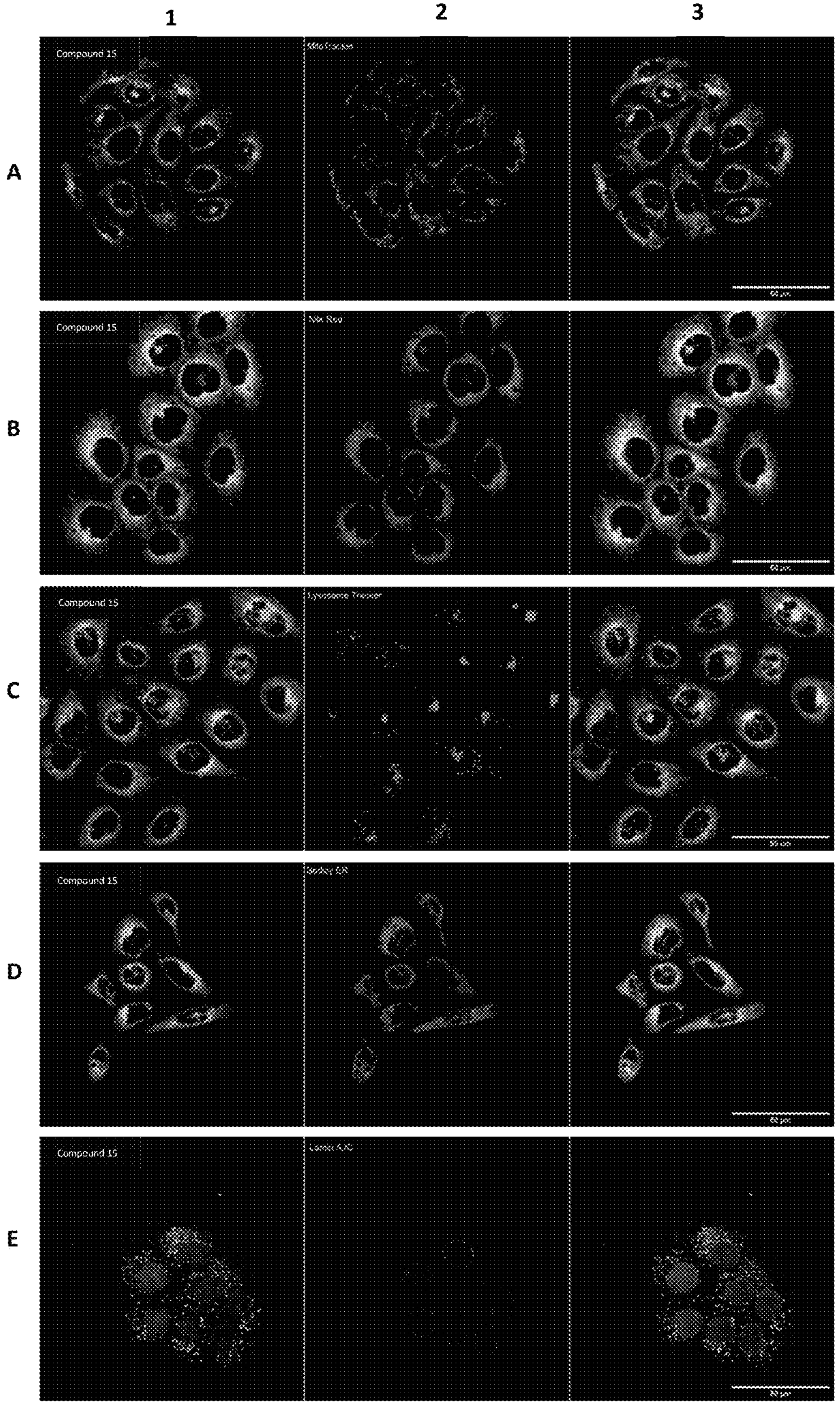
FIG. 11 shows tiled images of co-staining of HaCaT keratinocytes treated with compound and a range of organelle markers.

FIG. 11 shows tiled images of co-staining of HaCaT keratinocytes probed with compound 15 and a range of organelle markers. Column 1 shows compound 15 visualised in green, column 2 shows different organelle markers visualised in red and column 3 shows an overlay of staining of both compound 15 (green) and organelle markers (red). Row A shows MitoTracker staining (red) used to investigate mitochondrial localisation of compound 15. Row B shows Nile Red staining (red) used to investigate lipophilic localisation of compound 15. Row C shows LysoTracker® Red DND-99 staining (red), used to investigate lysosomal localisation of compound 15. Row D shows BODIPY® ER-Tracker Red (red), used to investigate localisation of compound 15 to the endoplasmic reticulum (ER). Row E shows anti-lamin A/C antibody staining (red), used to investigate localisation of compound 15 to the nuclear lamina.

Figure 12:
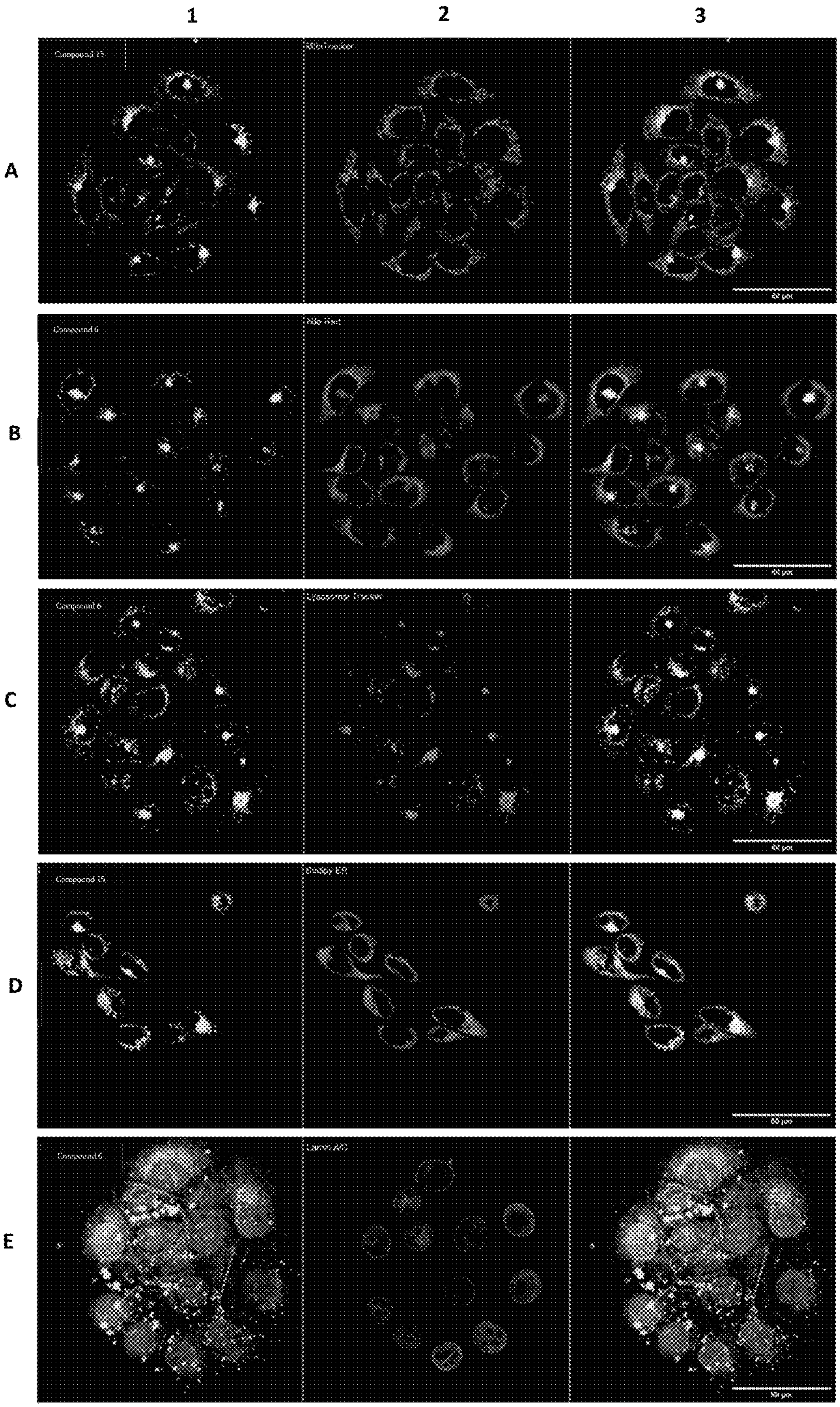
FIG. 12 shows tiled images of co-staining of HaCaT keratinocytes treated with compound 6 and a range of organelle markers.

FIG. 12 shows tiled images of co-staining of HaCaT keratinocytes probed with compound 6 and a range of organelle markers. Column 1 shows compound 6 visualised in green, column 2 shows different organelle markers visualised in red and column 3 shows an overlay of staining of both compound 6 (green) and organelle markers (red). Row A shows MitoTracker staining (red) used to investigate mitochondrial localisation of compound 6. Row B shows Nile Red staining (red) used to investigate lipophilic localisation of compound 6. Row C shows LysoTracker® Red DND-99 staining (red), used to investigate lysosomal localisation of compound 6. Row D shows BODIPY© ER-Tracker Red (red), used to investigate localisation of compound 6 to the endoplasmic reticulum (ER). Row E shows anti-lamin A/C antibody staining (red), used to investigate localisation of compound 6 to the nuclear lamina.

Tables 3 to 8 below show the average PCC values for each organelle marker indicating the extent of co-localisation with compounds 7, 13, 14, 12, 15 and 6, respectively. There are no PPC values for the anti-lamin A/C antibody as there were not enough pixels per image to produce reliable data.

TABLE 3

The average correlation (PCC) between localisation of compound 7 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | 0.12 | 0.39 | 0.75 | 0.32 | Co-localisation |

TABLE 4

The average correlation (PCC) between localisation of compound 13 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | −0.35 | 0.00 | 0.22 | −0.18 | No Co-localisation |

TABLE 5

The average correlation (PCC) between localisation of compound 14 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | 0.65 | 0.51 | 0.11 | 0.68 | No Co-localisation |

TABLE 6

The average correlation (PCC) between localisation of compound 12 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | 0.14 | 0.37 | 0.73 | 0.34 | No Co-localisation |

TABLE 7

The average correlation (PCC) between localisation of compound 15 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | 0.16 | 0.82 | 0.21 | 0.30 | No Co-loc ali-sation |

TABLE 8

The average correlation (PCC) between localisation of compound 6 and different organelle markers in HaCaT keratinocyte cells.

| Organelle Marker | MitoTracker ® | Nile Red | Lyso-Tracker ® | BODIPY ® ER-Tracker | Anti-lamin A/C |
|---|---|---|---|---|---|
| PCC Value | 0.08 | 0.42 | 0.81 | 0.48 | Co-localisation |

In summary, compound 7 primarily shows localisation to the lysosomes with some localisation to the ER and Golgi apparatus and also shows some lipophilic staining. Compound 13 appears to stain the peripheral region of the cells but shows no detectable co-localisation with the organelle markers used. Compound 14 shows localisation to the mitochondria and ER with some lipophilic staining. Compound 12 appears to primarily localise to the lysosomes with some ER localisation and lipophilic staining present. Compound 15 appears to primarily show lipophilic localisation. Compound 6 appears to primarily localise to the lysosomes with some ER localisation and lipophilic staining.

Example 7: Localisation of Compounds in Plant Cells

7.1 Preparation of Black-Grass Cell Suspension Culture

Black-grass cell suspension culture was initiated from embryogenic calli. Suspension cultures were sub-cultured every 10 days. The cells in log-phase (5 days after subculture) were used in all experiments.

7.2 Labelling

Compounds 7, 14, 12 and 15 were re-suspended in DMSO (5 mM). 10 mL of black-grass cell suspension culture were labelled with the compounds (final concentration 1 μM) for 1 h at room temperature. Cell culture were washed twice with growth media to remove the excess compounds. Cells were observed with confocal microscope (Leica SP8) using HP PL APO 63× objective lenses. Image was acquired at excitation/emission of 405/460-540 nm. The acquired images were processed by LasX software (Leica)

7.3 Cytotoxicity Assay 5 mL of black-grass cell suspension culture was treated with 0.1, 1, 5, and 10 IM of compound numbers 7, 14, 12 and 15 for 1 hour at room temperature. Cells treated with 0.1% DMSO were used as a control. Cells were irradiated (~365 nm) for 5 minutes before being incubated at 25° C., 150 rpm for 24 hours. In addition, the cytotoxicity of the compounds without irradiation was also assessed. Cell viability of five biological replicates for each concentration were determined via fluorescence assay (FDA/PI) assay. Percentage of cell viability was calculated using following formulation:

$$\% \text{ viability} = \{\text{live cells (FDA)}/(\text{live cells} + \text{dead cells})\} \times 100$$

The statistical analysis of percentage of cell viability was performed through one-way analysis of variance (ANOVA) followed by Tukey HSD posthoc test using SPSS 23 (IBM, Chicago, IL, USA).

7.4 Results

Figure 13:
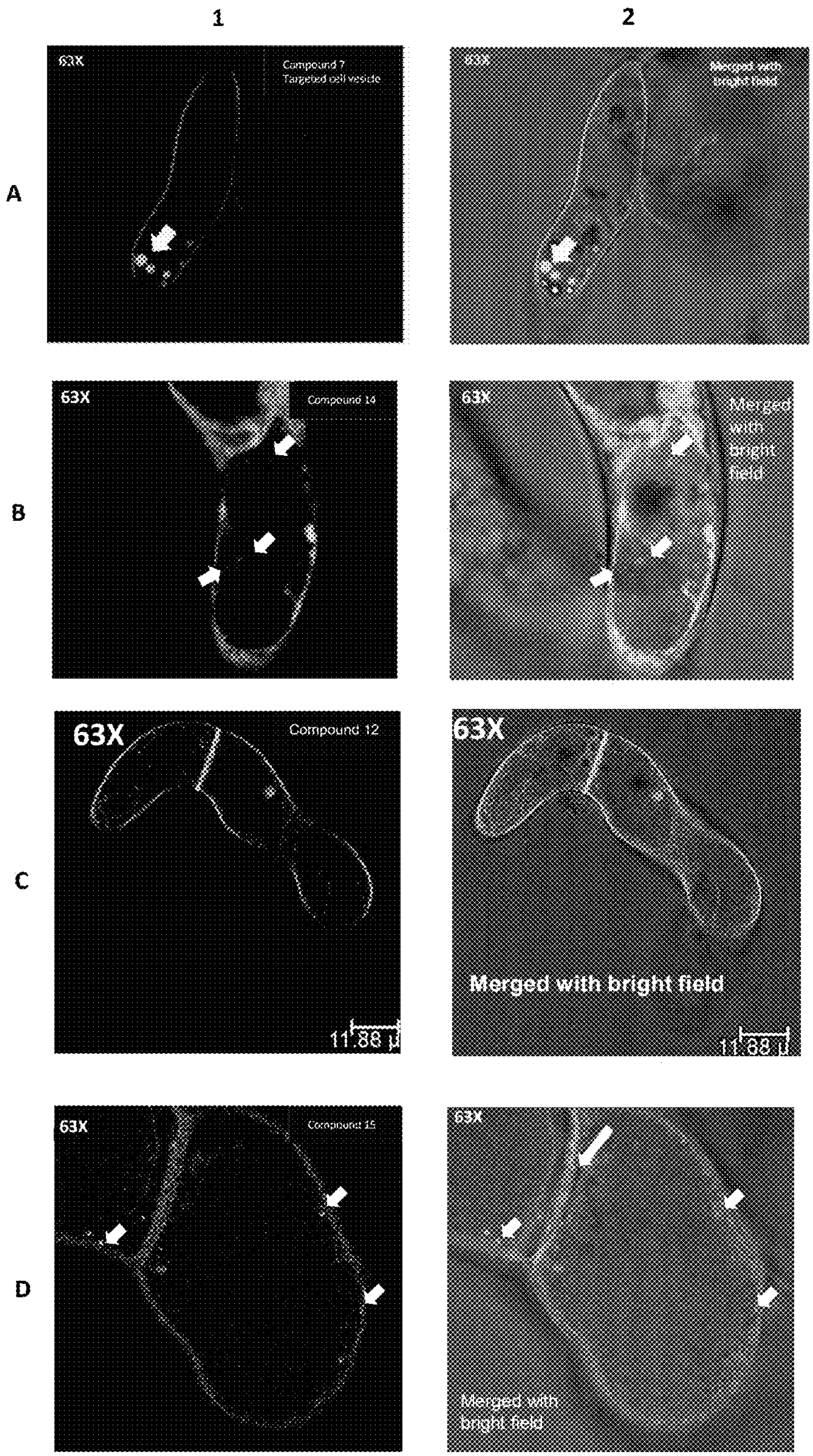
FIG. 13 shows tiled fluorescent images of the subcellular localisation of compounds 7 (row A), 14 (row B), 12 (row C) and 15 (row D) in black-grass cells.
Figure 14A:
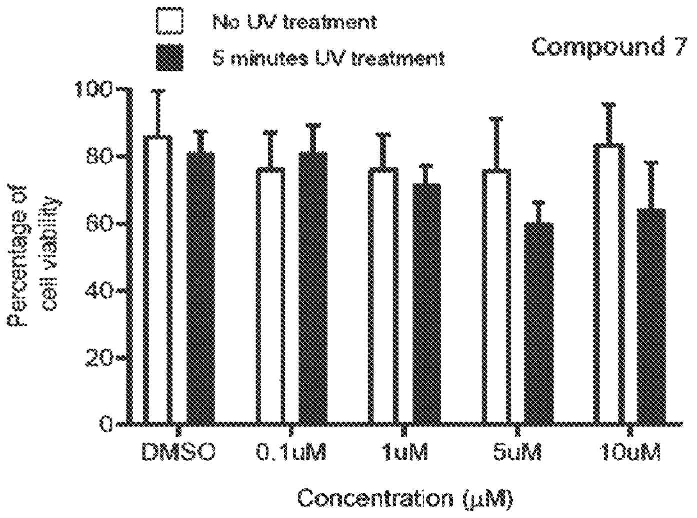
Figure 14B:
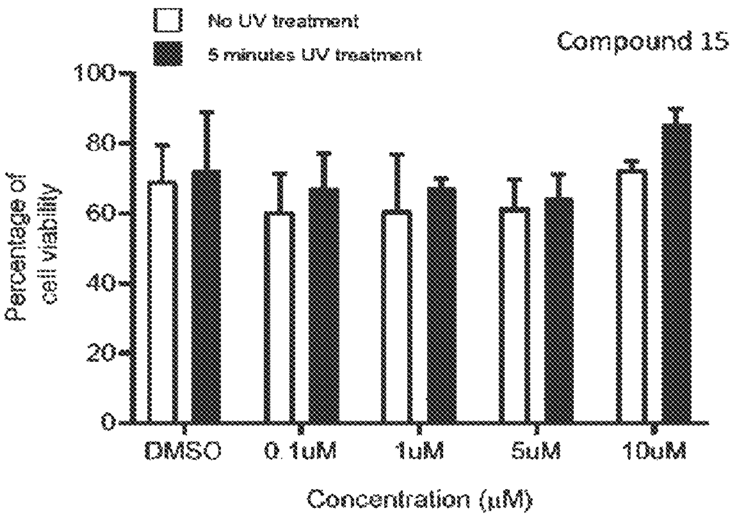
Figure 14C:
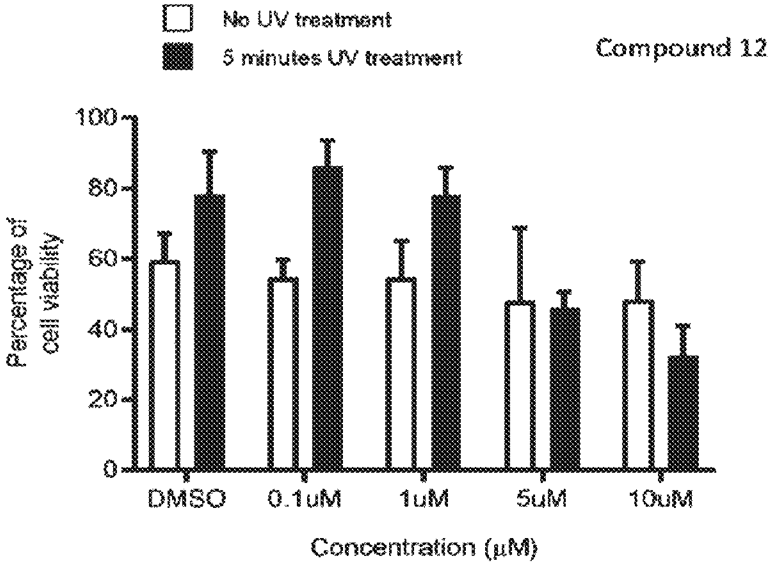
Figure 14D:
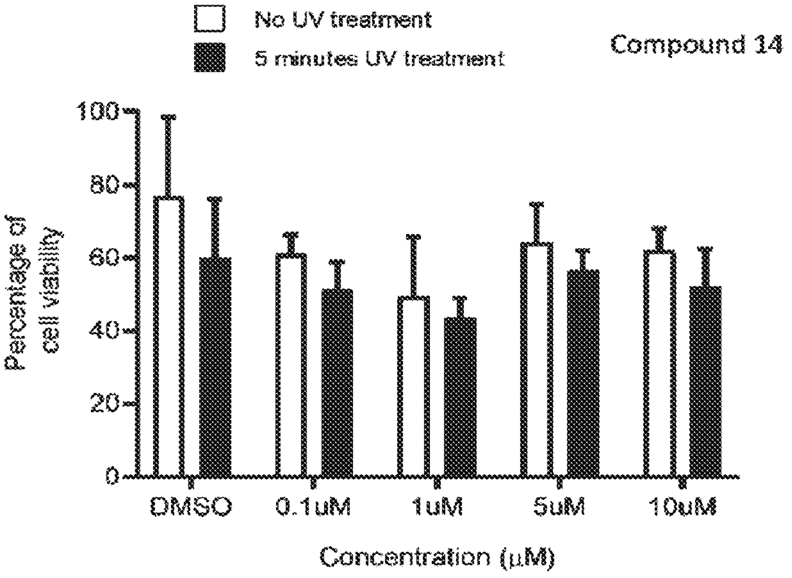

Results are shown in FIGS. 13 and 14.

7.4.1 Compound 7

Compound 7 generated an acceptable signal in black-grass cell suspension culture. As can be seen in FIG. 13, the compound seemed to label the inner cell membrane; however, compound 7 showed a stronger signal in the cell vesicle (possibly lipid vesicle).

7.4.2 Compound 14

Compound 14, which exhibits a triphenylphosphonium moiety, has been shown to target mitochondria in mammalian cells. However, this compound seemed to label inner cell membrane as well as small vesicles. Considering that mitochondria are the high abundant organelle in living organisms, compound 14 did not seem to label mitochondria in black-grass cells.

7.4.3 Compound 12

Compound 12 generated a strong signal in black-grass cells. It seemed to specifically label plasma membrane and cell plate.

7.4.4 Compound 15

Compound 15, which incorporates a tosyl sulphonamide moiety, has been shown to label the endoplasmic reticulum in mammalian cells. However, this compound seemed to label small vesicle in black-grass cells. We speculated that the small vesicles labelled by this compound could be peroxisomes.

7.4.5 Cytotoxicity of Compounds to Black-Grass Cell Culture

Results above demonstrate that the compounds of formula I appear to target different organelles in black-grass cell culture. Tests were then performed to determine whether the negative effect of these compounds on cell viability could be observed after irradiation. To ensure that irradiation was required to trigger cytotoxicity, the percentage of cell viability of black-grass cells treated with the compounds without irradiation was also assessed.

Compounds 7 and 15 did not reduce black-grass cell viability regardless of concentration or irradiation treatment. On the contrary, black-grass cell viability was significantly reduced when treated with 1 μM of compound 14. The cytotoxic effect of compound 14 at this concentration seemed to be independent of irradiation as a significant reduction of cell viability in non-irradiation treatment was observed. Black-grass cells viability was significantly reduced when treated with 5 μM and 10 μM of compound 12. Furthermore, the cytotoxic effect of compound 12 was only observed after irradiation.

Imaging and cytotoxicity assay results suggest that compound 12 specifically targets the plasma membrane in black-grass cell cultures. Furthermore, compound 12 can kill black-grass cells when applied at high concentrations (5 μM and 10 μM). Taken together, compound 12 has a high potential to be a reliable marker for plasma membrane localisation in plant cells and therefore has the potential to be used as a photosensitiser in plant systems for generation of ROS.

Example 8: Localisation of Compounds in Bacterial Cells

8.1 Preparation of Bacterial Cell Culture

*Mycobacterium smegmatis, Staphylococcus epidermis* and *Bacillus subtilis* were used in the following experimental procedures:

A sample of *S. epidermidis* was taken from a plate culture and inoculated into Luria Broth to culture overnight at 30° C. for approximately 16 hours.

A sample of *B. subtilis* was taken from a plate culture and inoculated into Luria Broth to culture overnight at 37° C. for approximately 16 hours.

A sample of *M. smegmatis* was taken from a plate culture and inoculated into Middlebrook 7H9 broth containing an added Middlebrook ADC growth supplement to culture overnight at 37° C. for approximately 16 hours.

8.2 Cytotoxicity Assay

*M. smegmatis, S. epidermis* and *B. subtilis* cultures were prepared as follows:

TABLE 9

| Bacterial culture preparations | | | |
|---|---|---|---|
| Bacterial strain | Sample Preparation (amount of overnight culture added to 5 ml fresh media, µl) | Compound of the invention | Sample treatment (amount of compound added to each preparation, µM) |
| *M. smegmatis* | 50 | Compound 12 | 0, 1, 10, 100 |
| *S. epidermidis* | 50 | Compound 6 | 0, 1, 10, 100 |
| *B. subtilis* | 50 | Compound 12 | 0, 1, 10, 100 |
| *B. subtilis* | 50 | Compound 6 | 0, 1, 10, 100 |

Samples were incubated in darkness at room temperature for approximately 2 hrs. A black clear bottom Costar™-96 well plate was then filled, with 200 µl of sample in each well Cells were irradiated for 5 minutes at approximately 15 $mW/cm^2$. The cytotoxicity of the compounds without irradiation was also assessed.

The 96 well plate was put into the plate reader and set up to run a growth curve protocol using the following parameters:

Incubation temperature: 37° C.

OD read wavelength 600 nm 250 cycles, readings every 5 mins

Shaking for 5 s pre-reading

This was left to run overnight to obtain kinetic growth curves based on optical density readings.

8.3 Staining with Compound 6 and Compound 12

*M. smegmatis, S. epidermis* and *B. subtilis* were stained with compound 6. *B. subtilis* was stained with compound 12.

Samples prepared according to Table 9 were treated with compounds by diluting 10 mM of stock solution in media to make a 100 µM concentration. This solution was then further diluted 1:10 and 1:100 in media to make 10 µM and 1 µM media solutions containing the compound. 50 µl of cell culture were then added to the 100 µM, 10 µM and 1 µM compound-containing media preparations.

8.4 Staining with propidium iodide and Syto™ 9

Following the treatment outlined in Table 9, each of the three bacterial strains were stained using a Baclight™ staining kit containing separate solutions of Syto™ 9 and Propidium Iodide. One extra sample treated with 0.1 µM of each compound was also included in this assay.

*M. smegmatis; S. epidermis* and *B. subtilis* were stained with propidium iodide to show non-viable cells and with Syto 9 to show all cells.

The following staining procedure was used:

1. 1 ml of each sample was eluted into a well of a 12-well plate;
2. One half of the 12 well plate was irradiated at approximately 15 mW/cm^2 for 5 mins;
3. The content of each well was eluted into separate Eppendorfs and centrifuged at 10,000 r.p.m for 3 mins to form a culture pellet;
4. Media was then removed, and each pellet resuspended in 200 µl of 1×PBS before being centrifuged at 10,000 r.p.m. for 3 mins.
5. A preparation of Baclight™-staining solution was made using 1 ml 1×PBS, 3 µl propidium iodide and 3 µl Syto™ 9;
6. Pellets were then resuspended separately in 200 µl of the staining solution and incubated for 15 mins at room temperature;
7. Samples were then centrifuged at 10,000 rpm for 3 minutes and resuspended in 1×PBS. This process was repeated three times to remove any excess staining solution;
8. 20 µl of each sample was dropped onto poly-L-lysine coated coverslips and left for 15 mins before removing excess sample and performing a final wash with 1×PBS;
9. Coverslips were mounted onto slides using Baclight™ mounting oil provided in the kit.

8.5 Imaging 8.5.1 Widefield Fluorescence Imaging

Images were taken using a Zeiss Cell observer widefield microscope with a 63× and 100× oil immersion lens. Blue, Green and Red filter sets were used for fluorescent imaging of the compound being investigated, Syto 9 and propidium iodide respectively (see Table 10).

TABLE 10

| Widefield imaging conditions | | | |
|---|---|---|---|
| Channel colour | Compound | Excitation Max (nm) | Emission Max (nm) |
| Blue | Compound 6/12 | 365 | 397 |
| Green | Syto 9 | 450 | 515 |
| Red | Propidium iodide | 546 | 590 |

8.5.2 Confocal Imaging

A Leica SP5 laser scanning confocal microscope was used to obtain high resolution images of *B. subtilis*. A 100× objective oil immersion lens was used with further digital magnification. A 405 nm excitation and 450 nm-600 nm emission range were used for taking the fluorescent images.

8.6 Results

Results are shown in FIGS. 15 to 21.

8.6.1 Cytotoxicity of Compound 12 in *Mycobacterium smegmatis*

FIG. 15(*i*) shows an overnight growth curve of *M. smegmatis* after treatment with compound 12, while FIG. 15(*ii*) shows an overnight growth curve of *M. smegmatis* treated with compound 12 after irradiation.

Samples with no photoactivation show no significant difference between the treated and untreated controls. The radiated samples however begin to indicate some cytotoxicity at the 100 μM concentration.

8.6.2 Cytotoxicity of Compound 6 in *Staphylococcus epidermis*

FIG. 16 shows *S. epidermidis* cells which have been treated with compound 6 before and after irradiation. Control cells without compound 6 treatment are also shown. Compound 6 is shown in blue (column 1, Syto 9 is shown in green (column 2) which highlights all viable and non-viable cells and propidium iodide is shown in red (column 3) which highlights the non-viable cells.

Images demonstrate an increase in red fluorescent cells after treatment with compound 6 compared with the untreated controls. Curves were generated by taking an average of the 8 microwell OD measurements for each sample type. Error bars represent the standard error across 8 well measurements. For 100 and 10μ concentrations, no growth is evident regardless of any photoactivation. The non-photoactivated 1 μM sample shows minor impact on growth by extended lag phase (time before growth begins) compared to the untreated controls. When 1 μM samples are photoactivated there is a significant increase in the lag phase of growth up to around 15 hrs, compared with the untreated samples which lag only for around 2 hrs.

8.6.3 Cytotoxicity of Compound 6 and 12 in *Bacillus subtilis*

FIG. 18 shows *B. subtilis* cells which have been treated with compound 12 before and after irradiation (FIGS. 18(*a*) and 18(*b*), respectively). The compound fluorescence is shown in blue (i). The cells have been co-stained with Syto 9, shown in green (2), which highlights all cells. The cells have also been stained with propidium iodide, shown in red (3) which highlights the non-viable cells.

Both the radiated and non-radiated images show fluorescence of compound 12 in the blue channel, demonstrating cellular attachment/uptake. Following irradiation, the proportion of non-viable (red) cells is increased compared to the non-irradiated sample. Hence cyto-toxicity of compound 12 seems to be present in *B. subtilis.*

FIG. 19 shows overnight growth curves of *B. subtilis* cells which have been treated with compound 12 before and after irradiation. For 100 μM and 10 μM treatment concentrations, no growth is observed regardless of any photoactivation. Both untreated control samples show similar amounts of growth. The non-irradiated 1 μM sample shows slightly less growth than the untreated samples as well as an increased lag time.

FIG. 20 shows overnight growth curves of *B. subtilis* cells which have been treated with compound 6 before and after irradiation. The non-irradiated samples show similar amounts of growth for 0, 5 and 1 μM concentrations. When radiated these samples show some growth inhibition. For 10 μM treatment concentrations, growth is reduced and lag time extended, and this effect is much more significant in the radiated sample.

Compound 12 shows more cytotoxicity at both 10 and 1 μM concentration than compound 6.

8.6.4 Localisation of Compound 12 in *Bacillus subtilis*

FIG. 21 shows *B. subtilis* cells treated with compound 12. Compound 12 appears to show enhanced localisation in the peptidoglycan regions of the *B. subtilis* cells.

Studies detailed above demonstrate cytotoxicity of both compound 6 and 12 in Gram positive cells *S. epidermidis* and *B. subtilis*. Depending on concentration, this can also be present without photoactivation. As such, these small molecule compounds represent a promising alternative to traditional antibiotics, to which many organisms are becoming resistant. The response to photoactivation could also be advantageous when treating skin diseases, or potentially used as a pesticide in the context of plant pathogens.

Attachment to the inner spore of the *B. subtilis* cell demonstrates inter cellular uptake which is often a challenge for large-molecule drugs. The sporulation cycle in such bacteria provides innate protection against harsh environments and chemical treatments so it is difficult to eradicate pathogens that can undergo this process. A method of actively killing the inner spore would provide a novel method of cell killing in sporulating pathogens.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A compound:

of formula IA:

IA

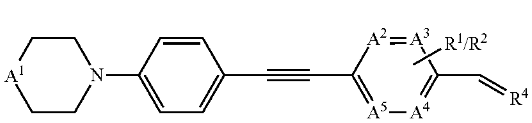

in which:

$A^1$ is $CH_2$, O, or $NR^7$, in which $R^7$ is H, an alkyl group, $—COCH_3$, $—C(O)(CH_2)_nC(O)R^8$, or $—C(O)(CH_2)_nCH(CH_3)C(O)R^8$, in which $R^8$ is —OH or —NHOH, and n is an integer from 1 to 8;

each of $A^2$, $A^3$, $A^4$ and $A^5$ is independently CH or N;

$R^1$ is H or an alkyl group comprising from 1 to 10 carbon atoms, optionally substituted with one or more N atoms, and $R^2$ is selected from an alkyl group comprising from 1 to 10 carbon atoms, optionally substituted with one or more N atoms, $—(CH_2)_nR^3$, $—(CH_2)_nNHR^3$, and $—(CH_2)_2(COCH_2)_nR^3$ in which n is an integer from 1 to 10 and $R^3$ is $—NH_2$, —OH, $—SO_2PhCH_3$, or —COOH, or $R^2$ is $—C(O)(CH_2)_nC(O)R^8$, $—C(O)(CH_2)_mO(CH_2)_mC(O)R^8$, $—C(O)(CH_2)_nCH(CH_3)C(O)R^8$, $—S(O)_2(CH_2)_nC(=O)R^8$, $—S^+(O^-)(CH_2)_nC(=O)R^8$ or $—(CH_2)_nPPh_3^+Br^-$, in which $R^8$ is —OH or —NHOH, n is an integer from 1 to 8, and m is an integer from 1 to 4;

and $R^4$ is $—CHC(=O)OR^5$, in which $R^5$ is hydrogen or $C_{1-10}$ alkyl; or $R^4$ is an optionally substituted imidazolone;

and diastereoisomers thereof, in free or salt form.

2. A probe comprising a compound of formula IA as claimed in claim 1.

3. A conjugate comprising a compound of formula IA as claimed in claim 1 and a targeting or active agent.

4. A conjugate as claimed in claim 3, wherein the targeting or active agent is selected from a small molecule drug, peptide or protein, saccharide or polysaccharide, aptamer or affimer, or antibody.

5. A compound of formula IA as claimed in claim 1, for use in the control of cellular development.

6. A compound of formula IA as claimed in claim 1 for use in photodynamic therapy.

7. A pharmaceutical composition comprising a compound of formula IA as claimed in claim 1, in combination with one or more pharmaceutically acceptable excipients, diluents or carriers.

8. A method of treatment of a patient with a disease or condition that benefits from the control of cell proliferation, differentiation or apoptosis, the method comprising administering to a patient a therapeutically effective amount of a compound of formula IA as claimed in claim 1.

9. A method of fluorescence imaging comprising administering an effective amount of the compound of formula IA as defined in claim 1 and detecting the fluorescence emitted.

10. A method of monitoring cellular development comprising administering an effective amount of the compound of formula IA as defined in claim 1 and detecting the Raman scattering signal.

11. A method of treatment of a patient with a disease or condition that benefits from the control of cell proliferation, differentiation or apoptosis, the method comprising administering to a patient a therapeutically effective amount of a conjugate as defined in claim 3.

12. A compound of Formula II:

(II)

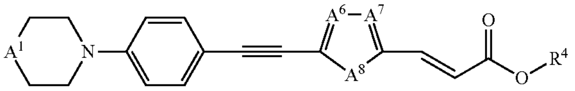

in which:

$A^1$ is $CH_2$, O, or $NR^7$, in which $R^7$ is H, an alkyl group, $—COCH_3$, $—C(O)(CH_2)_nC(O)R^8$, $—C(O)(CH_2)_nCH(CH_3)C(O)R^8$, in which $R^8$ is —OH or —NHOH, and n is an integer from 1 to 8;

$A^6$ is CH, N or S;

Each $A^7$ and $A^8$ is independently CH, S, O, N or $NR^1$, in which $R^1$ is H or an alkyl group comprising from 1 to 10 carbon atoms, optionally substituted with one or more N atoms;

and $R^4$ is hydrogen or $C_{1-10}$ alkyl;

and diastereoisomers thereof, in free or salt form.

13. A conjugate comprising a compound of formula II as defined in claim 12 and a targeting or active agent.

14. A conjugate as defined in claim 13, wherein the targeting or active agent is selected from a small molecule drug, peptide or protein, saccharide or polysaccharide, aptamer or affimer, or antibody.

15. A compound of formula II as defined in claim 12, for use in the control of cellular development.

16. A compound of formula II as defined in claim 12, for use in photodynamic therapy.

17. A pharmaceutical composition comprising a compound of formula II as defined in claim 12, in combination with one or more pharmaceutically acceptable excipients, diluents or carriers.

18. A method of treatment of a patient with a disease or condition that benefits from the control of cell proliferation, differentiation or apoptosis, the method comprising administering to a patient a therapeutically effective amount of a compound of formula II as defined in claim 12.

19. A method of treatment of a patient with a disease or condition that benefits from the control of cell proliferation, differentiation or apoptosis, the method comprising administering to a patient a therapeutically effective amount of a conjugate as defined in claim 13.

* * * * *